(12) United States Patent
To

(10) Patent No.: US 8,343,035 B2
(45) Date of Patent: Jan. 1, 2013

(54) DILATOR WITH DIRECT VISUALIZATION

(75) Inventor: John T. To, Newark, CA (US)

(73) Assignee: Spine View, Inc., Fremont, CA (US)

( * ) Notice: Subject to any disclaimer, the term of this patent is extended or adjusted under 35 U.S.C. 154(b) by 418 days.

(21) Appl. No.: 12/762,232

(22) Filed: Apr. 16, 2010

(65) Prior Publication Data

US 2011/0098531 A1    Apr. 28, 2011

Related U.S. Application Data

(60) Provisional application No. 61/170,829, filed on Apr. 20, 2009.

(51) Int. Cl.
*A61B 1/00* (2006.01)
(52) U.S. Cl. ......... 600/109; 600/114; 600/129; 600/137
(58) Field of Classification Search .................. 600/109, 600/114, 129, 137
See application file for complete search history.

(56) References Cited

U.S. PATENT DOCUMENTS

| | | | |
|---|---|---|---|
| 207,932 | A | 9/1878 | Alvord |
| 2,932,294 | A | 4/1960 | Fourestier et al. |
| 3,357,433 | A | 12/1967 | Fourestier et al. |
| 3,459,189 | A | 8/1969 | Alley at al. |
| 3,556,085 | A | 1/1971 | Takahashi |
| 4,191,191 | A | 3/1980 | Auburn |
| 4,670,008 | A | 6/1987 | Von Albertini |
| 4,763,667 | A | 8/1988 | Manzo |
| 4,801,293 | A | 1/1989 | Jackson |
| 4,848,342 | A | 7/1989 | Kaltenbach |
| 4,940,458 | A | 7/1990 | Cohn |
| 5,147,376 | A | 9/1992 | Pianetti |
| 5,156,142 | A | 10/1992 | Anapliotis et al. |
| 5,159,920 | A | 11/1992 | Condon et al. |
| 5,258,003 | A | 11/1993 | Ciaglia et al. |
| 5,271,380 | A | 12/1993 | Riek et al. |
| 5,334,150 | A | 8/1994 | Kaali |
| 5,376,076 | A | 12/1994 | Kaali |
| 5,380,291 | A | 1/1995 | Kaali |
| 5,431,151 | A | 7/1995 | Riek et al. |

(Continued)

FOREIGN PATENT DOCUMENTS

CA             2141019 C       7/1995

(Continued)

OTHER PUBLICATIONS

Anderson, D.M. et al. (Jan. 1982). "An Esophageal Fistula Dilator," *Journal of Range Management* 35(1):125-126.

(Continued)

*Primary Examiner* — W. B. Perkey
(74) *Attorney, Agent, or Firm* — Morrison & Foerster LLP; Ross M. Carothers

(57) ABSTRACT

Dilators with a threaded distal portion and direct visualization capability may be used for penetrating and dilating stiff tissues and bones. The threaded portion of a dilator engages the tissue between the insertion site and the target site, and may be rotated for advancing through the target tissue in a more controlled fashion. The direct visualization capability may be used to visualize the ligament as the threaded distal portion passes through the ligamentum flavum. The devices and methods described may be used in procedures, for example, where ligaments surrounding the epidural space need to be dilated in order to deliver one or more surgical instruments into the epidural space.

16 Claims, 29 Drawing Sheets

U.S. PATENT DOCUMENTS

| | | |
|---|---|---|
| 5,439,464 A | 8/1995 | Shapiro |
| 5,526,820 A | 6/1996 | Khoury |
| 5,551,947 A | 9/1996 | Kaali |
| 5,591,190 A | 1/1997 | Yoon |
| 5,609,562 A | 3/1997 | Kaali |
| 5,630,805 A | 5/1997 | Ternamian |
| 5,676,682 A | 10/1997 | Yoon |
| 5,685,820 A | 11/1997 | Riek et al. |
| 5,720,761 A | 2/1998 | Kaali |
| 5,746,720 A | 5/1998 | Stouder, Jr. |
| 5,853,391 A | 12/1998 | Bell |
| 5,871,470 A | 2/1999 | McWha |
| 5,882,344 A | 3/1999 | Stouder, Jr. |
| 5,976,146 A | 11/1999 | Ogawa et al. |
| 5,989,230 A | 11/1999 | Frassica |
| 6,001,084 A * | 12/1999 | Riek et al. ............ 604/272 |
| 6,007,481 A | 12/1999 | Riek et al. |
| 6,120,437 A | 9/2000 | Yoon et al. |
| 6,540,752 B1 | 4/2003 | Hicken et al. |
| 6,554,809 B2 | 4/2003 | Aves |
| 6,565,542 B2 | 5/2003 | Kumar et al. |
| 6,767,355 B2 | 7/2004 | Frova et al. |
| 7,048,717 B1 | 5/2006 | Frassica |
| 2002/0045855 A1 | 4/2002 | Frassica |
| 2005/0107800 A1 | 5/2005 | Frankel et al. |
| 2005/0251108 A1 | 11/2005 | Frassica |
| 2006/0079835 A1 | 4/2006 | Frassica |
| 2006/0206002 A1 | 9/2006 | Frassica et al. |
| 2007/0005041 A1 | 1/2007 | Frassica et al. |
| 2007/0156020 A1 | 7/2007 | Foley et al. |
| 2008/0103365 A1 | 5/2008 | Lunsford et al. |
| 2008/0154275 A1 | 6/2008 | Assell et al. |
| 2008/0234717 A1 | 9/2008 | Bruszewski |
| 2008/0255569 A1 | 10/2008 | Kohm et al. |
| 2008/0300538 A1 | 12/2008 | Schweikert et al. |
| 2009/0005645 A1 | 1/2009 | Frassica et al. |
| 2009/0018507 A1 | 1/2009 | Schmitz et al. |
| 2009/0171152 A1 * | 7/2009 | Aoki et al. ............ 600/114 |
| 2011/0098531 A1 * | 4/2011 | To ............ 600/114 |
| 2012/0065659 A1 * | 3/2012 | To ............ 606/192 |

FOREIGN PATENT DOCUMENTS

| | | |
|---|---|---|
| DE | 41 33 073 A1 | 4/1992 |
| EP | 0 312 787 A1 | 4/1989 |
| EP | 0 369 936 A1 | 5/1990 |
| EP | 0 484 725 A1 | 5/1992 |
| EP | 0 664 992 A1 | 8/1992 |
| EP | 0 694 280 A2 | 1/1996 |
| EP | 0 694 280 A3 | 1/1996 |
| FR | 1370580 A | 8/1964 |
| WO | WO-00/56389 A1 | 9/2000 |
| WO | WO-01/91651 A1 | 12/2001 |
| WO | WO-2004/019760 A2 | 3/2004 |
| WO | WO-2004/019760 A3 | 3/2004 |
| WO | WO-2004/037097 A1 | 5/2004 |
| WO | WO-2006/093976 A1 | 9/2006 |
| WO | WO-2007/031264 A1 | 3/2007 |
| WO | WO-2007/103161 A2 | 9/2007 |
| WO | WO-2007/103161 A3 | 9/2007 |
| WO | WO-2008/116563 A1 | 10/2008 |

OTHER PUBLICATIONS

Anonymous. (Date Unknown). "Angiotech:Dilators," *PBN Medicals* 1 page.

Anonymous. "The Genius of Simplicity, Evolution Mechanical Dilator System," Cook Medical, 1 page.

Bassett, E.K. et al. (Apr. 7, 2009). "Design of Mechanical Clutch-Based Needle-Insertion Device," *PNAS* 106(14):5540-5545.

Birbicer, H. et al. (Jul.-Dec. 2008). "Percutaneous Tracheostomy: A Comparison of PercuTwist and Multi-Dilatators Techniques," *Annals of Cardiac Anaesthesia*, as posted on <http://www.annals.in>, last visited on Apr. 6, 2009, 11(2):131.

Cook Medical (Date Unknown). "Lead Extraction; Evolution Mechanical Dilator System," 1 page.

Frölich, M.A. et al. (2001). "Pioneers in Epidural Needle Design," *Anesthesia & Analgesia* 93:215-220.

International Search Report mailed on Jul. 13, 2010, for PCT Application No. PCT/US2010/031620, filed on Apr. 19, 2010, 4 pages.

Meteko Instrument AB (Date Unknown). "Rusch, PercuTwist," 3 pages.

Riley, E.T. et al. (Oct. 2007). "The Episure™ Syringe: A Novel Loss of Resistance Syringe for Locating the Epidural Space," *International Anesthesia Research Society* 105(4): 1164-1166.

Stryker (2009). "Dilator Set," 1 page.

Westphal, K. et al. (2003). "PercuTwist: A New Single-Dilator Technique for Percutaneous Tracheostomy," *Anesth. Analg.* 96:229-232.

Written Opinion mailed on Jul. 13, 2010, for PCT Application No. PCT/US2010/031620, filed on Apr. 19, 2010, 4 pages.

* cited by examiner

DILATOR WITH DIRECT VISUALIZATION

CROSS-REFERENCE TO RELATED APPLICATIONS

This applications claims benefit from U.S. Provisional Application Ser. No. 61/170,829, filed Apr. 20, 2009, which is hereby incorporated by reference in its entirety. This application is also related to U.S. application Ser. No. 12/582,638, filed Oct. 20, 2009, which is also hereby incorporated by reference in its entirety.

BACKGROUND OF THE INVENTION

Injured intervertebral discs are generally treated with bed rest, physical therapy, modified activities, and pain medications for substantial treatment durations. There are also a number of treatments that attempt to repair injured intervertebral discs and to avoid surgical removal of injured discs. For example, disc decompression is a procedure used to remove or shrink the nucleus, thereby decompressing and decreasing the pressure on the annulus and nerves. Less invasive procedures, such as microlumbar discectomy and automated percutaneous lumbar discectomy, remove the nucleus pulposus of a vertebral disc by aspiration through a needle laterally inserted into the annulus. Another procedure involves implanting a disc augmentation device in order to treat, delay, or prevent disc degeneration or other disc defects. Augmentation refers to both (1) annulus augmentation, which includes repair of a herniated disc, support of a damaged annulus, and closure of an annular tear, and (2) nucleus augmentation, which includes adding or removing material to the nucleus. Many conventional treatment devices and techniques, including open surgical approaches, involve muscle dissection or percutaneous procedures to pierce a portion of the disc under fluoroscopic guidance, but without direct visualization. Several treatments also attempt to reduce discogenic pain by injecting medicaments or by lysing adhesions in the suspected injury area. However, these devices also provide little in the form of tactile sensation for the surgeon or allow the surgeon to atraumatically manipulate surrounding tissue. In general, these conventional systems rely on external visualization for the approach to the disc and thus lack any sort of real time, on-board visualization capabilities.

Accurately diagnosing back pain is often more challenging than expected and often involves a combination of a thorough patient history and physical examination, as well as a number of diagnostic tests. A major problem is the complexity of the various components of the spine, as well as the broad range of physical symptoms experienced by individual patients. In addition, the epidural space contains various elements such as fat, connective tissue, lymphatics, arteries, veins, blood, and spinal nerve roots. These anatomical elements make it difficult to treat or diagnose conditions within the epidural area because they tend to collapse around any instrument or device inserted therein. This may reduce visibility in the epidural space, and may cause inadvertent damage to nerve roots during device insertion. Also, the insertion of a visualization device may result in blocked or reduced viewing capabilities. As such, many anatomical elements within the epidural space may limit the insertion, movement, and viewing capabilities of any access, visualization, diagnostic, or therapeutic device inserted into the epidural space.

BRIEF SUMMARY OF THE INVENTION

Some embodiments herein relate to cannula retractor systems for accessing and visualizing the spine and related methods of treatment. In some examples, the retractor assembly may be used to create a working space and/or having an atraumatic configuration that may be used to displace or dissect tissue. In some further examples, the retractor assembly may comprise a set of jaws about the distal end of a cannula which may be opened to create a larger visualization field and working space. Endoscopes and various therapeutic tools located in the cannula may be used as the jaws are kept open, or in some instances, when the jaws are in a closed position. The devices and methods described herein may be used, for example, to perform annulus repair, herniated disc excision, denervation of neurological tissue, or the removal of bony material from the spine. The devices and methods may also be used to deliver pharmacological agents and/or cell or tissue therapy agents, to diagnose disc degeneration or other defects, and bony degeneration, to treat spinal stenosis, and to perform nucleus decompression, or disc augmentation.

In one embodiment, a method of accessing a portion of the spine including percutaneously approaching a portion of the spine with an instrument having direct visualization capability, providing an access to a portion of the spine using the instrument, and positioning a device about the portion of the spine using the instrument. In a further embodiment, the instrument may comprise a retractor assembly and the method may include passing the retractor assembly in a closed configuration to a spine region, and actuating the retractor assembly to an open configuration. In another embodiment, the retractor assembly may comprise a material or marker to augment visualization of the structure by imaging modalities used inside or outside of the body. A diagnostic device, a therapy delivery device, a stimulation device or a pharmacological therapy device may be also inserted into the instrument and to the spine region. In another embodiment, the method includes implanting a device using the direct visualization capability of the instrument. In still other embodiments, a method includes providing access to a portion of the spine, such as the spinal epidural space, the annulus, the layers of annulus, the disc nucleus, the facet joints, the foramen, or the spine musculature. In still another embodiment, the method also includes receiving visualization information from an imaging modality located outside of the body such as fluoroscopy, magnetic resonance imaging, and/or computer tomography. In still other embodiments, the method includes using the direct visualization capability of the instrument to maneuver the instrument between a spinal nerve root, the spinal dura and nerve tissue and other tissues, and/or atraumatically manipulating the spinal nerve root or other soft tissue. In yet another embodiment, the method includes using the instrument to deliver disc augmentation devices, nucleus augmentation devices or disc excision devices. In another embodiment, the instrument may be used for diagnostic purposes.

In one embodiment, a retractor cannula system may comprise at least two interlocking jaws that have a substantially rounded or curved geometry when in the closed configuration. Following positioning of the retractor cannula system about the target site, the jaws of the retractor assembly may be placed in the open configuration and may be used as an atraumatic tool for dissection and/or a displacing tissue to create working space, thereby enhancing visualization of other surrounding structures. In one embodiment, the retractor assembly is a forward-looking structure so that the distal tip of the retractor assembly may push obstructive tissue away from the scope, and the distal tip of the retractor assembly may provide a depth of view between the scope and the targeted sites to be treated.

One embodiment is directed to a retractor cannula device comprising a multi-lumen elongate shaft, a retractor assembly attached at its distal end of the shaft, wherein the retractor assembly comprises at least two jaws that are pivotably coupled to the distal section of the elongate shaft, capable of a first closed configuration and a second open configuration, wherein the second open configuration may displace tissue, expand the visual field, and/or maintain a working field. In one embodiment, the jaws of the retractor assembly form a bullet-shaped or duckbill-shaped tip when in the closed configuration. In other embodiments, the retractor assembly may have any of a variety of other shapes, tapered or not. In certain embodiments, the jaws may be made of an optically opaque material or an optically transparent material. In some examples, an endoscope or fiber optic line within the elongate shaft with an optically transparent retractor assembly may be used visualize the surrounding tissue when the jaws are in either the open and closed configuration.

Some embodiments may also comprise a retractor assembly catheter having a proximal portion and a distal portion and one or more lumens, wherein said proximal portion contains 3 separate lumens, one of said lumens being suitable for allowing the passage of an endoscope, one of said lumens being suitable for aspiration and/or irrigation, and the other lumen being suitable for allowing passage of therapeutic instruments or infusion of medications. In other embodiments, the inner edge of the jaws may be hinged to allow an angle to be formed in the open configuration, the angle being anywhere from about 1 degree to about 359 degrees. In certain embodiments, the hinge may be a rivet or screw around which the jaws rotate, and in certain embodiments, the hinge may be a living hinge involving the flexion of a pliable material.

In another embodiment, an apparatus and method for treating spinal disorders is provided, which comprises introducing a retractor cannula device having direct visualization capability into a patient, steering the retractor cannula device to a position about the spinal targeted site using visualization information provided by an endoscope or other visualization device in combination with the retractor cannula device, dissecting and/or displacing tissue with the retractor assembly of the retractor cannula device to create a working space, and using the retractor cannula device to provide a disc augmentation device in the working space for treating disc degeneration or disc defects.

In another embodiment, a method for treating intervertebral disc degeneration or defects in a spine of a body includes making an incision into a skin of the body, introducing a retractor cannula device that permits direct visualization into a portion of the spine, introducing a therapy device into retractor cannula device, and treating the disc degeneration or other defects.

In another embodiment, a method for treating intervertebral disc degeneration or other defects includes introducing a retractor cannula device that permits direct visualization capability into a portion of the spine, steering the retractor cannula device to a position adjacent to a disc or neural tissue using visualization information provided by a visualization system, displacing the neural tissue or other tissues with the retractor cannula device to create a working area, using the retractor cannula device to deliver a therapy device for treating intervertebral disc degeneration or other defects, and treating the disc degeneration or other defects. The visualization system may be used in conjunction with the retractor cannula device or may be integrated with the retractor cannula device. In some embodiments, the therapy device is a nucleus decompression device configured to inject substances and/or remove material from the nucleus, the annulus, or one or more fragmented segments of the vertebral disc. In some embodiments, a therapy device may be used to shrink a portion of the nucleus or the annulus. Treating the disc degeneration or other defects may also comprise repairing a herniated disc, supporting a damaged annulus, adding or removing material with respect to the nucleus, annulus or a bony structure, and/or sealing an annulus. In one embodiment, displacing the tissues comprises actuating the retractor structure of the retractor cannula device to an open or wider configuration.

In another embodiment, a system for intervertebral disc augmentation includes a retractor cannula device configured to provide access for a disc augmentation device to an intervertebral disc. In one embodiment, the retractor cannula device includes an elongate body, one or more movable jaws, a direct visualization device, and at least one working channel. The jaws may be coupled to the elongate body in any suitable hinge configuration or other articulation, and is configured to at least transition from a closed to and open configuration. In one or more of the embodiments, the jaws may be configured to displace tissues in the spinal area, and to create a working area. A direct visualization device inserted into the retractor cannula device or may be integral with the retractor cannula device, using a fiber optic line or an imaging sensor located on the direct visualization device. In some embodiments, the augmentation device comprises at least one mesh, cage, barrier, patch, scaffold, sealing means, hydrogel, silicone, growth factor, or combination thereof. In some embodiments, the augmentation device may be an ablation device, a balloon, or a temperature-controlled energy element, for example. The energy element may be a thermal energy device that delivers resistive heat, radiofrequency, coherent and incoherent light, microwave, ultrasound or liquid thermal jet energies to the nucleus.

In another embodiment, a method of diagnosing disc degeneration or other defects in a patient includes introducing a retractor cannula device permitting direct visualization capability into a portion of the spine, steering the retractor cannula device using visualization information provided by the retractor cannula device, displacing the neural tissues or other tissues with the retractor cannula device to create a working area, and assessing the targeted site. The retractor cannula device may comprise a material or marker to enhance visualization of the structure using an imaging modality outside of the body. The method may include receiving visualization information from an imaging modality outside of the body, such as fluoroscopy, CT and/or magnetic resonance imaging. The visualization information may also be provided by an image generated by a sensor located on the visualization device. The retractor cannula device may also include a sensor for collecting diagnostic data.

In another embodiment, a kit for augmenting the intervertebral disc may include at least one disc augmentation device, a retractor cannula device having a duckbill-shaped retractor assembly at its distal tip, an endoscopic mechanism having direct visualization capabilities, and instructions for locating the at least one disc augmentation device using the retractor cannula device. The kit for decompressing the nucleus of an intervertebral disc may also include at least one nucleus decompression device, a retractor cannula device at its distal tip that permits direct visualization using an endoscope or other visualization system, and instructions for decompressing the nucleus of an intervertebral disc using the retractor cannula device.

In another embodiment, a method for treating intervertebral disc degeneration or other defects includes introducing a retractor cannula device permitting direct visualization into a portion of the spine using a visualization mechanism, displacing the spinal tissue with the retractor cannula device to create a working area, and using the retractor cannula device to deliver a stimulation electrode device for treating intervertebral disc degeneration or other defects. In one or more of the embodiments, the retractor cannula device may be steered to a position about the spinal column by direct visualization of the visualization mechanism. The method may also include, steering the retractor cannula device using visualization information provided by the visualization mechanism, displacing the tissues in spinal area with a portion of the retractor cannula device to create a working area, and using the retractor cannula device to deliver a stimulation electrode device for treating intervertebral disc degeneration or other defects. The visualization mechanism, such as an endoscope, may be placed into the retractor cannula device or may be integrally formed with the retractor cannula device.

In another embodiment, a retractor cannula device for assessing a target site within the body may include a multi-lumen elongate shaft and a retractor assembly attached at a distal end of the shaft, wherein the retractor assembly is comprised of at least two jaws coupled to the shaft via any suitable articulation, including hinge structures, such that the jaws may have a closed configuration and an open configuration. In the closed configuration, the jaws may mate with one another such that a substantially smooth and rounded tip is formed. In the open configuration, the jaws are moved outward, increasing the angle between their inner edges, which may be used to dilate tissue and to increase the field of view.

In another embodiment, a retractor cannula device for visualizing a target site within body may include a proximal portion and a distal portion, at least three lumens positioned within the proximal portion, wherein at least one lumen is configured for insertion of an endoscope, and at least one lumen is suitable for allowing passage of therapeutic instruments or injection of medications. A retractor assembly may be attached to the distal portion of the retractor cannula device, and at least part of the distal portion of the retractor cannula device may be configured such that in at least one configuration, the jaws of the retractor assembly may allow direct visualization. In some embodiments, the jaws of the retractor assembly are constructed of opaque or transparent materials, for example any polyester copolymer (PETG, PETE), nylon, urethane, polycarbonate, acrylic, silicone, and/or glass.

In another embodiment, a retractor cannula device may include an elongate shaft having a proximal portion and a distal portion, wherein the proximal portion contains four separate lumens, one of said lumens being configured for the passage of the endoscope and/or irrigation therethrough, one of said lumens being configured for the passage of therapeutic instruments and/or aspiration, one of the said lumens being configured for the actuating members that manipulate the jaws of the retractor assembly, and one of said lumens for additional aspiration or irrigation. The distal portion of the retractor cannula device may comprise lumen openings, with one of said lumen openings in continuity with the lumen for the endoscope and/or irrigation, one of said lumen openings in continuity with the lumen for therapeutic instruments and/or aspiration, and one of said lumen openings in continuity with the lumen for additional aspiration or irrigation. The use of any one lumen need not be limited to a particular instrument or procedure, and may be used differently from the exemplary embodiments disclosed herein. In some embodiments, two or more lumens may be used for the same purpose during a procedure.

In one embodiment, a minimally invasive spinal endoscopy system is provided, comprising a tubular shaft with a slotted flexion zone, at least two slidable control wires, a proximal end, a distal end, at least two irrigation channels, at least one non-circular instrument channel, and a visualization channel. In some examples, the tubular shaft may have an average diameter of less than about 3.5 mm, or less then 2.5 mm, or even less than 1.5 mm. The system may further comprise an actuator attached to at least two slidable control wires, a housing enclosing the proximal end of the tubular shaft and at least a portion of the actuator, and a retractor assembly. The minimally invasive spinal endoscopy system may also further comprise a guidewire, a dilator, an introducer sheath, a tissue debrider, a retractor assembly, a coagulation probe, and an infusion cannula configured for insertion into at least one instrument channel.

In another embodiment, a minimally invasive device for use in a body is provided, comprising a tubular body comprising a proximal end, a distal end, a first lumen therebetween, and a retractor assembly control lumen, and a retractor assembly with at least two jaws in communication with the retractor assembly control lumen, a proximal end, and a distal end. The retractor assembly may also have a closed configuration with a reduced profile and an open configuration with an enlarged profile. In some examples, the retractor assembly may be biased to the closed configuration, the open configuration, or a third configuration. The retractor assembly may comprise a rounded or duck bill shape.

In one embodiment, a kit for performing a medical procedure may be provided, comprising a cannula with a cannula lumen configured to accommodate an endoscope, a distal retractor assembly with a working space, and a rotatable tissue removal device configured for insertion through the cannula and into the working space of the distal retractor assembly. The kit may also further comprise an endoscope configured for insertion into the cannula.

In another embodiment, a method for minimally invasively accessing a body site is provided, comprising inserting a tubular body toward a non-vascular target site in a body, actuating a retractor assembly of the tubular body from a closed to an open configuration while in the body, and visualizing the non-vascular target site from the tubular body and through a working space of the retractor assembly. The method may also optionally comprise inserting an endoscopic device into the tubular body. The method may also include advancing the distal end of the tubular body toward a neural structure in contact with a non-neural structure, and displacing the neural structure from the non-neural structure using the retractor assembly.

Another embodiment comprises a method for treating intervertebral disc degeneration or other defects in a spine, which may involve introducing a retractor cannula device having direct visualization capability into a portion of a spine, distracting the retractor assembly cannula to the open configuration to create a forward looking capability to enhance visualization and displacement of tissues, and introducing a therapy device into the retractor cannula device to treat disc degeneration or other defects. The therapy device may be any of a variety of therapy devices, including implants configured to provide structural support to a disc annulus of the spine, device configured to seal a torn annulus, and/or those instruments that add and/or remove additional material to the nucleus.

In some embodiments, a method for treating intervertebral disc degeneration or other defects in a spine of a body may comprise making an incision into a skin of the body, introducing a retractor cannula device with a direct visualization component into a portion of the spine, manipulating the retractor assembly from a closed to an open configuration to provide an enlarged working space to augment tissue visualization and displacement, introducing a therapy device into the retractor cannula device, and treating the disc degeneration or other defects.

In another embodiment, a method for treating intervertebral disc degeneration or other defects may comprise introducing a retractor cannula device having direct visualization capability into a portion of the spine, steering the retractor cannula device to a position adjacent an outer surface of the disc or nervous tissues using visualization information provided by the retractor cannula device, displacing the nervous tissues or other tissues with a portion of the retractor cannula device to create a working area, using the retractor cannula device to deliver a therapy device for treating intervertebral disc degeneration or other defects, and treating the disc degeneration or other defects. The therapy device may be a nucleus decompression device to remove a portion of the nucleus, annulus, or fragmented segments, or a therapy device shrinks a portion of the nucleus or annulus, for example. More than one therapy device may be provided or used with the retractor cannula device. Treatment of the disc degeneration or other defects may comprise repairing a herniated disc, supporting a damaged annulus, sealing an annulus, adding material or removing material with respect to the nucleus or annulus, and/or dilating or displacing spinal tissue using the retractor cannula device.

Dilators with a threaded distal portion may be used for penetrating and dilating stiff tissues and bones. Once the threaded portion of a dilator engages the target tissue, the dilator may be rotated for advancing through the target tissue in a more controlled fashion. The devices and methods described may be used in procedures, for example, where ligaments surrounding the epidural space need to be dilated in order to deliver one or more surgical instruments into the epidural space.

In some embodiments, a threaded dilator comprises an elongate shaft with a threaded portion at the distal end of the shaft. The dilator further comprises an interior lumen, which is in fluid communication with a distal port located at the distal end of the dilator and a proximal port on the shaft of the dilator. In some embodiments, the proximal port may be connected to a pressure applicator, which may be used to apply pressure to the distal port of the dilator via the dilator lumen. In some embodiments, the pressure applicator comprises a pump. In other embodiments, the pressure applicator comprises a syringe.

In some embodiments, the threaded portion of a threaded dilator comprises a taper configuration. The taper angle of the dilator may be in the range of about 5 degrees to about 45 degrees. In some embodiments, the longitudinal length of the taper may be in the range of about 0.5 mm to about 5 mm.

In some embodiments, a threaded dilator comprises a single thread, which may comprise a helix angle in the range of about 5 degrees to about 85 degrees, a thread pitch in the range of about 0.25 mm to about 1.5 mm, a thread width in the range of about 0.05 mm to about 0.5 mm, and a thread depth in the range of about 0.05 to about 0.5 mm. In some embodiments, a threaded dilator may comprise a double threaded distal portion. In yet other embodiments, a threaded dilator may comprise more than one threaded regions.

In some embodiments, a method for dilating a target tissue includes introducing a dilating device having a distal threaded portion to the target tissue, pushing the dilating device axially until the thread portion engages the target tissue, and rotating the dilating device until the distal end of the dilating device passes through the target device.

In some embodiments, a method for treating intervertebral disc degeneration or other defects in a spine includes rotating a dilating device having a distal threaded portion to dilate tissues enclosing a target site, advancing a retractor cannula device having direct visualization capability over the dilating device to the target site, wherein the cannula device contains at least one lumen configured to encase an endoscope, proximally withdrawing the dilating device, urging the retractor cannula into an open configuration to create a forward looking capability to enhance visualization and displacement of tissues, and introducing a therapy device into the retractor cannula device to treat disc degeneration or other defects.

In some embodiments, a method for treating intervertebral disc degeneration or other defects in a spine of a body includes making in incision into a skin of the body, introducing a dilating device having a distal threaded portion to a target tissue, dilating the target tissue by rotating the dilating device until the distal end of the dilating device passes through the target tissue, introducing a retractor cannula device having direct visualization component over the dilating device to a portion of the spine, proximally withdrawing the dilating device, urging the retractor cannula device into an open configuration to create a forward looking capability to enhance visualization and displacement of tissues, introducing therapy device into retractor cannula device to treat disc degeneration or other defects; and treating the disc degeneration or other defects.

Dilators with a threaded distal portion and direct visualization capability may be used for penetrating and dilating stiff tissues and bones are disclosed herein. The threaded portion of a dilator engages the tissue between the insertion site and the target site, and may be rotated for advancing through the target tissue in a more controlled fashion. The direct visualization capability may be used to visualize the ligament as the threaded distal portion passes through the ligamentum flavum.

In some embodiment, a method for dilating a target tissue may comprise introducing a dilating device having a distal threaded portion and an endoscope removably located in a longitudinal lumen of said dilating device, advancing the dilating device axially until the thread portion engages the target tissue, and rotating the dilating device while visualizing the target tissue using said endoscope until the distal end of the dilating device passes through the target tissue.

In some embodiments, a method for treating intervertebral disc degeneration or other defects in a spine may comprise introducing a dilating device having a distal threaded portion and an endoscope removably located in a longitudinal lumen of said dilating device, advancing the dilating device axially until the thread portion engages the ligamentum flavum, rotating said dilating device to dilate ligament enclosing the epidural space while visualizing the ligament using said endoscope until said dilating device passes through the ligament flavum, advancing a cannula device over the dilating device into the epidural space to a target site, proximally withdrawing the endoscope from the dilating device, proximally withdrawing the dilating device and, introducing a therapy device into said cannula device to treat disc degeneration or other defects.

BRIEF DESCRIPTION OF THE DRAWINGS

The embodiments herein are best understood from the following detailed description when read in conjunction with the accompanying drawings. It is emphasized that, according to common practice, the various features of the drawings may or may not be to-scale. On the contrary, the dimensions of the various features may be arbitrarily expanded or reduced for clarity. In some figures, the same reference numerals may be used to denote related structures in different embodiments or examples. Included in the drawings are the following figures:

FIGS. 4A and 4B are superior views of the duckbill retractor assembly; FIGS. 4C and 4D are side views of the duckbill retractor assembly in both the closed (dotted lines) and open (solid lines) configuration; and FIG. 4E is a perspective view.

DETAILED DESCRIPTION OF THE INVENTION

Conventional systems often rely on external visualization such as fluoroscopy and CT scanning for the approach to the disc, and thus lack any sort of real time, on-board visualization capabilities. Also, existing devices provide little in the form of tactile sensation for the surgeon and do not allow the surgeon to atraumatically manipulate surrounding tissue.

There is a need, therefore, for minimally invasive techniques and systems that provide the capability to diagnose or repair the spine using direct visualization while minimizing damage to surrounding anatomical structures and tissues. There is also a need for a method and device that allows a physician to effectively enter the epidural space of a patient, clear an area within the space to enhance visualization and use the visualization capability to diagnose and treat the disc injury.

The embodiments disclosed herein will be more clearly understood and appreciated with respect to the following Detailed Description, when considered in conjunction with the accompanying Drawings.

Figure 1:
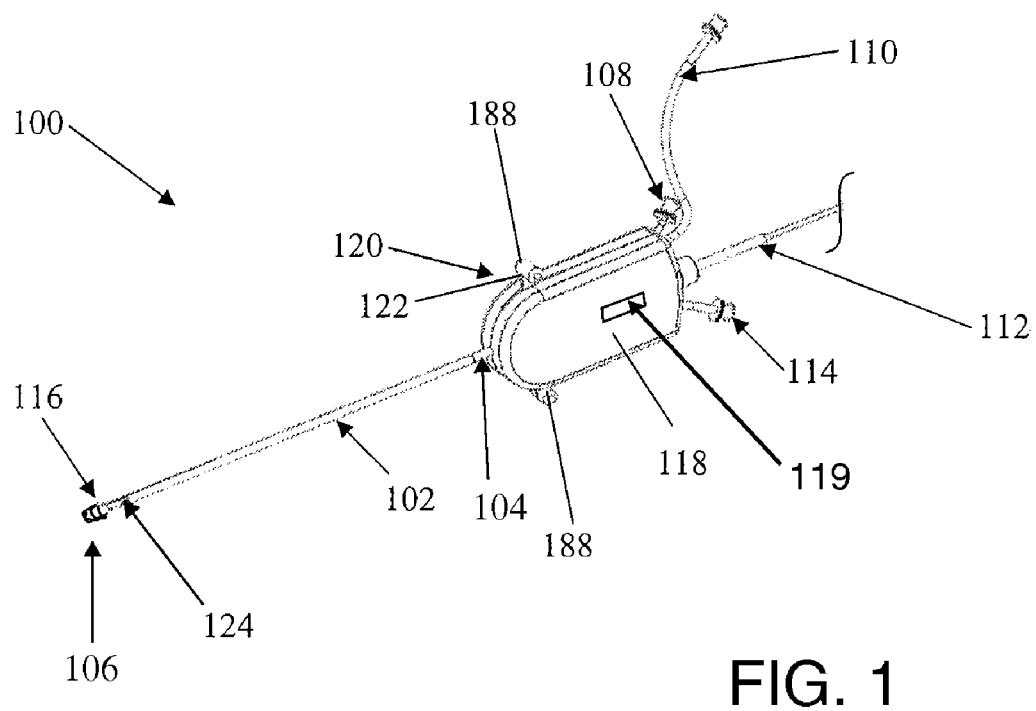
FIG. 1 is a perspective view of a retractor cannula device.
Figure 2:
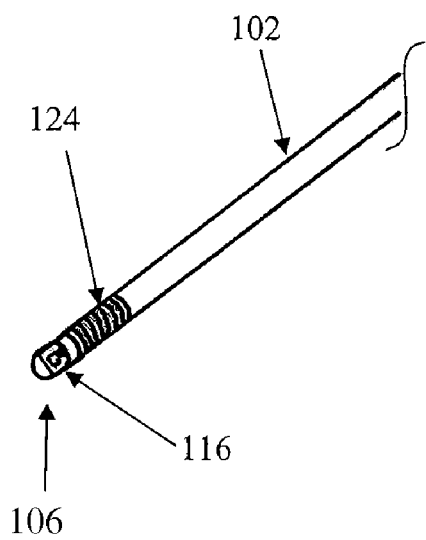
FIG. 2 is a perspective view of a distal portion of the retractor cannula device.

FIGS. 1 and 2 depict one embodiment of a retractor cannula device 100, which may comprise a tubular shaft 102 with a proximal end 104 and a distal end 106. In some embodiments, the tubular shaft 102. The proximal end of the shaft 102 may be associated with one or more ports 108, 110, 112, and 114, and the distal end 106 may be coupled to a retractor assembly 116 having two or more configurations, including an open configuration and a closed configuration. The distal end 106 may also comprise a bending region 124 that is configured to permit flexion of the distal end 106. The retractor assembly 116, examples of which are described in greater detail below, may be used to create working space by dissecting, deforming, manipulating, securing or atraumatically displacing surrounding tissue, structure, or anatomical features, for example. The atraumatic displacement of the surrounding structures from the distal end 106 may increase the angle of view of the surrounding structures from an endoscope or other viewing assembly located in the device 100, and may also improve the endoscope image by displacing structures a certain focal distance from the endoscope. In some embodiments, the retractor assembly 116 may be configured to allow a guide wire to be threaded through to facilitate navigation of the retractor cannula device to the targeted body region. Ports 108, 110, 112, and 114 may be configured for any of a variety of usages, including but not limited to infusion/drainage/ suction of fluids or materials, insertion/removal or supporting an endoscope or fiber-optic device, opening/closing of the retractor assembly, and for insertion/removal or support of other instruments or tools. An optional housing 118 or a handle structure may also be provided at the proximal end 104 of the shaft 102. The housing 118 may facilitate manipulation of the retractor cannula device by the user, in addition to optionally supporting the ports 108, 110, 112, and 114 and an optional steering mechanism 120 or steering assembly. The steering mechanism 120 may be manipulated using one or more actuators located on the housing 118. In the particular embodiment depicted in FIG. 1, the actuator comprises a lever 122 projecting from the housing 120, but in other embodiments, any of a variety of actuators may be provided. The lever 122 may have at least one end 188, or for example in FIG. 1, two ends 188. These and other components of the retractor cannula device 100 are described in greater detail below.

The shaft 102 of retractor cannula device 100 may comprise a rigid structure with a rigid material, such as stainless steel or rigid plastic. The bending region 124 may be made of any combination of flexible biocompatible polymers or pliable metals. The bending region 124 may be actuated by wires or struts within the shaft 102, for example, or by sliding other elongate members provided in the shaft 102. Alternatively or additionally, the shaft 102 may be made of strong, but flexible using a combination of materials, such as stainless steel metal braid embedded in elastic polymers. Examples of elastic polymers may be (but are not limited to) Pebax, polyurethane, and silicone.

Figure 3A:
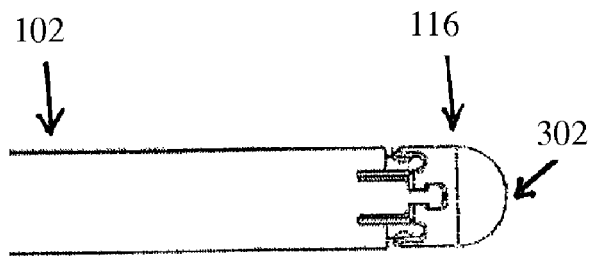
FIG. 3A is a superior view of a distal portion of the retractor cannula device.
Figure 3B:
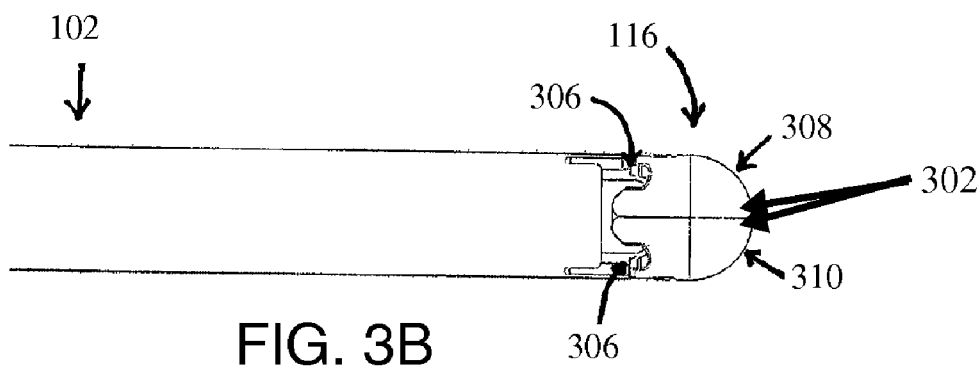
FIGS. 3B and 3C are side views of the distal portion of a retractor cannula device in a closed configuration and an open configuration, respectively.
Figure 3C:
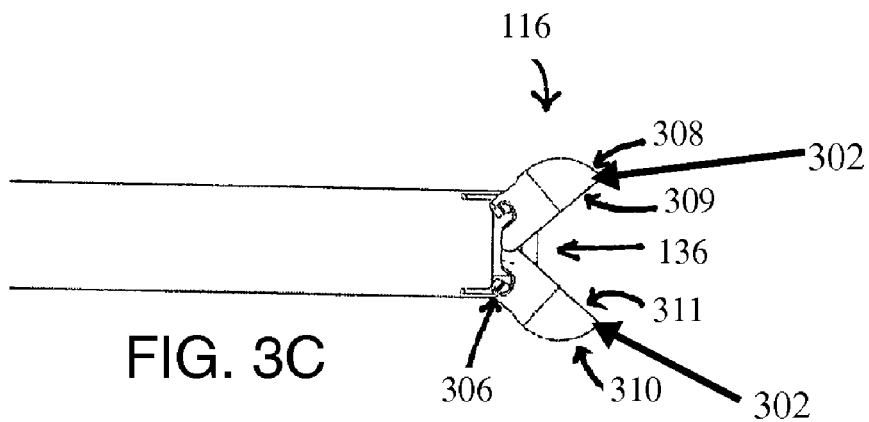

One embodiment of a retractor assembly 116 is shown in FIGS. 3A to 3E. The retractor assembly 116 may be a shape with curved surfaces, such as a dome or bullet shape, as shown in FIGS. 3A and 3B. Other shapes may include duckbill shapes, or any other shape that minimizes trauma to surrounding tissue may be used. In certain embodiments, the retractor assembly 116 may comprise at least one retractor element, such as a paddle, flap, or a jaw. A side view of retractor assembly 116 in a closed configuration is shown in FIG. 3B. The retractor assembly 116 may comprise two jaws 308 and 310, shaped such that when in the closed configuration, jaws 308 and 310 mate to form a substantially smooth round shape and a working space 136 is formed in between the two jaws 308 and 310. Although the jaws 308 and 310 in FIG. 3B are contacting each other around their outer edges when in the closed configuration, in other examples, the jaws may or may not fully close. It should be understood that the nose may comprise more than two retractor elements, including three or more retractor elements, that are shaped such that they form a smooth round shape in the closed configuration. The jaws 308 and 310 may be coupled to shaft 102 using a hinge mechanism 306. In certain embodiments, the hinges 306 may be living hinges and/or mechanical hinges formed by rivet, pins, or screws, for example. The hinges may be made of any suitable material. In some embodiments, the hinges 306 may lie flush against the outer surface of the shaft 102. The hinges 306 may be configured such that when the jaws 308 and 310 are transitioned into the open configuration, as shown in FIG. 3C, one or more distal points 302 of the jaws 308 and 310 may move away from the other or from the longitudinal axis of the device, exposing the working space 136. In one embodiment, as illustrated in FIG. 3C, the inner edges 309 and 311 of the jaws 308 and 310 forms an angle, and in the open configuration, this angle may be about 90 degrees. In other embodiments, the angle formed by inner edge 309 and inner edge 311 could be any value from about 1 to about 359 degrees, including about 60 degrees, about 90 degrees, about 120 degrees, about 180 degrees, or 270 degrees. Each jaw may be coupled to the shaft 102 via by one or more hinges 306 configured in any suitable way to expose or alter the working space 136 when transitioned between the closed configuration and the open configuration. In certain embodiments, the articulation between the shaft 102 and the jaws 308 and 310 may be configured to be slidable along the shaft 102 for additional maneuverability. Additionally or alternatively, the entire retractor assembly may be configured to be slidable along the shaft, with or with jaw angulation.

In certain embodiments, the mechanism that actuates the retractor assembly 116 may be biased towards one configuration or the other, or to a third configuration. For example, the jaws or retractor members may be biased towards a closed configuration, such that in the absence of an actuating force, the retractor assembly remains in the closed configuration, and assumes the open configuration when it is actuated. A retractor assembly with a bias towards the closed configuration may be used to manipulate and/or grab tissue, possibly for removal or replacement. In other embodiments, the retractor members may be biased towards an open configuration, such that in the absence of an actuating force, the retractor assembly remains in the open configuration, and assumes the closed configuration when actuated. A retractor assembly with a bias towards the open configuration may be used, for example, as a dilator or displace tissues or structures. A variety of bias mechanisms may be utilized as common in the art, for example, a spring may be used to maintain the retractor member(s) in a particular configuration, but forces may be applied to overcome the spring force and to transition the retractor member(s) to an alternate configuration. The spring or other bias member may act directly on one or more jaw members, or may act on the actuator located in the proximal housing of the device. Of course, certain embodiments may lack a bias to a configuration. In some embodiments, the retractor assembly may be releasably lockable into one or more configurations. For example, the jaws may be lockable in a variety of angled positions between their inner edges 309 and 311, from about 0 to about 180 degrees or more, including but not limited to about 60, about 90, about 120, about 180, or about 270 degrees. The movement range of each retractor member may be the same or different. In certain examples of retractor assemblies, one or more retractor member may have a fixed position, while one or more other retractor elements may be movable. For example, in reference to FIG. 3C, both jaws 308 and 310 are movable or pivotable to create an angle between the inner edges, however it should be understood that in other embodiments, either jaw may have a fixed position, while the other jaw is movable. For example, jaw 310 may be fixed in a given position, and jaw 308 may be pivoted about the hinge 306 to obtain a desired configuration.

The working space provided by the retractor assembly may be characterized with respect to the geometry and configuration of the retractor elements. In certain embodiments, the working space may be characterized as the aggregate space directly between any two regions of different retractor elements. The working space may vary depending upon the particular configuration. In some embodiments, the retractor assembly may characterized by the maximum working space achievable by the retractor assembly within its movement range. The actual working space and/or maximum working space of an instrument may be restricted or limited by the surrounding tissues or structures. One of skill in the art will understand that the working space or the maximum working space may or may not correlate with the maximum viewing ability provided the retractor assembly. For example, the working space when the jaws are about 180 degrees apart may be low, but the position of the jaws may substantially displace greater amounts of tissue away from the endoscope tip than the jaw angle which provides the maximum working space. Thus, in some instances, the effective viewing space may be bordered by the displaced and undisplaced tissues surrounding the distal end of the cannula device. In some embodiments, it should be understood that the working space may vary with the geometry of the retractor assembly 116. Alternatively or additionally, retractor assemblies with an elongate jaw configuration may dilate tissue more than retractor assemblies with a shorter jaw configuration.

As previously described, the retractor cannula device 100 may comprise at least one flexible region 124 to enable it to maneuver efficiency through tissue. In certain embodiments, the at least one flexible region may be situated distally on the outer shaft 102, proximal to the retractor assembly 116. This permits the tip of the retractor assembly cannula to flex, in additional to 360 degree rotation about its longitudinal axis. Such a configuration may permit the retractor cannula device to navigate to tortuous regions of the body, it would also allow the device to grip tissue and torsion tissue as necessary to re-position or remove it.

Figure 3D:
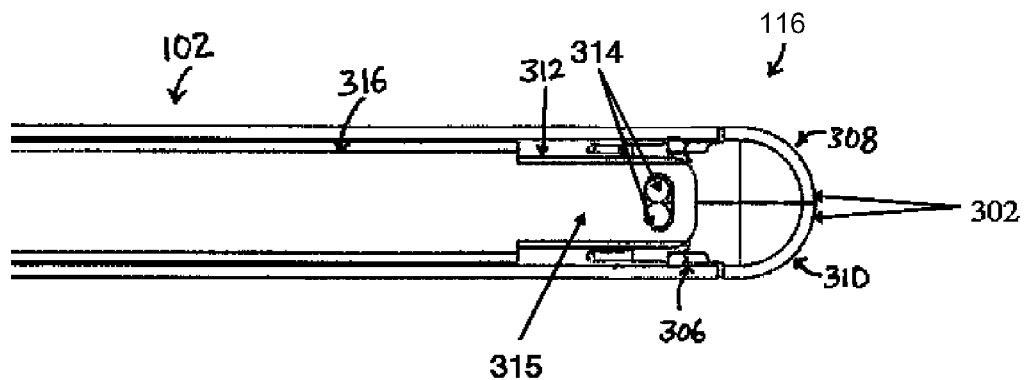
FIGS. 3D and 3E are cross-sectional and perspective ghosted views of the retractor cannula device in FIG. 3A.
Figure 3E:
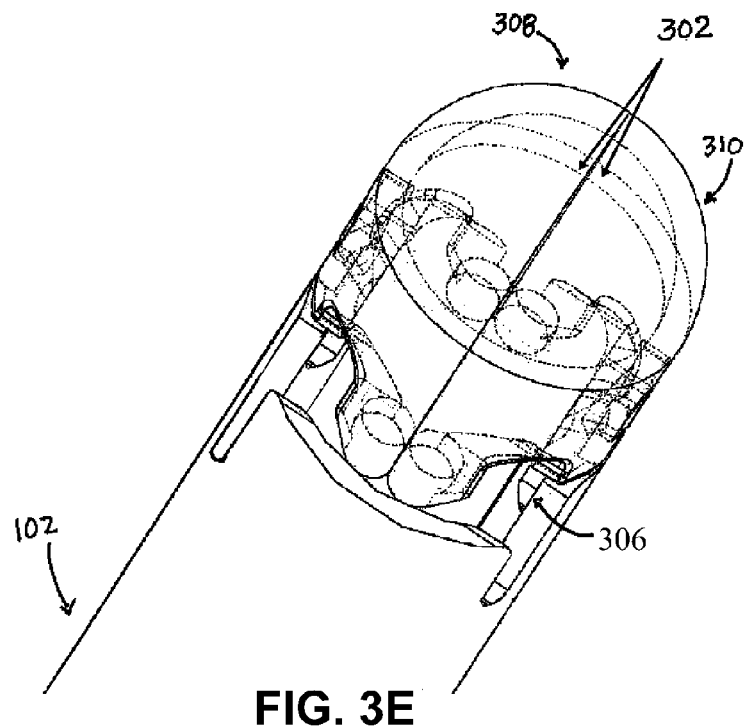

The rivet or axle of a mechanical hinge in the retractor cannula device may be made of metal or plastic, or other similar suitable materials. In addition to mechanical hinges that comprise a rivet upon which the hinged element rotates, some embodiments may utilize a living hinge. The living hinge may comprise any material that can be fashioned into a thin, flexible strip, which may comprise the same or different material as the instrument shaft, and may be a metal, plastic or other polymer. In other embodiments, other articulations may be used, including ball-and-socket joints. Referring to FIG. 3D, certain embodiments of a retractor cannula device may have an inner shaft 316 within shaft 102 that may act to support the structures that are used to navigate the retractor assembly and actuate jaws 308 and 310. The inner shaft 316 may be axially slidable to actuate the motion of the jaws 308 and 310. The lumen 312 of the outer shaft 102 may house at least a portion the jaw actuating mechanism. One example of a jaw actuating mechanism comprises an inner tube 316 within the lumen 312 of the outer shaft 102, wherein the tube 216 comprises perforated tabs 315 that articulate with pins 314 of the jaws 308 and 310. With the proximal position of the pins 314 relative to the hinges 306, by pushing the inner tube 316 distally, the jaws 308 and 310 pivot outwardly. By sliding or otherwise manipulating the in which may be pushed or pulled to translate the jaws 308 and 310 such that they rotate on hinges 306, and alter the angle between the jaws 308 and 310. Sliding of the inner shaft 316 may be controlled using a slider 119 provided on the housing 118. Other mechanisms may use other actuating mechanisms, including pull wires or struts, to open or close the jaws. The pull wires may include metallic or polymeric wires, which may be single-stranded or multi-stranded, and may included twisted or braided members. In still other examples, the movement of the jaws may be asymmetrical or one or more jaws may be immobile while one or more other jaws are movable.

Figure 4A:
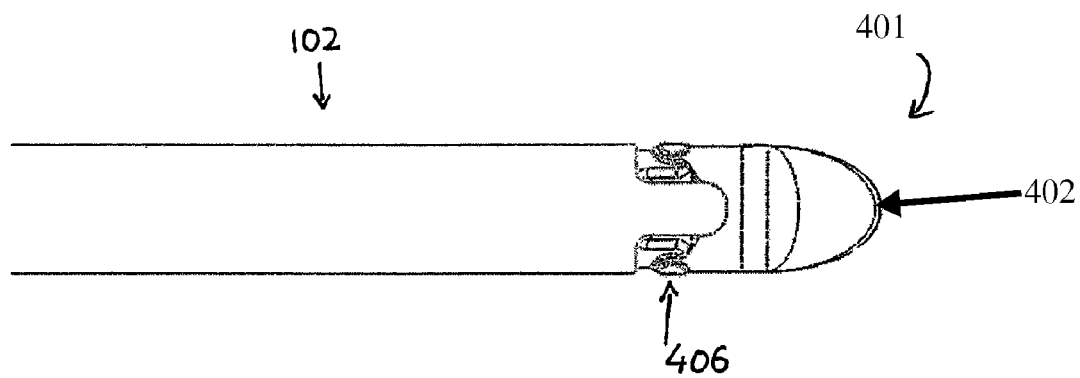
FIGS. 4A to 4E depict an embodiment of a retractor cannula device with a duckbill retractor assembly.
Figure 4B:
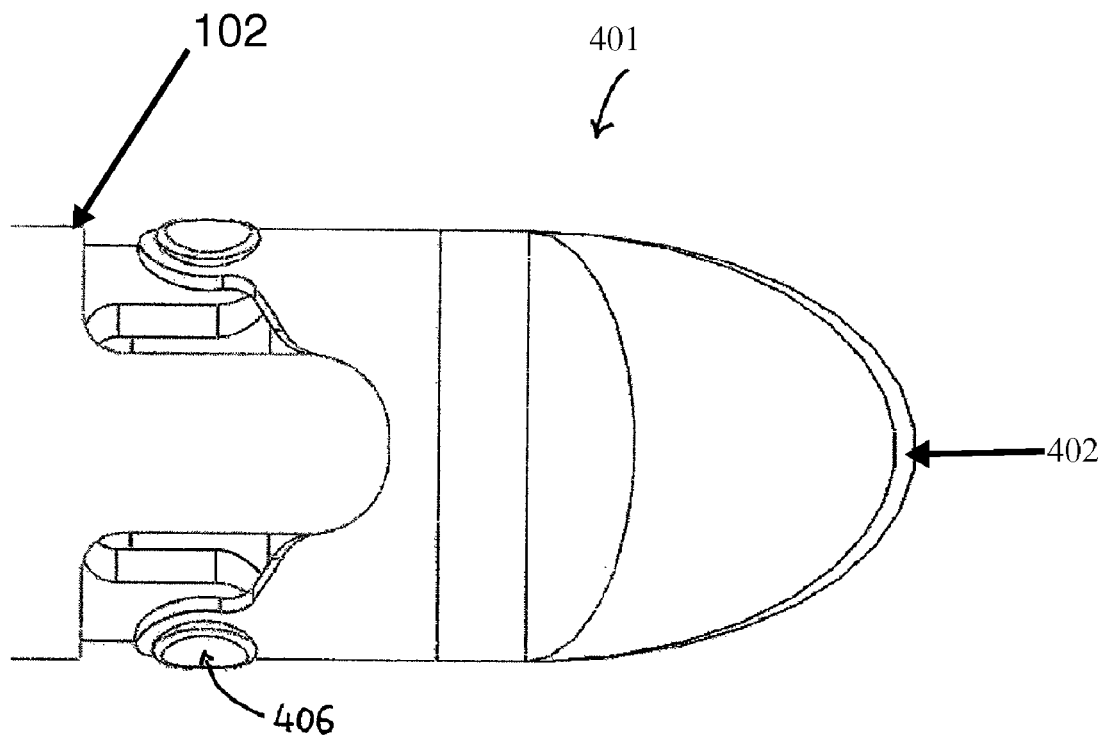
Figure 4C:
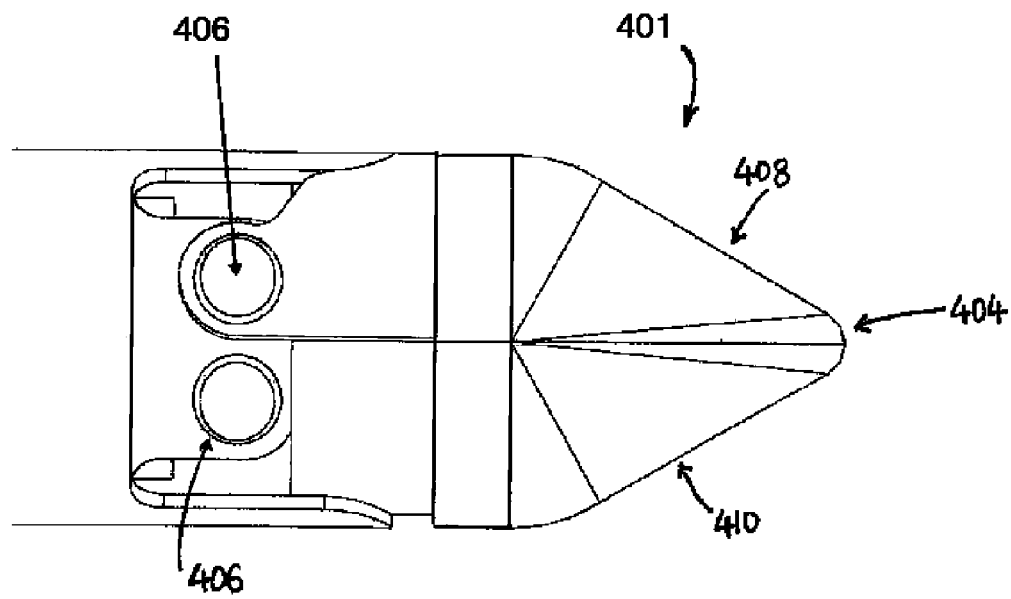
Figure 4D:
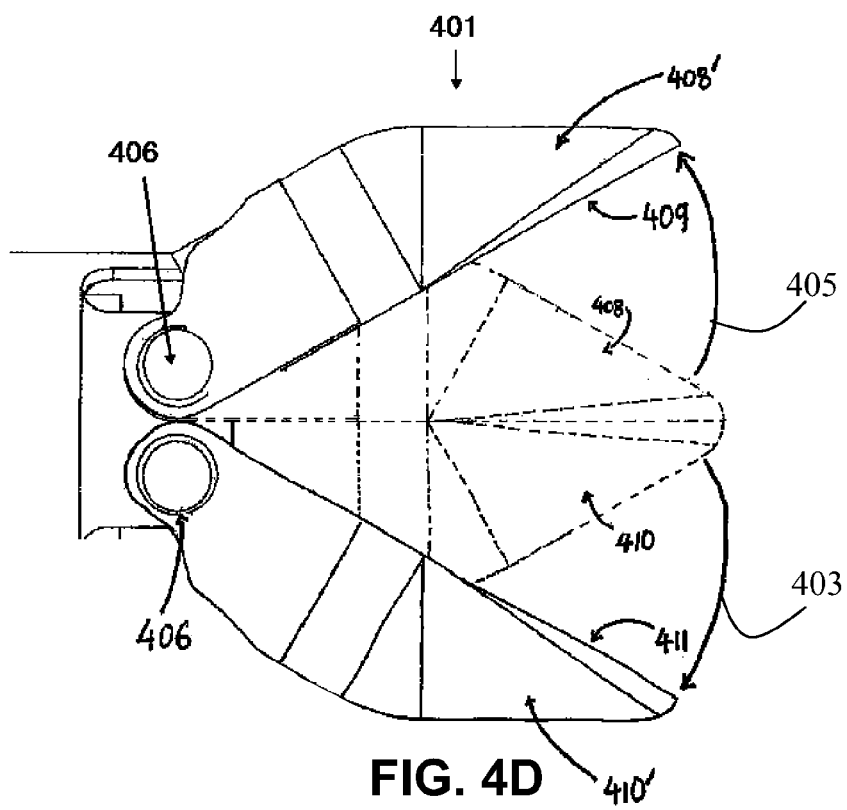
Figure 4E:
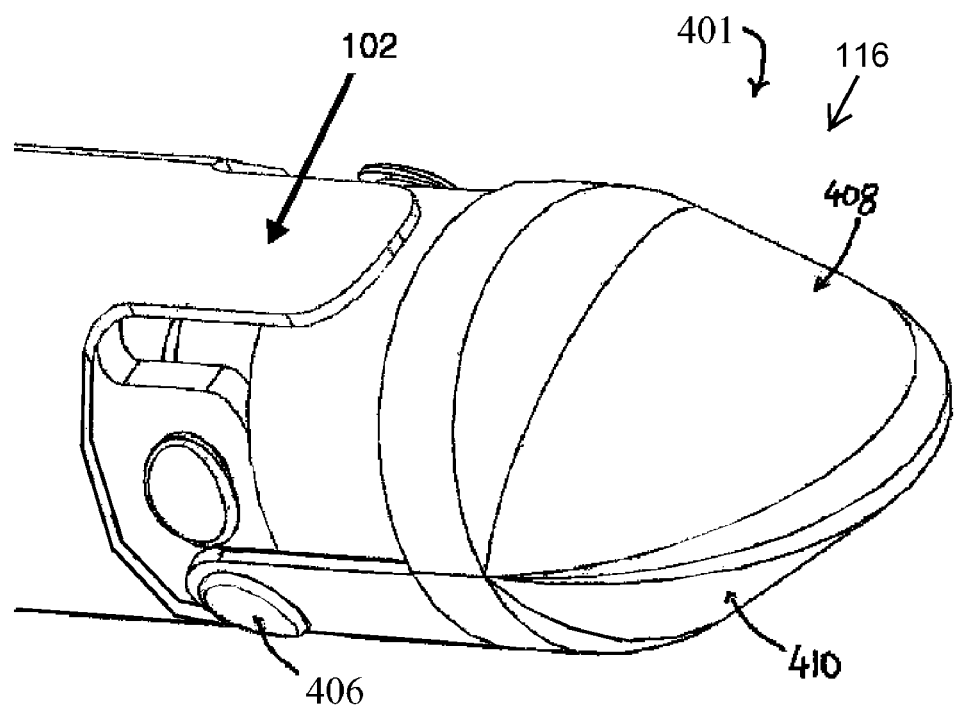
Figure 5A:
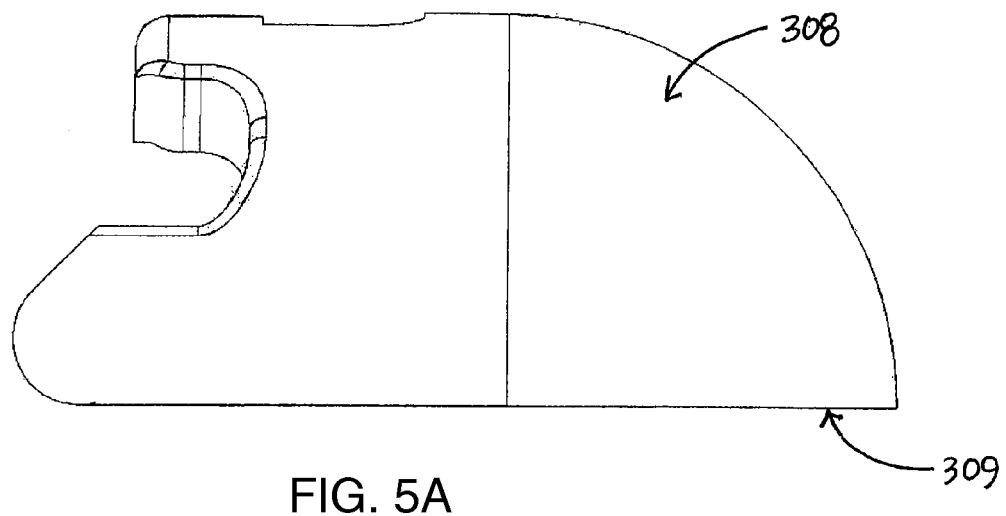
FIGS. 5A and 5B are component views of a dome and a duckbill shaped jaw, respectively.
Figure 5B:
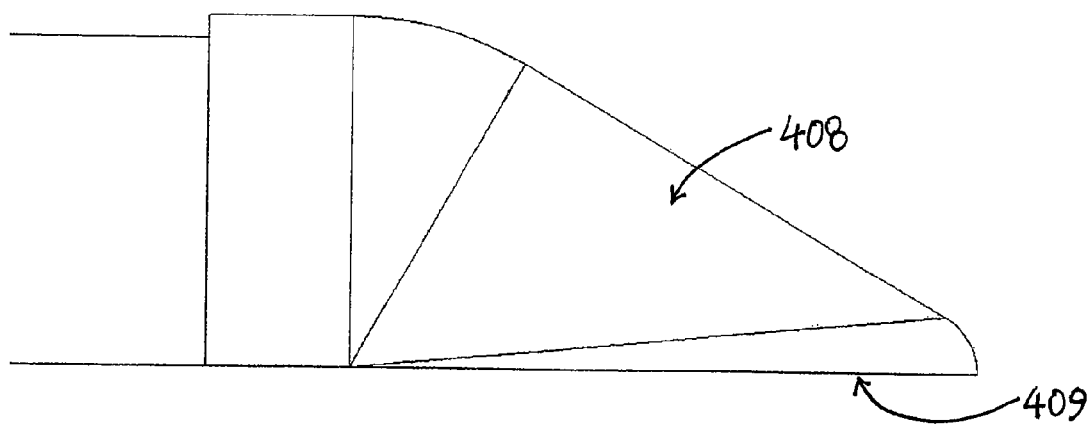

Another embodiment of a retractor assembly 401 is depicted in FIGS. 4A to 4E. As shown in the superior views in FIGS. 4A and 4B, the retractor assembly 401 comprises a generally smooth and rounded configuration on one profile where the taper is more gradual proximally and increases distally. As shown in a side view in FIG. 4C, however, the retractor assembly 401 has a more gradual or uniform taper along another profile that is perpendicular to the profile shown in FIGS. 4A and 4B. In other embodiments, the cross-sectional profile may be even flatter, with taper may be increased proximally but decreases distally. In other embodiments, any tapered or non-tapered configuration may be used. In this particular example, the retractor elements comprise jaws 408 and 410 that have a cross sectional profile with an acute angle, where the apices form a flat tapered tip 404 in the closed configuration, as shown in FIG. 4C. The open configuration is illustrated in the solid lines of FIG. 4D, showing the action of jaws 408 and 410, while the dotted lines represent the configuration of jaws 408 and 410 in the closed position. The jaws may be urged into the open configuration by rotating around hinges 406 in the direction of arrows 405 and 403, where an angle is created between the edges 409 and 411, and the jaws assume the open positions, marked as 408' and 410'. In the open configuration, the angle between edges 409 and 411 may be any value from about 0 degrees to about 270 degrees or more, including up to about 30 degrees, about 60 degrees, about 90 degrees, about 120 degrees, about 180 degrees, about 270 degrees, or more. As mentioned previously, in some embodiments, both jaws 408 and 410 need not open or close symmetrically, and in some embodiments, may even have a fixed configuration relative to the outer shaft 102. The actuating mechanism of the retractor assembly 401 may be the same or different from the actuating mechanisms disclosed for the retractor assembly depicted in FIGS. 3A to 3E. FIGS. 5A and 5B are side component views of the rounded jaw 308 and the duckbill jaw 408 to further illustrate the geometry and profile differences between the two configurations.

In certain embodiments of the retractor elements, the inner edge of the retractor elements may be configured with a variety of atraumatic and/or tissue-engaging features. In some embodiments, the edge 409 of the jaw 408 may comprise a smooth, rounded surface. In some instances, the edges 409 with smooth, rounded surfaces may reduce the risk of inadvertent snagging of tissue by the retractor assembly 401. In contrast, tissue-engaging structures or teeth 420 may be provided in the interior cavity 412 of the jaws 408. The inner location of the teeth 420 may reduce the risk of inadvertent tissue snagging while augmenting tissue engagement of tissues more likely intended for treatment by placement into the working space 136. The configurations of the tissue-engaging structures or teeth 420 may vary, and need not comprise pointed structures or sharp edged structures, for example.

Figure 5C:
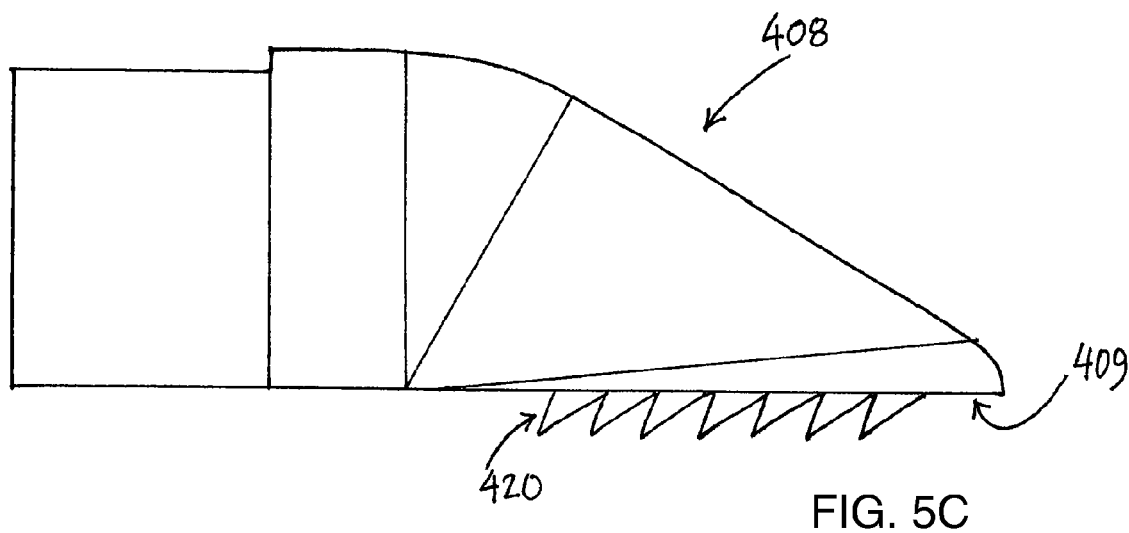
FIG. 5C illustrates an embodiment of a jaw member comprising teeth.
Figure 5D:
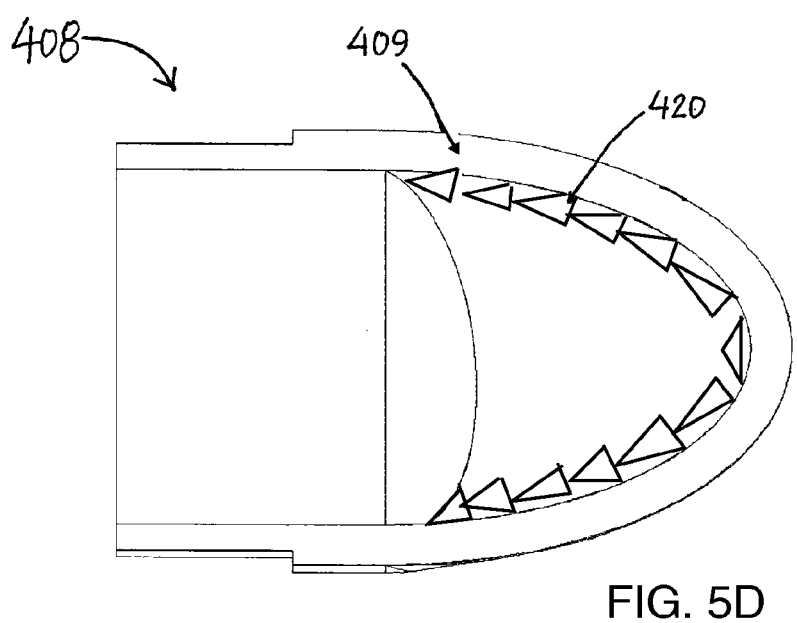
FIG. 5D is an inferior view of a jaw member.

In certain embodiments, the protrusions 420 may be angled with sharp/blunt vertices, as shown in FIG. 5C, but may be of any suitable geometry. Also, the protrusions 420 may be uniformly set at a slant to optimally secure tissue after initial contact, but it should be understood that the protrusions 420 may be set in alternate conformations, for example, protrusions may be non-uniformly set with different slants or no slants, and the protrusions may be of non-uniform shapes. The degree of protrusion of teeth may vary, with some protruding beyond edge 409 as shown in FIG. 5C, but in other embodiments, the tissue-engaging structures may be below the plane formed by the edge 409. The protrusions 420 may be made of the same material as the jaw 408, but may also be made of different materials. The protrusions on the inner edge of the retractor elements may be set a suitable distance away from the edge to limit trauma to surrounding tissue during the navigation of the retractor cannula device 100 towards the target region of the body. In some embodiments, the protrusions on the inner edge are set approximately about 0.1 mm to about 1 mm or more away from the edge 409. In some embodiments, the protrusions 420 are arranged along the perimeter of the inner edge 409, as represented by the circles in FIG. 5D which shows a bottom view of jaw 408, and/or may be arranged to tile a portion of the inner cavity of the jaw. It should be understood that any arrangement, and any density (which may or may not be homogeneous in the entire inner edge 409) of protrusions 420 may be used in the inner edge. Additionally or alternatively, other surface enhancements and coatings may be applied to the inner edge of the retractor elements and/or protrusions, such as hydrophilic or hydrophobic materials.

In certain embodiments, the retractor elements may be made of any transparent polymer, such as (but not limited to) polyester copolymers (PETG, PETE), nylon, urethane, polycarbonate, acrylic, and/or silicone. In some embodiments, the retractor elements may be made of an opaque material. Alternatively or additionally, the retractor elements may have a metal frame which may then be covered with one or more of the aforementioned polymers. The frame may be made of (but not limited to) stainless steel, titanium alloy, cobalt chromium, tungsten, tantalum. In certain embodiments, at least a portion of the retractor elements may be made of glass. Alternatively or additionally, the retractor elements may be constructed of radio opaque materials to allow visualization of the distal tip of sheath 102 in X-ray imaging. In other embodiments, the retractor elements include a marker or other feature(s) making all or a portion of the retractor elements perceptible using external imaging modalities. In another embodiment, the marker or feature is a radio opaque marker. Alternatively or additionally, the retractor elements may be constructed of materials that are readily resolved by ultrasound or other imaging modalities. In some embodiments, some portion of the jaw (e.g. distal/forward-looking portion) may be made of a soft material to minimize trauma to surrounding tissue.

Figure 6A:
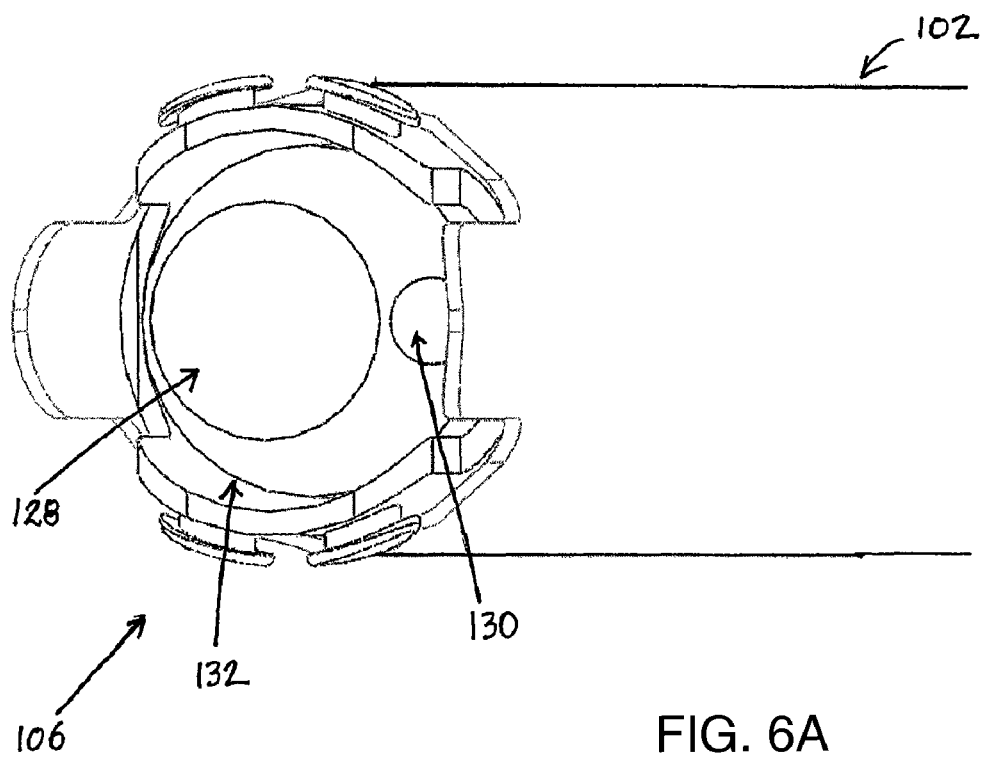
FIGS. 6A and 6B depict one embodiment of the working lumen within an instrument shaft.
Figure 6B:
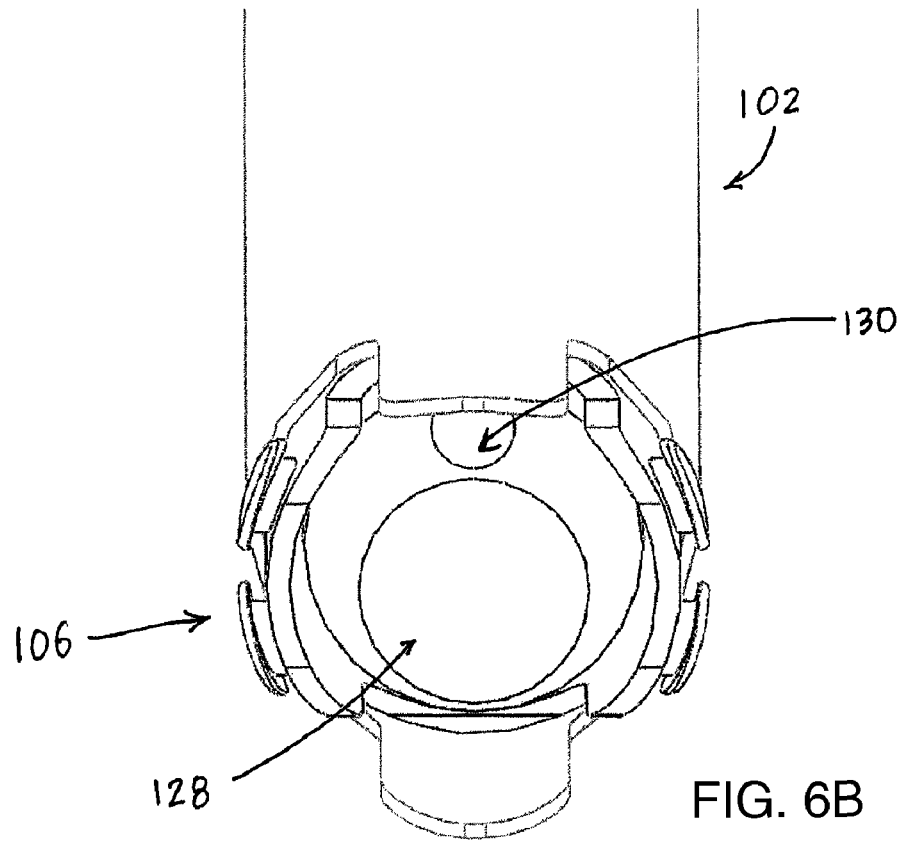

The shaft of the retractor cannula device may include one or more working channels. In FIGS. 6A and 6B, for example, the shaft 102 is depicted without the retractor elements to show the two channels 128 and 130 that open at the distal end 106 of the shaft 102. In other embodiments, however, the shaft may contain a different number of channels or channels with different positions, cross-sectional areas, or cross-sectional shapes, as shown in the examples in FIGS. 7A to 7C. Referring back to FIGS. 6A and 6B, one channel 128 may be used as a working channel for insertion of one or more instruments, and another channel 130 may be used as an endoscopy channel. One or more channels may have a longitudinal length that substantially spans the length of tubular shaft 102, but other channels may have a length shorter than the tubular shaft 102, and may terminate proximal to the distal end 106. Other channels may also be used, for example, to control bending or other movements of the cannula device. One or more channels may comprise a layer or coating to facilitate sliding of instruments within the channel, including PTFE and any of a variety of biocompatible lubricious coating materials. In some embodiments, the shaft may comprise a rigid or semi-rigid material, but in other embodiments, may comprise a flexible material.

Proximally, one or more of the lumens or channels 128, 130 and 132 of the tubular shaft 102 may be in communication with one or more ports 108, 110, 112 and 114. In the embodiment depicted in FIG. 1, for example, one of the channels 128 of the retractor cannula device 100 is in communication with an endoscopic port 114. Alternatively or additionally, channel 128 may also be in communication with an instrumentation port 112, and channel 130 may be in communication with an irrigation/aspiration port 108. In some embodiments, a separate irrigation port and aspiration port may be provided, which may permit simultaneous infusion and aspiration. Simultaneous infusion and aspiration may expedite clearing of the working field when compared to alternating infusion and aspiration using a single channel.

Figure 7A:
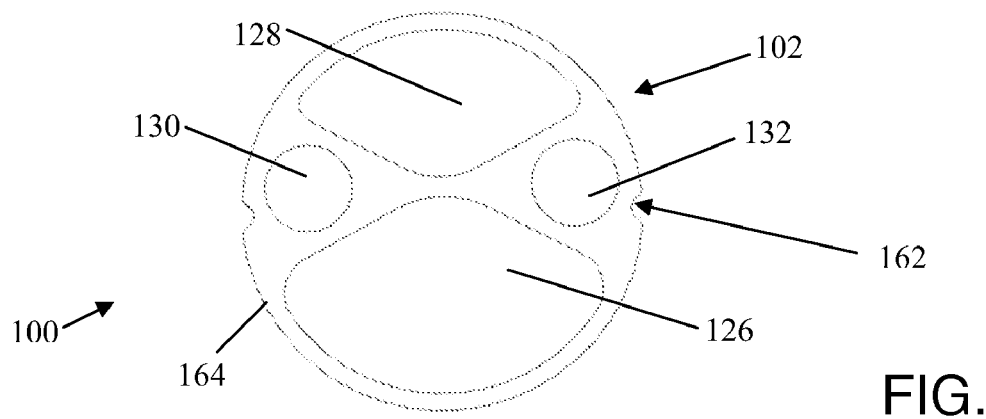
FIGS. 7A to 7C are cross-sectional views of various embodiments of a multi-lumen shaft.
Figure 7B:
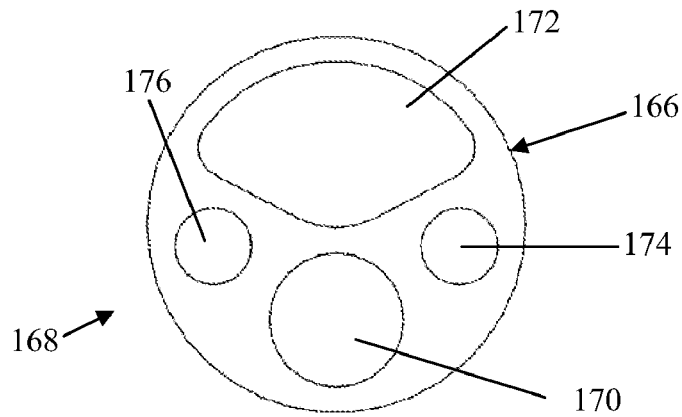
Figure 7C:
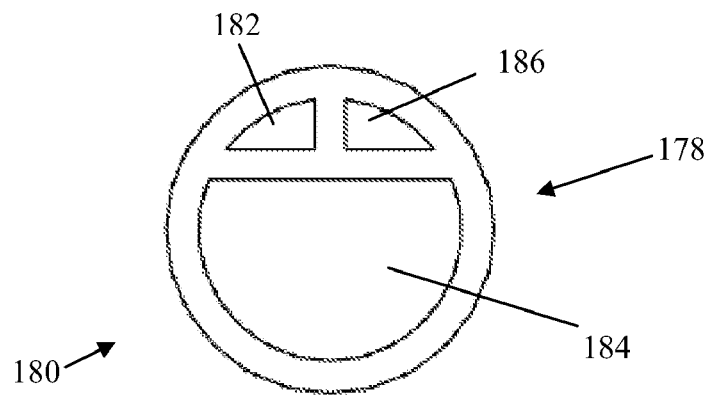

FIGS. 7A to 7C illustrate various embodiments of the retractor cannula device. In FIG. 7A, the retractor cannula device 100 may comprise a shaft 102 with a non-circular channel 128 configured to house a visualization device (such as, but not limited to, an endoscope), a non-circular working channel 126 which may be used to provide therapy device or as aspiration port, a retractor assembly actuator lumen 132, and additional port 130 for irrigation or aspiration. The shaft 102 may also optionally comprise one or more structures 162 on its outer surface 164. These structures 162 may comprise recessed or protruding configurations and may be used, for example, to maintain alignment with respect to introducer or guide member, or to reduce the amount of frictional resistance from any manipulation of the retractor cannula device 100. As depicted in FIG. 7B, the shaft 166 of the retractor cannula device 168 may have a non-circular visualization or irrigation port 170, a circular therapy device or aspiration port 172, a circular retractor assembly actuator lumen 174, and additional circular port 176 for additional irrigation or additional aspiration having a greater. As demonstrated in FIG. 7B, the circular ports 172, 174 and 176 need not have the same diameter. In FIG. 7C, the shaft 178 of the retractor cannula device 180 has a visualization or irrigation port 182, an injection port or therapy device or aspiration port 184, and a retractor assembly actuator lumen 186, wherein no port or lumen has a circular cross-sectional shape. It is contemplated that functions of various lumens in a cannula device may be suitably interchanged.

Referring back to FIGS. 6A and 6B, the visualization channel 128 may be used as a passage for insertion/removal of illumination, visualization, and/or imaging components to provide direct visualization capabilities at the distal end 106 of the retractor cannula device 100. In some embodiments, a visualization channel 128 may house or may be integrally formed with one or more illumination, visualization, analytical, and/or imaging components, including but not limited to one or more fiber-optic strands used to transmit light from a light source or to optically visualize the anatomy about the distal end 106 of the shaft 102.

As noted in the embodiment depicted in FIG. 1, the visualization channel 128 provides access to the target area for endoscopic imaging and/or medical imaging components. The retractor elements of the retractor assembly 116 in the open configuration may act as dilators or retractors to permit a wider field of view. For example, the retractor cannula device may first assume a closed configuration in order to atraumatically navigate towards the target body region. Once the distal end of the shaft has reached the target area, the retractor assembly 116 can be transitioned to the open configuration, dilating the surrounding tissue and enabling an endoscope positioned in visualization channel 128 to visually access the target tissue. In some embodiments, the retractor elements of the retractor assembly may be made of a transparent material, so that even in the closed configuration, the endoscope residing in visualization channel 128 may have visual access to the surrounding tissue, and may allow the endoscope to be used to provide visual cues to navigate the distal tip of the cannula to the desired location.

In some embodiments, the visualization channel 128 may be augmented by changes to the geometry and/or movement of the retractor assembly 116. For example, some retractor assemblies may have hinge mechanisms that allow the retractor elements or jaws to form an angle greater than about 90 degrees or greater than about 180 degrees. In other examples, retractor assemblies may have different longitudinal lengths relative to their articulation points. For example, some retractor assemblies may have a retraction member with a length of at least about 1 mm, about 2 mm, about 3 mm, about 4 mm, about 5 mm, about 6 mm or more from its articulation point with the shaft. The longitudinal lengths of each retractor member may be the same or different. The retractor cannula device used may be selected depending upon the region of the body in which the retractor cannula device has been deployed. In regions with large cavities, a bullet-shaped retractor assembly may be used to reduce the trauma to surrounding tissue without compromising the field of view. In regions where tissue is more densely compacted or folded, a duckbill-shaped retractor assembly may be used because the tapered shape of the closed configuration would allow it to maneuver into folds, and upon transitioning into the open configuration, substantially dilate the tissue to allow for a larger field of view and working space. In other examples, multiple retractor cannula devices with different configurations may be used during at the same target site.

Embodiments of the retractor cannula device 100 may facilitate the positioning of an instrument in a targeted area. For example, the instrument may be steered using information, such imaging or physiological information, provided by the instrument. The image may come from a fiber optic line or bundle, or a data device such as a camera placed on the distal end of the instrument, or from a sensor or combination of sensors. In one embodiment, the sensor utilizes light to generate the image. In another embodiment, the sensor is adapted to see through the bloody field as presented in the spinal region by selecting at least one infrared wavelength transparent to blood or other bodily fluids. In some embodiments, at least one infrared wavelength transparent to blood presented in the spinal field may have a wavelength of about 1 micron to about 15 microns. In another embodiment, the at least one infrared wavelength transparent to blood presented in the spinal field has a wavelength between about 1.5 micron to about 6 microns. In yet another embodiment, the at least one infrared wavelength transparent to blood presented in the spinal field has a wavelength between about 6 microns to about 15 microns. In yet another embodiment, the at least one infrared wavelength transparent to blood presented in the spinal field has a wavelength between about 1.0 microns to about 1.5 microns, about 1.5 microns to about 1.9 microns, about 2.0 microns to about 2.4 microns, about 3.7 microns to about 4.3 microns, or about 4.6 microns to about 5.4 microns. In yet another embodiment, the wavelength is selected or adapted for use in distinguishing nervous tissue from surrounding tissue and/or minimally vascularized nervous tissue. In yet another embodiment, the wavelength is selected to distinguish nervous tissue from muscle. Wavelength selection information and characterization and other details related to infrared endoscopy are found in U.S. Pat. No. 6,178,346; US Patent Application Publication No. 2005/0014995, and US Patent Application Publication No. 2005/0020914, each of which is hereby incorporated by reference in its entirety.

The visualization channel 128 or the distal end 106 of the device 100 may include a sensor used to generate images or identify tissue or tissue characteristics. In one example, the sensor utilizes acoustic energy to generate the image, similar to diagnostic ultrasound. In another example, the sensor utilizes an electrical characteristic to generate the image or other types of structural or physiological information. In yet another example, the sensor distinguishes the type of tissue adjacent to the sensor. Some properties used by the sensor to differentiate adjacent structures or tissue include resistance, capacitance, impedance, membrane voltage, acoustic, and optical characteristic of tissue adjacent the sensor or probe. Additionally, the sensor or image may be used to distinguish different types of tissue to identify neurological tissue, collagen, or portions of the annulus, for example. It is to be appreciated that the sensor may be a multi-modal or multi-sensor probe that can distinguish bone, muscle, nerve tissue, fat, etc. to help position the probe in the proper place.

In some embodiments, a trocar may be guided using fluoroscopic or other external imaging modality to place the trocar in proximity to a treatment area. In contrast to conventional procedures that attempt to fluoroscopically navigate a trocar tip around nerves and other tissue, the trocar may remain safely positioned away from sensitive structures and features. In one embodiment, the trocar tip remains about 1 to about 2 cm or more from vulnerable nerve tissue. In another embodiment, the last about 1 to about 2 cm of travel to a therapy site is performed using direct visualization provided by a visualization mechanism in the retractor cannula device.

In some embodiments, the trocar is removed and the retractor cannula device 100 is inserted into the pathway formed by the trocar. In other embodiments, a tubular trocar may be used. From the final trocar position, the retractor cannula device 100 may be passed through a channel or lumen of the trocar and along the remaining distance to the therapy or treatment site using the onboard visualization capabilities. The onboard visualization may be used alone or in combination with the retractor assembly 116 or other type of atraumatic tip to identify, atraumatically displace, and/or maneuver around nerves and other tissue as needed. An optional steering mechanism may be provided on the retractor cannula device 100 to manipulate surrounding tissue and structures, and/or to traverse the remaining distance to one or more therapy or treatment sites. In other embodiments, the retractor cannula device 100 may have a rigid or fixed configuration, and may be manipulated by optionally manipulating the trocar to reach a desired location. In an alternative embodiment, the trocar may house the retractor cannula device during trocar insertion and thus utilize the direct visualization capabilities of the visualization mechanism within the retractor cannula device to guide trocar positioning. In still another embodiment, the trocar may be provided with a separate imaging system from the imaging device or component provided in the retractor cannula device for use during trocar insertion. In still another embodiment, the trocar may be configured with a lumen to house only the imaging component from the retractor cannula device 100. After the desired trocar position is reached, the trocar is removed and the imaging component is removed from the trocar and reinserted into the retractor cannula device 100. In yet another alternative embodiment, both external imaging may be used to position the trocar distal end, either alone or in combination with direct imaging.

As mentioned previously, one or more embodiments of the retractor cannula device may be provided with any of a wide variety of steering configurations, such as the steering mechanism 120 depicted in FIG. 1. In one embodiment, the retractor cannula device 100 is steerable in one or more axes, including a device with two axes. In some embodiments, one axis may be a rotation axis. In another embodiment, the retractor cannula device is non-steerable. In yet another alternative embodiment, the retractor cannula device may be pre-formed into a shape that is adapted to access a portion of the spinal region or other region of the body. The shape may include any of a variety of angled and/or curved segments to access a particular body site. In yet another embodiment, the retractor cannula device is situated within the trocar in such a way that the retractor cannula may have steering capability up to about 360° inside the spinal space. The steering mechanism 120 may include one or more flexible bodies or flex regions 124 on the retractor cannula device 100. The flexible body may be bent by manipulating a control such as lever 122 located on the housing 118. Various examples of the steering mechanism and the flex region 124 and are described in greater detail below.

The dimensions of the retractor cannula device may be sized and selected based on the particular therapy being provided. For example, one embodiment of the retractor cannula device may be dimensioned for navigation to a spinal region for diagnostic evaluation and/or to apply a therapy thereto. In another embodiment, the retractor cannula device may be sized to fit within the epidural space. Other embodiments may be configured for use in the chest cavity (e.g. pleural biopsy or pleuracentesis) or abdominal-pelvic cavity (e.g. bladder neck suspension), or for non-spinal procedures such as breast biopsy and transvaginal oocyte retrieval, for example. In some embodiments, the retractor cannula device 100 may have a diameter of about 5 mm or less, while in other embodiments, the diameter may have a diameter of about 3 mm or less, or even 2.5 mm or less. In another embodiment, one or more of the working channels 126 and 128 of the retractor cannula device 100 may have a diameter of about 5 mm or less, about 3 mm or less, about 2 mm or less, about 1 mm or less, or about 0.8 mm or less.

As mentioned previously, the cannula device may comprise a retractor assembly or other type of structure that may be used as an atraumatic tip structure to reduce the risk of inadvertent injury to surrounding structures during a procedure. The atraumatic tip may be configured to provide tactile feedback to the user of the rigidity, pliability or feel of the tissue or structures in contact with the tip. In one embodiment, the atraumatic tip also provides dissection or retraction capabilities and/or the ability to displace surrounding tissue. The overall shape of the atraumatic tip may allow manipulation of the nerves as the retractor cannula device is advanced without harming the nerve or causing pain. In one embodiment, the atraumatic tip may have a curved shape and no sharp edges, burrs or other features that may pierce, snag, tear or otherwise harm tissue that comes into contact with the atraumatic tip. The shape, surface contours and/or overall finish of the atraumatic tip may be selected to reduce or minimize impact forces when the tip comes into contact with structures such as nerves, muscle and the spinal dura, among others.

As mentioned previously, the atraumatic tip may also be controllably pivoted or actuated from the closed configuration to the open configuration, or otherwise comprise two or more surfaces or structures that are independently controllable. The tip may be a retractor assembly that is urged from the closed to open configuration to create a working space in the surrounding tissue as well as provide a clearing for improved visibility. The retractor cannula device may then be advanced into the working space. The retractor assembly may be actuated to the open configuration again to create another working space and so forth to advance the retractor cannula device in a spinal space. In addition, the retractor cannula device may be used to provide saline or another type of cleaning solution to the working area for enhancing visualization. In another embodiment, the distal retractor assembly 116 may be movable or articulated such that it may be used to displace surrounding tissue or structures. The displacement of tissue or structures may be felt by the user and may provide a more tactile sense of tissue movement. The tissue displacement may result from active movement of the tip under control of the user, movement caused by releasing the tip from a bias position or from other conventional techniques for manipulation of surgical implements.

Embodiments of the atraumatic retractor assembly 116 may also be used to assist with or perform therapy or treatment, shield surrounding tissue or provide access for other devices. The atraumatic retractor assembly 116 may be positioned at the surgical or treatment site in a compact or stowed condition (see, e.g., FIG. 3B) and then deployed according to the type of device used (see e.g., FIG. 3C).

The atraumatic retractor assembly 116 may be used to manipulate surrounding tissue in one or more ways. First, by transitioning the retractor assembly 116 from a closed to an open configuration, the jaws 408 and 410 of the retractor assembly 116 will be urged outward against the surrounding tissue. Second, whether or not the device 100 is deployed or stowed, the retractor cannula device 100 may be maneuvered using the steering mechanism 120 to manipulate tissue. Third, the atraumatic retractor assembly 116 may cycled between the closed and open configuration to assist in the advancement of the steerable retractor cannula device 100. For example, the retractor assembly 116 may be closed to facilitate insertion of the device 100 through a wall of tissue, and may be opened after traversing the wall. Fourth, the practitioner may advance the retractor cannula device 100 and manipulate surrounding tissue and push tissue away by creating space under direct visualization. As the retractor assembly 116 of the retractor cannula device 100 expands its jaws from a closed to open configuration, a work space or opening may be created in the surrounding tissue, thereby easing the advancement or atraumatic maneuverability of the retractor cannula device 100. Thereafter, the atraumatic retractor assembly 116 may be deployed or otherwise used to deform surrounding tissue and/or to make space available for the retractor cannula device 100 or other therapy or treatment device provided by working channel 126 (e.g., FIG. 7A). It is contemplated that one or more of these methods may be used in combination to manipulate the surrounding tissue. Any of a variety of other methods for utilizing the retractor cannula device 100 are also contemplated.

The atraumatic retractor assembly 116 may also include working channels to further assist in performing procedures. The retractor assembly 116 is capable of both closed and open configurations and is illustrated in a deployed configuration in FIGS. 3C and 4D. The access lumens 126, 128, and 130 may run the length of the device 100 and may be sized to allow passage of the catheters, endoscopes, and instruments/devices, respectively.

The distal segment or tip 404 in FIG. 4C may be selected from a material that is transparent to the operation of the port components, such as the visualization channel. In some embodiments, the atraumatic tip 404 may be formed from rigid, clear plastic, while in other embodiments, the atraumatic tip may comprise a flexible, deformable material. In some embodiments, the tip comprises an opaque material, but in other embodiments may be translucent or transparent, which may facilitate the visualization of the tissue or structures adjacent the tip. The tip material may be stainless steel, cobalt chromium, titanium, nickel-titanium, polycarbonate, acrylic, nylon, PEEK, PEK, PEKK, PEKEK, PEI, PES, FEP, PTFE, polyurethane, polyester, polyethylene, polyolefin, polypropylene, glass, diamond, quartz, or combination thereof, for example. In some embodiments, the tip materials may include the addition of one or more radiographic markers or materials.

In other embodiments, the retractor assembly or an extendable structure may be provided with one or more support elements. The support elements may be oriented longitudinally, radially, and/or circumferentially along the retractor assembly jaws to support the various conformations the jaws may take on. The configuration of a support element may be complementary to the shape or configuration of the retractor assembly. In one embodiment, the support element may comprise a helical configuration, for example. In some embodiments, the support elements may be located about the shaft 102 lumen. The support elements may comprise any of a variety of materials, including but not limited to a metal and/or polymeric material. The support element maybe rigid, semi-rigid or flexible, and at least a portion of the support element may be attached or coupled to the shaft, the inner or outer surface of the retractor assembly, and/or embedded in the inner edges of the retractor assembly.

Although the retractor assembly 116 may be generally symmetrical about the longitudinal axis of the shaft 102, in other embodiments, the retractor assembly may be asymmetrical. Other retractor assembly jaw configurations may also be used, and slits or windows may be optionally provided to increase visualization. For example, the retractor assembly configuration may be altered using different jaw shapes, variable wall thickness and/or by pre-forming curves or fold along one or more regions of the jaw material. In certain embodiments, the retractor assembly may have small apertures, such as slits, near the distal tip to allow for irrigation or administration of therapeutic agents to the target site.

Referring back to FIG. 7A, the tubular shaft of the retractor cannula device 100 may include a visualization channel 128, a larger working channel 126, and an additional irrigation/aspiration port 130. The channels and/or ports of the retractor cannula device 100 may be configured to accept wide variety of therapy devices suited to the type of therapy being performed. The therapy device may be configured and used to apply energy to surrounding tissue. The therapy device may also be a surgical instrument used to cut, pierce or remove tissue. Moreover, it is to be appreciated that the therapy device may be any conventional endoscopic instrument. The therapy device may include ultrasonic devices, motor driven devices, laser-based devices, RF energy devices, thermal energy devices, cryotherapy-based devices, or other devices selected based on the spinal therapy being performed. For example, the therapy device may also be a mechanical device adapted to remove tissue such as a debrider or an aspirator. Other examples are described in greater detail below. Moreover, it is to be appreciated that the retractor cannula device 100 may be used to inject pharmacological agents into the spinal area. The size, number and arrangement of the working channels are readily adaptable for different configurations, depending upon the type of procedures performed. A greater or a fewer number of working channels may be provided, and the working channels need not have the same size and shape. In addition, the working channels may also be configured to perform auxiliary functions. In one example the channels or ports may be used to provide irrigation to assist in tissue dissection as the atraumatic tip is advanced in the spinal space. An irrigating working channel may be in communication proximally with a fluid source, such as a syringe or intravenous infusion system, and in communication distally with the distal end of the retractor cannula device so that the fluid exiting the irrigation working channel is directed to the distal portion of the retractor cannula device. In another example, the irrigation working channel or another working channel may be used to rinse the atraumatic tip or keep clear other portions of the retractor cannula tool. In the particular embodiment depicted in FIG. 7A, the working channel 126 and the visualization port 128 are configured with non-circular cross-sectional shapes. In some embodiments, the non-circular shape permits the placement of an instrument with a circular cross-sectional shape within the channel or port while providing still providing flow paths for fluids and material through the channel 126 and the port 128. Shared or eccentric flow paths along non-circular shaft channels and ports may also otherwise take advantage of unused sections of the cannula shaft. Unlike shafts with only circular channels or ports, the flow paths may be provided without having to increase the overall cross-sectional area of the cannula shaft. Channels or ports having non-circular cross-sectional shapes may also be used with instruments having a complementary non-circular cross-sectional shape. For example, complementary non-circular cross-sectional shapes may be used to control or limit the amount of instrumentation rotation within the channel or port.

During use, the retractor cannula device may be moved or may remain in place while an inserted therapy device is manipulated to perform the desired function. Once the working or therapy area has been created or accessed using the atraumatic retractor assembly, the atraumatic retractor assembly may be removed thereby allowing working channel or trocar or introducer to be used for another instrument or therapy device or to provide support for a procedure. For example, the therapy device may comprise a mechanical debrider or other type of tissue disrupting device that may be introduced via the working channel to assist in removal of tissue. Various examples of mechanical tissue disrupting devices that may be used with a retractor cannula device are described in U.S. patent Ser. No. 12/035,323, filed Feb. 21, 2008, which was previously by incorporated by reference in its entirety. In yet another example of the flexibility of the retractor cannula device, one or more the working channels or ports may be used to provide access for the delivery of pharmacological agents to the access site either for application onto or injection into tissue. In some embodiments, the therapeutic agents may be directed injected into the channel or port, but in other embodiments, an infusion catheter may be inserted into a channel or port and used to provide additional control of the therapy. The infusion catheter may have any of a variety of configurations and features, including but not limited to its own optional steering mechanism separate from the retractor cannula device, and a needle tip for injecting therapeutic agents into the tissues or structures. In some embodiments, the needle tip may be retractable and extendable to protect against inadvertent puncture of the tissues or structures accessible from the retractor cannula device. Examples of injection catheters that may be used with embodiments of the retractor cannula device include U.S. patent Ser. No. 10/820,183, which is hereby incorporated by reference in its entirety.

The therapy device may be supplied with energy from a source external using a suitable transmission mode. For example, laser energy may be generated external to the body and then transmitted by optical fibers for delivery via an appropriate therapy device. Alternately, the therapy device may generate or convert energy at the therapy site, for example electric current from an external source carried to a resistive heating element within the therapy device. If energy is supplied to the therapy device, transmission of energy may be through any energy transmission means, such as wire, lumen, thermal conductor, or fiber-optic strand. Additionally, the therapy device may deliver electromagnetic energy, including but not limited to radio waves, microwaves, infrared light, visible light, and ultraviolet light. The electromagnetic energy may be in incoherent or laser form. The energy in laser form may be collimated or defocused. The energy delivered to a disc may also be electric current, ultrasound waves, or thermal energy from a heating element. Moreover, it is to be appreciated that embodiments of the retractor cannula devices described herein may also be used to dispense a compound, compounds or other pharmacological agents to reduce, diminish or minimize epidural neural tissue scarring.

The retractor cannula device may also be used to perform denervation procedures using direct visualization from the retractor cannula device. The denervation procedure may be physical, chemical or electrical denervation, for example. The approaches used may be similar those described herein to access the posterior or posterolateral annulus. It is to be appreciated that the denervation procedures may be performed to relieve discogenic pain and/or before the disc damage has progressed to a herniated disc or torn annulus.

Referring back to FIG. 1, as noted previously this embodiment of a retractor cannula device 100 further comprises a steering mechanism 120. During use, the retractor cannula device 100 may be advanced through the working channel of a trocar or introducer and into the working area. In some embodiments, the working area or space may be created by separating structures or tissue using the atraumatic retractor assembly 116, either alone or in combination with the steering mechanism 120. The steering mechanism 120 may be configured to provide any of a variety of steering features, including various bending planes, various bending ranges, extension and retraction ranges, and rotations ranges, for example. As mentioned previously, in the embodiment depicted in FIG. 1, the actuator comprises a lever 122 with both ends 188 projecting from the housing 118, but in other embodiments, any of a variety of actuators and actuator configurations may be used, including but not limited to dials, knobs, sliders, buttons and the like, as well as electronic touch controls, for example. In some embodiments, only one end 188 of the lever 122 may project from the housing 118. The controls used to manipulate the steering mechanism 120 may be manually manipulated by the user or by a mechanical control system comprising various motors. In still other embodiments, actuators such as the lever 122 may be omitted and the retractor cannula device 100 may be directly coupled to a motor control system.

Figure 8:
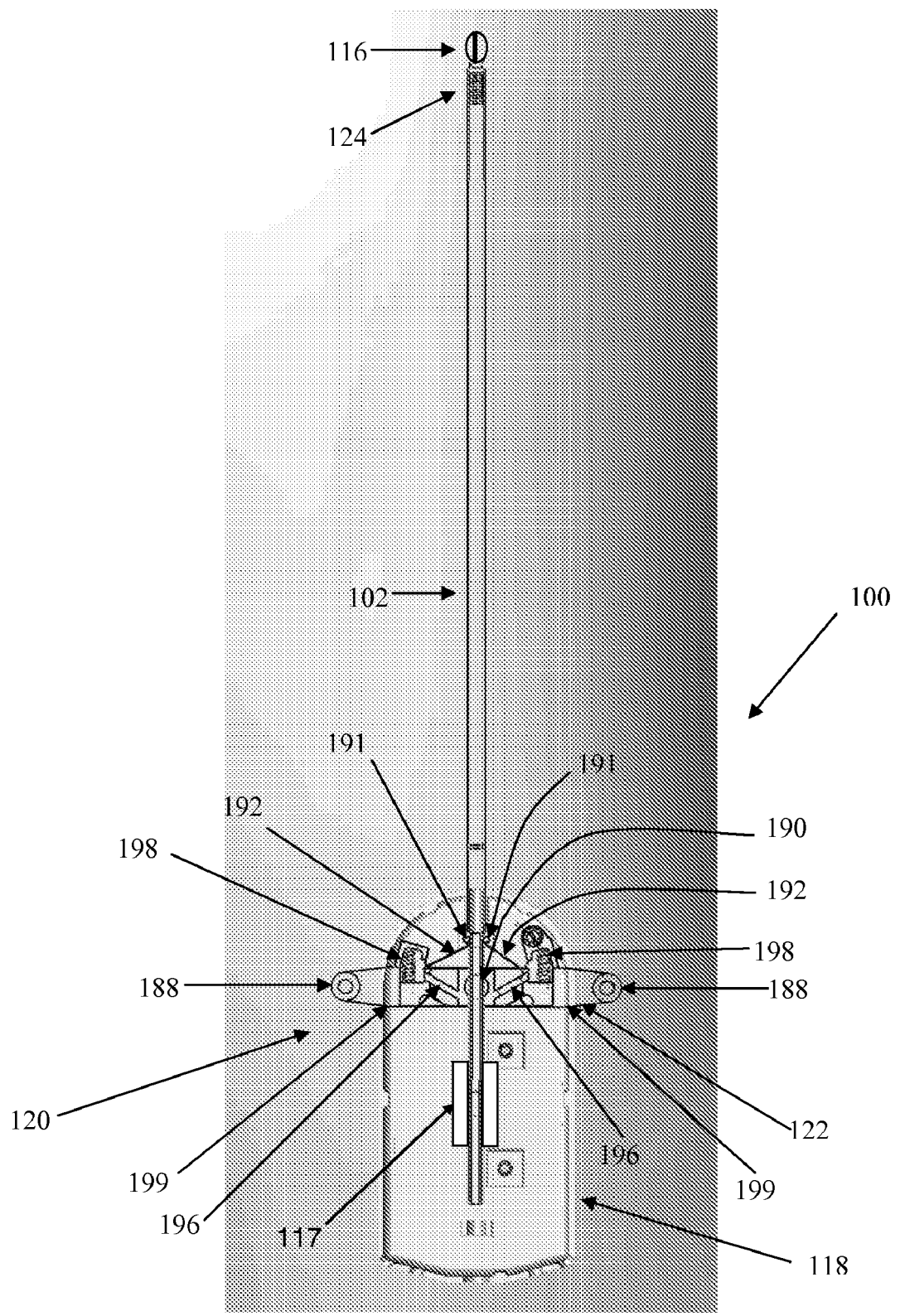
FIG. 8 is a schematic cut-away view of the housing of one embodiment of a retractor cannula device.

Referring still to FIG. 1, the steering mechanism 120 is configured to cause bending of the shaft 102 at one or more bending regions 124. In FIG. 8, the steering mechanism 120 is depicted with the port tubing and a portion of the housing 118 of the retractor cannula device 100 removed. The steering mechanism comprises a lever 122 that is configured to rotate or pivot at a lever axle 190. The lever 122 is attached to two control members 192 that are slidable located along the length of the shaft 102 and are attached at a distal location of the shaft 102. One or more posts 191 may be provided against the control members 192. In some embodiments, the posts 191 may be facilitate changes in the orientation of the control members 192, smooth sliding of the control members 192, and/or to protect other components of the retractor cannula device from cutting or other damage caused by the movement of the control members 192. In some embodiments, the ends of the control members 192 are secured to the lever 122 in one or more retaining channels or retaining structures, but in other embodiments, the control members may be proximally attached to form a control member loop that may be secured to a lever by placing the loop within a retaining channel of the lever. In some embodiments, one or more control members 192 or the control loop may be crimped, wound, sutured and/or embedded into the lever. The movement range and force may be augmented by one or more bias members 198 acting upon the lever 122. The bias members 198 may comprise helical springs as depicted in FIG. 8, but may also comprise leaf springs or any other type of bias member configuration. The movement range of the lever 122 may also be affected by the size and/or configuration of the lever openings 199 provided in the housing 118. In some embodiments, an optional locking mechanism may be provided to substantially maintain the lever in one or more positions.

Figure 9A:
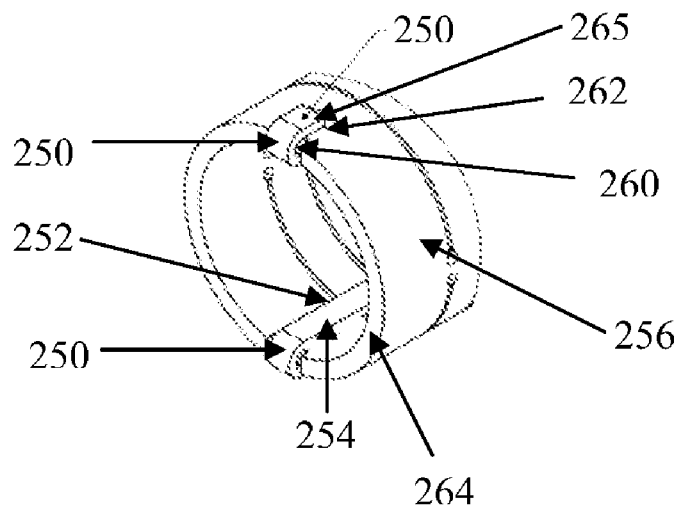
FIGS. 9A to 9C are detailed views of various embodiments of a cannula device with a steering mechanism.
Figure 9B:
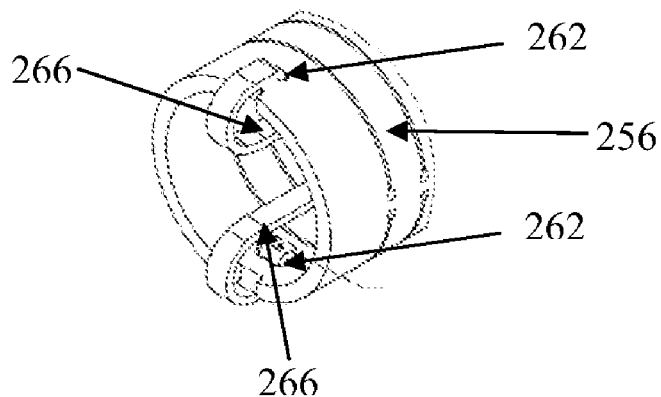
Figure 9C:
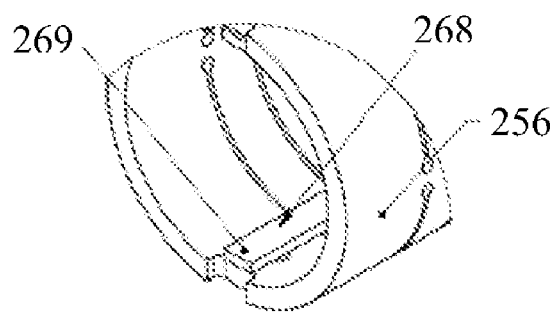

The control members 192 may comprise wires, threads, ribbons or other elongate structures. The flexibility and/or stiffness of the control member 192 may vary depending upon the particular steering mechanism. In further embodiments, the characteristics of the control member 192 may also vary along its length. In embodiments comprising two or more control members, the control members need not be configured symmetrically, e.g. having the same length, cross-sectional area or shape, or opposite attachment sites with respect to the longitudinal axis of the tubular shaft. Also, individual control members need not have the same configuration along their lengths. For example, although the proximal end of the control members 192 depicted in FIG. 8 comprises wire-like members, the distal ends 250 of the control members 252, illustrated in FIG. 9A, comprises ribbon structures 254. In some embodiments, the greater surface area of the ribbon structures may reduce the risk of damage to the flex region 256 of the cannula device 258. In the particular embodiment depicted in FIG. 9A, the ribbon structures 254 have a U-shaped configuration that forms a mechanical and/or interference fit with the flex region 256 or other distal or flexible region of the tubular shaft. The flex region 256 may comprise one or more notches 260, recesses or openings 262 configured to accept the ribbon structure 254. In FIG. 9A, notches 260 are provided to resist slippage of the ribbon structure 254 along the lip 264 of the flex region 256, while the openings 262 are provided to permit insertion of the ribbon ends 264 to further augment the interfit of the ribbon structures 254 and the flex region 256. FIG. 9B illustrates another embodiment where in the ribbon structure 266 inserts through the opening 262. In this particular embodiment, the ribbon structure 266 may also be welded or soldered back onto itself to form a loop to further secure the ribbon structure 266 to the flex region 256. In other embodiments, as depicted in FIG. 9C, the tip 269 of the ribbon structure 268 may be bonded or soldered to the flex region 256 or the tubular shaft, depending upon the material of the ribbon structures and the flex region or the tubular shaft.

The bending range of tubular shaft may vary depending upon the particular design. The cannula device may be configured with a one-sided or a two-sided bending range with respect to the neutral position of the tubular shaft. The bending range is from about 0 degrees to about 135 degrees, while in other embodiments, the bending range is from about 0 degrees to about 90 degrees, and sometimes about 0 degrees to about 45 degrees, and still other times about 0 degrees to about 15 or about 20 degrees. The bending range of the other side, if any, may be less than, equal to, or greater than the first side. In some embodiments, increased bending angles may cause creasing or telescoping of the tubular shaft, which may obstruct one or more channels within the tubular shaft.

Figure 10:
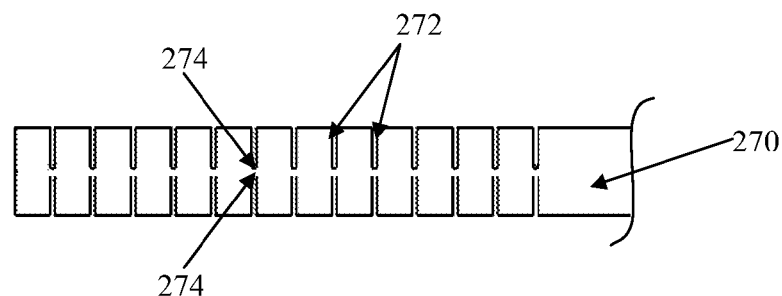
FIG. 10 depicts one embodiment of a flex region of a cannula device.

In some embodiments, to enhance the bending range of the tubular shaft, one or more flexion slots may be provided on the shaft. FIG. 10 depicts one embodiment of tubular shaft 270, comprising a plurality of slots 272. The slots 272 may have a generally circumferential orientation, but may alternatively have a helical orientation or other orientation. The slots 272 may be equally or unequally spaced along the longitudinal length of the shaft 270. In one example, the slots that are located about the ends of the flex region may be spaced farther apart than the slots located about the middle of the flex region. The slots 272 may have a similar configuration or a heterogeneous configuration. The slots 272 depicted in FIG. 10 also have a generally constant width, but in other embodiments, the width may vary along the length of the slot. The spacing between the slots ends 274 of a slot 272 may be substantially similar or different among the slots 272 comprising the flex region.

Figure 11A:
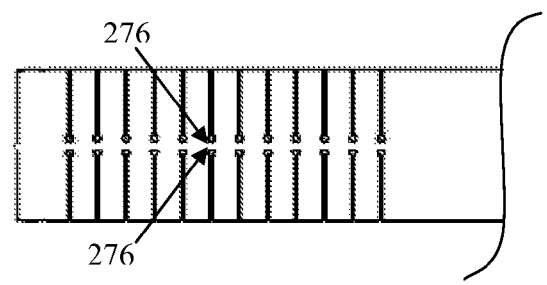
FIG. 11A depicts another embodiment of a flex region of a cannula device.
Figure 11B:
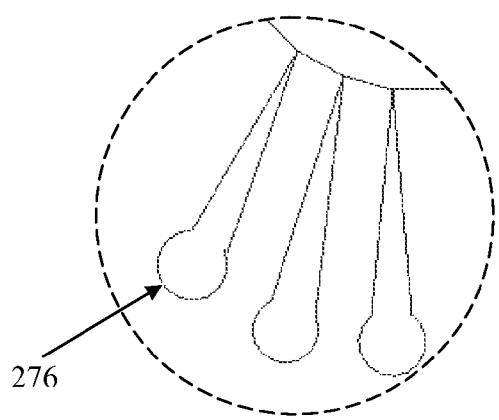
FIG. 11B is a detailed schematic view of a flex region during flexion.
Figure 12:
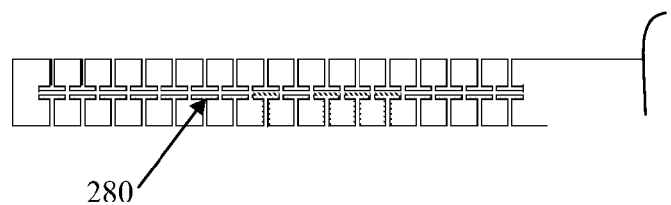
FIG. 12 depicts another embodiment of a flex region of a cannula device.

As noted in FIG. 10, the slot ends may comprise a rounded configuration, or any other configuration, including but not limited to an oval end, square end, triangular end, or any other polygonal shape for example. In some embodiments, such as the example depicted in FIG. 11A, the rounded ends 276 may have a larger transverse dimension than the width of the rest of the slot 278. In some embodiments, a rounded end may better distribute the flexion stress along the edges of the slot compared to squared or angled ends. Also, ends that are larger than the slots, such as the enlarged rounded ends 276 in FIG. 11A, may reduce the degree of compression or contact between the slot edges during flexion, which may also reduce the risk of cracking at the slot end. FIG. 11B depicts the enlarged rounded slot ends 276 of FIG. 11A in flexion. In some embodiments, the slot end may have a more complex configuration, such as the T-shaped slot end 280 as depicted in FIG. 12.

In some embodiments, the number of slots per slot region may be anywhere from about 1 slot to about 100 slots or more, sometimes about 12 slots to about 50 slots, and other times about 24 slots to about 48 slots. In some embodiments, the length of the flex region may be anywhere from about 1 inch to about 20 inches, sometimes from about 4 inches to about 10 inches, and other times about 5 inches to about 8 inches in length. In some embodiments, the outer diameter of the flex region may be about 0.05 inches to about 0.3 inches, sometimes about 0.08 inches to about 0.15 inches, and other times about 0.1 inches to about 0.12 inches. The wall thickness of the flex region may be in the range of about 0.001 inches to about 0.01 inches, sometimes about 0.002 inches to about 0.006 inches, and other times about 0.003 inches to about 0.004 inches. The slots 272 may have an average slot width in the range of about 0.004 inches to about 0.02 inches, some times in the range of about 0.005 inches to about 0.015 inches, and other times about 0.006 inches to about 0.008 inches. The spacing between the slots 272 may be in the range of about 0.015 inches to about 0.1 inches, sometimes about 0.020 inches to about 0.050 inches, and other times about 0.025 inches to about 0.04 inches. The spacing between the ends of the slots may be in the range of about 0.004 inches to about 0.05 inches, sometimes about 0.006 inches to about 0.02 inches, and other times about 0.004 inches to about 0.01 inches. The maximum transverse dimension of a slot end may be in the range of about 0.004 inches to about 0.008 inches, other times about 0.004 inches to about 0.03 inches, and other times about 0.01 inches to about 0.04 inches.

Figure 19:
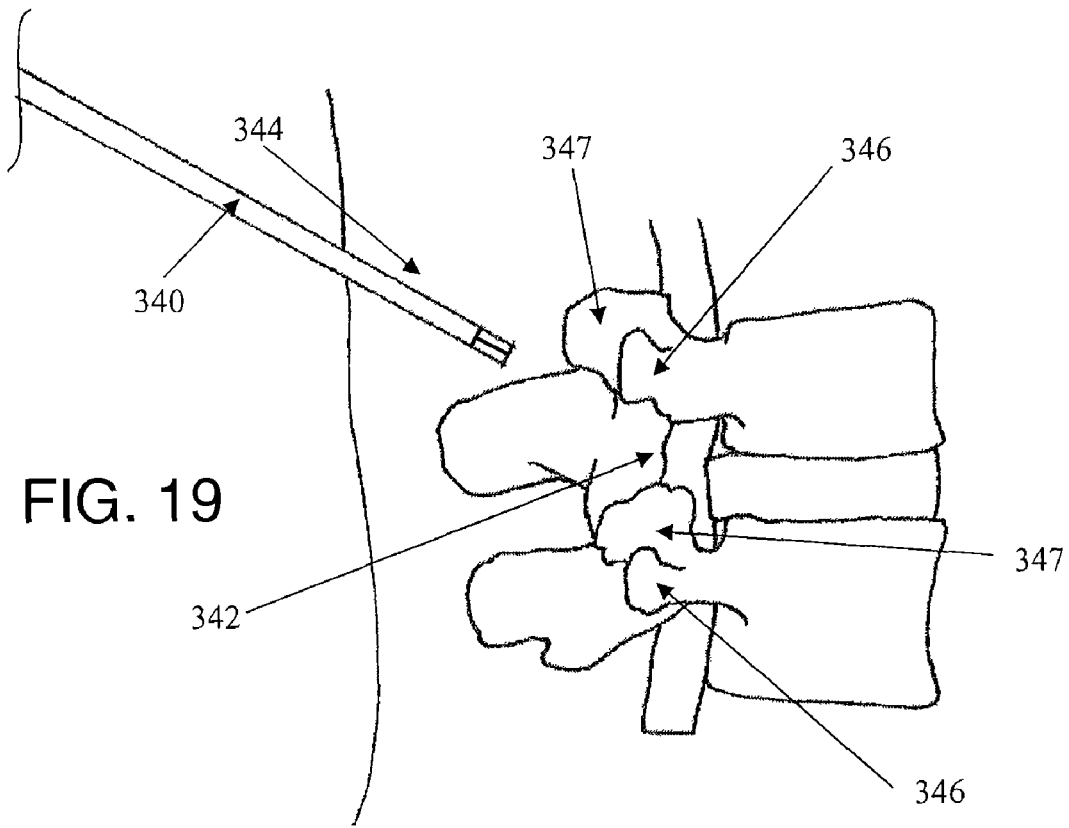
FIG. 19 is a schematic side cut-away view of one approach to the vertebrae.
Figure 20:
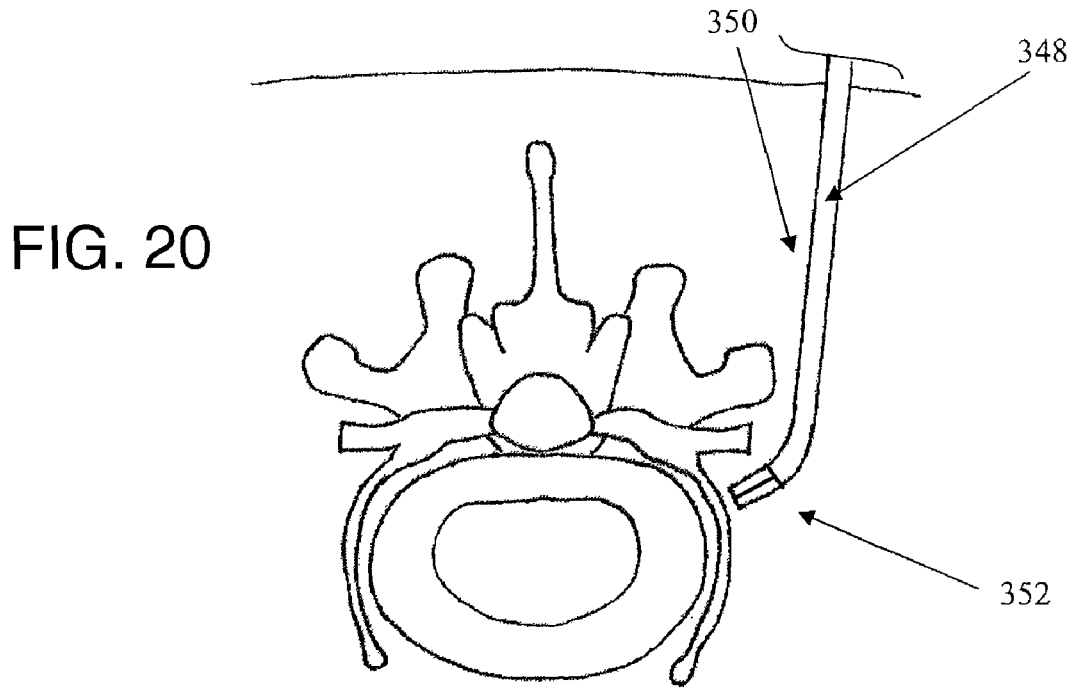
FIG. 20 is a schematic superior cut-away view of one approach to the vertebrae.

The flexion of the cannula system may facilitate access to the target site and/or reduce the degree of tissue disruption in achieving access to the target site. For example, in some procedures, the angle for approaching the target site through the skin may be different from the angle that provides the visibility or viewing angle to treat or diagnose a particular abnormality. Referring to FIG. 19, in some embodiments, a cannula system 340 may be inserted to a target site 342 by utilizing longer or indirect access pathways 344 in order to achieve the desired approach angle to a target site, and/or to avoid interference from structures such as the transverse spinal processes 346. By using a steerable cannula system 348 as depicted in FIG. 20, however, a shorter or a more direct insertion pathway 350 may be taken to a target site 352, which may reduce the aggregate degree of tissue disruption compared to a longer insertion pathway. By taking advantage of the steerability of the cannula system 348, the desired approach angle to a target site may be achieved.

Figure 13A:
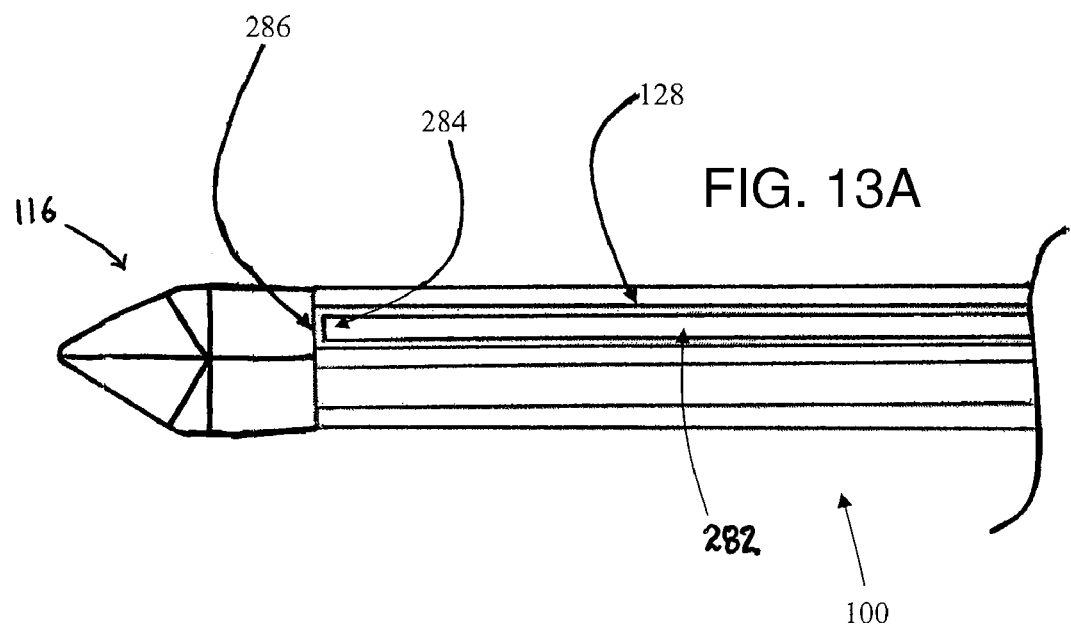
FIGS. 13A and 13B are schematic cross-sectional views of a retractor cannula device with an inserted endoscope in a neutral and a flexed position, respectively.
Figure 13B:
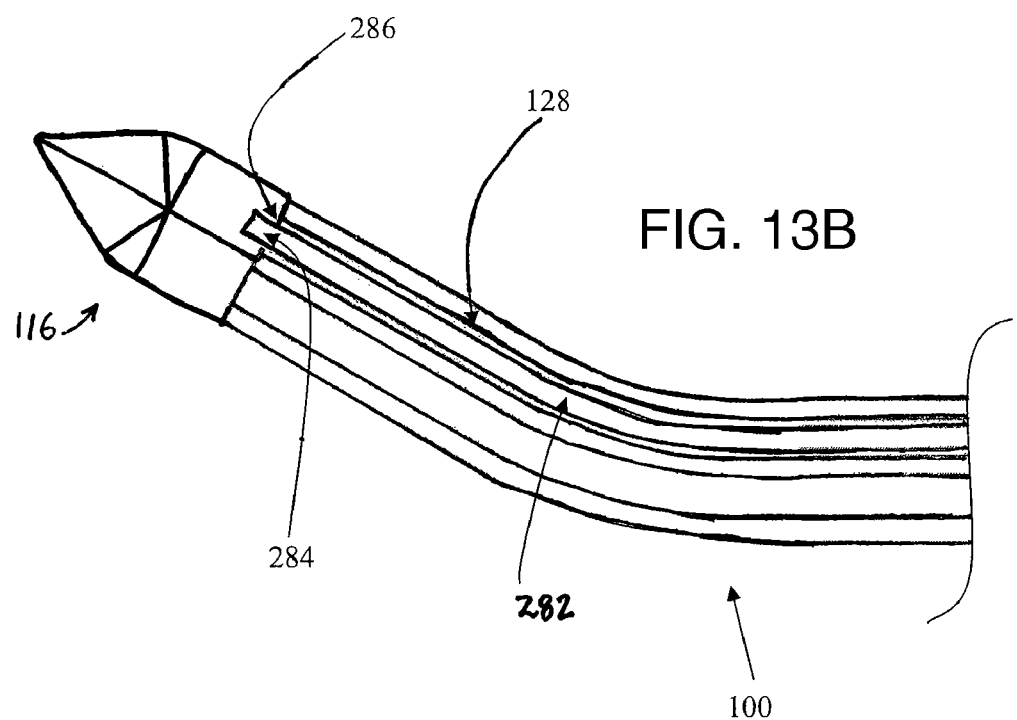

In some embodiments, during bending, one or more components inserted a channel of the retractor cannula device may exhibit different degrees of relative displacement. The degree of relative displacement may be affected by the degree of bending, the fixation or coupling site, if any between the component and the retractor cannula device, and/or the degree of displacement from the neutral position of the retractor cannula device. Referring to FIG. 13A, a retractor cannula device 100 shown in neutral position (e.g. straight, but may be angled or curved in other embodiments) with an endoscope 282 located in the visualization port 128. The tip 284 of the endoscope 282 is in proximity to the end 286 of the visualization port 128. As the retractor cannula device 100 is flexed as shown in FIG. 13B, the tip 284 of the endoscope 282 may exhibit a relative distal displacement with respect to the end 286 of the visualization port 128, particularly in embodiments where the endoscope 282 is coupled to the retractor cannula device 100 at a proximal location (e.g. about the housing). When the retractor cannula device 100 is flexed in the opposite direction, in some instances the endoscope 282 may exhibit a proximal retraction. To compensate for the displacement, the user may manually adjust the position of the endoscope 282 as desired.

In some embodiments, the steering mechanism may also be coupled to an endoscope adjustment mechanism so that manipulation of the steering mechanism also provides at least some position adjustment which may reduce if not eliminate the degree of displacement. In other embodiments, the endoscope may be coupled to the retractor cannula device about a distal region of the tubular shaft so that, during flexion, the proximal portions of the endoscope exhibit the displacement rather than the distal portions. In still other embodiments, a spring or other type of bias member may bias the endoscope distally against an interference structure (not shown) located at the distal end of the tubular shaft to maintain the endoscope position during flexion. In some further embodiments, the interference structure may be rotated or moved out of its interfering position to permit endoscope positioning more distally, as desired.

Figure 14:
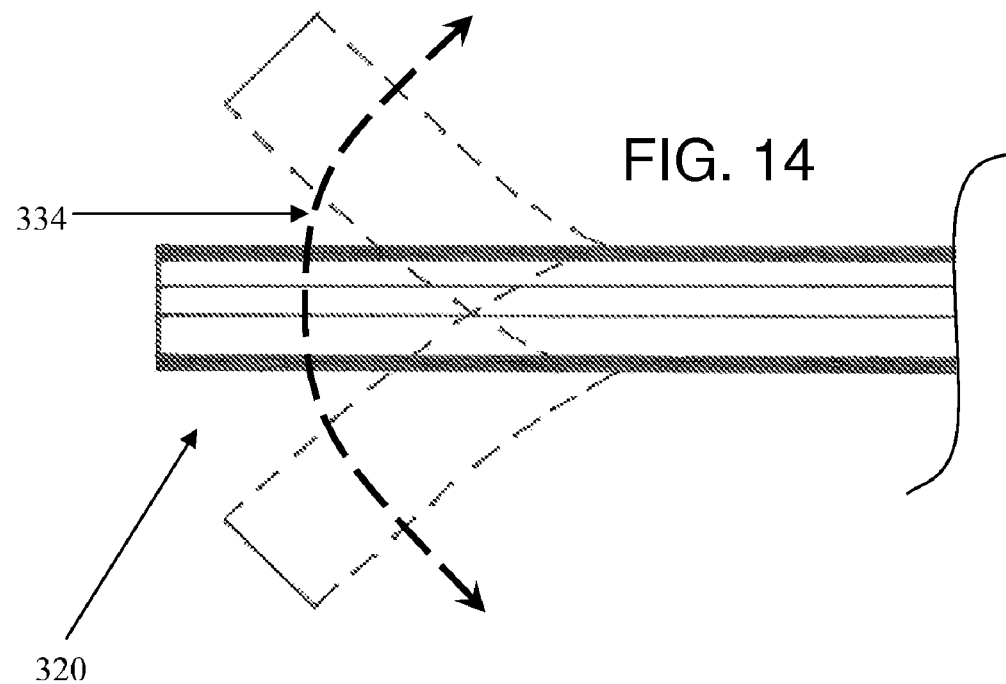
FIG. 14 is a schematic representation of one embodiment of a tubular shaft of a cannula device in a neutral position and in various flexed positions within a bending plane (depicted with dashed lines).
Figure 15:
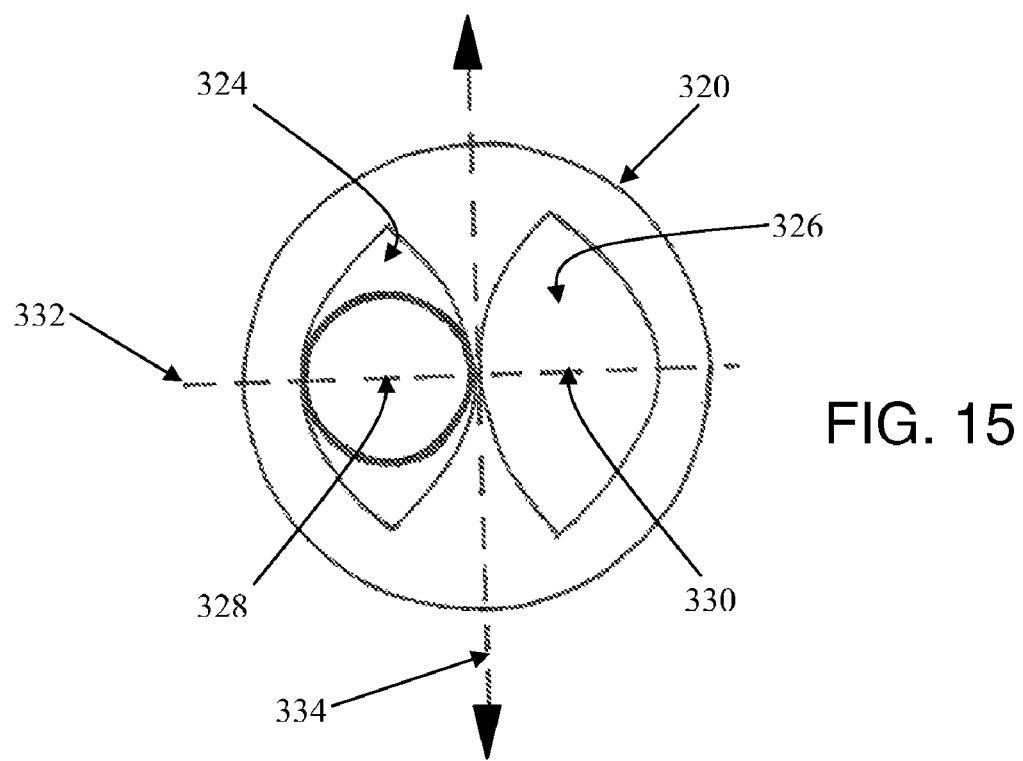
FIG. 15 is a schematic representation of one embodiment of a cannula device with two channels centered along a plane perpendicular to a bending plane of the cannula device.

FIG. 14 is a schematic representation of a tubular shaft 320 of one embodiment of a cannula device 322 configured for two-sided flexion within a bending plane. In some embodiments, one or more channels of the tubular shaft 320 may be configured and positioned to reduce the degree of endoscope or instrument displacement during flexion. In FIG. 15, for example, the tubular shaft 320 comprises a visualization channel 324 and a working channel 326 wherein the centers 328 and 330 of the channels 324 and 326, respectively, are located along a plane 332 that is perpendicular to a bending plane 334 of the cannula device 322. Plane 332 may be located, for example, between the midpoint of the two distal attachments of the steering mechanism. The relative position of the plane 332 and the bending plane 334 may vary depending upon the particular manner in which the steering mechanism is anchored to the flexion region. In other embodiments, the centers 328 and 330 need not be located on the plane 332, but the central location of the optics or working instruments inserted into the channels 324 and 326 are located on the plane 332. For example, a channel may be configured such that the optical center of an endoscope is substantially aligned with the plane 332, even through the weighted center of the channel and/or endoscope may not be located on the plane 332 (e.g. where the lens of the endoscope is asymmetrically located, or where the central viewing angle In embodiments comprising circular channels, the center of the channel may be the center of the circle. In other embodiments comprising non-circular channels, the center of a channel may be characterized as being coaxial with the center of the largest circular object that may be inserted into the channel.

Although the embodiment shown in FIG. 15 is directed to a cannula device having a single bending plane, in other embodiments, the cannula device may be configured with two or more bending planes. With these latter embodiments, one or more channels may be aligned with one bending plane but not another bending plane. In some embodiments, a central channel may be provided that is aligned with two or more bending planes.

As mentioned previously, an endoscope or working instrument (e.g. grasper(s), balloon(s) or tissue debrider) may be inserted into one or more channels of the cannula device through a proximal port. The proximal port, endoscope, and/or working instrument may be optionally configured with one or more features to lock and/or adjust the position of the inserted component. In other embodiments, one or more components of the endoscope or working instrument may be an integrally formed component of the cannula device and is not configured for removal.

Figure 16A:
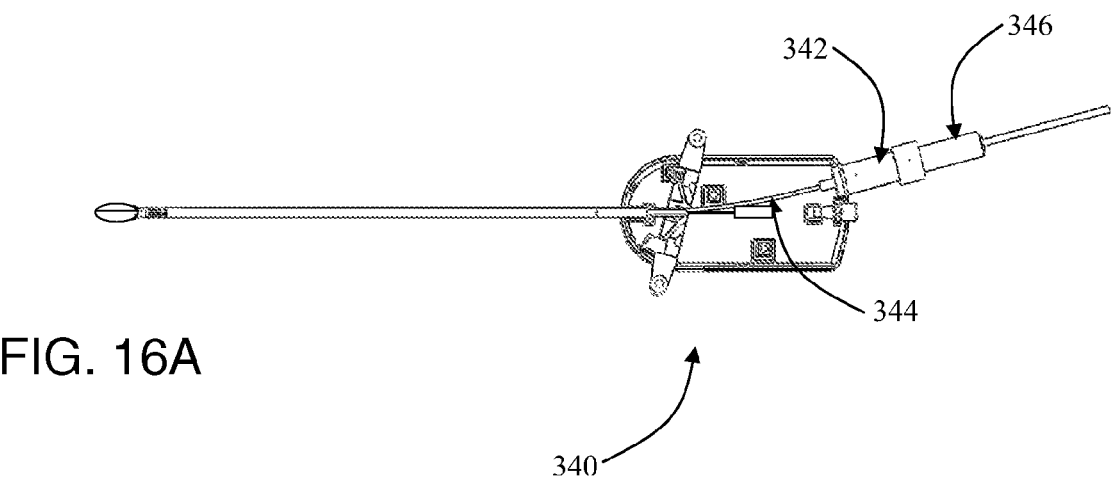
FIGS. 16A and 16B are cut-away and side elevational views of one embodiment of a retractor cannula device with an endoscopic coupling port, respectively.
Figure 16B:
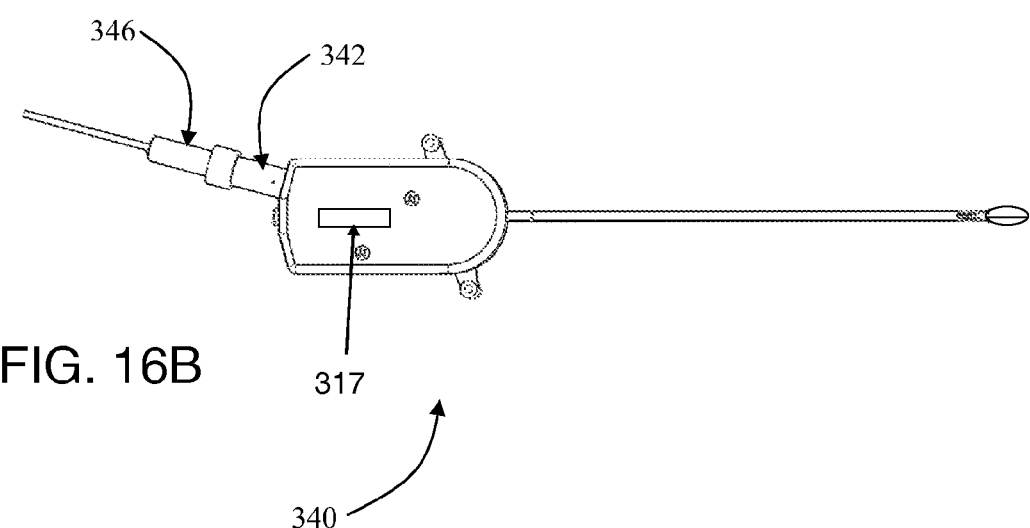

For example, in FIGS. 16A and 16B, a retractor cannula device 340 is configured with a scope port 342 in communication with the visualization channel (not shown) with a segment of tubing 344. The scope port 342 may comprise a lumen with a viscoelastic or friction surface material that is configured to slidably grip an inserted endoscope. The slidably grippable materials may include but are not limited to silicone, a urethane, including viscoelastic urethanes such as SORBOTHANE® (Kent, Ohio) and any of a variety of styrenic block copolymers such as some made by KRATON® Polymers (Houston, Tex.). The scope port 342 thus need not have any particular clamp or locking mechanism to secure the endoscope or working instrument to the scope port 243, nor any particular adjustment mechanism. In other embodiments, however, the scope port may comprise a releasable lock or clamp mechanism designed to couple to the endoscope or working instrument, with an optional adjustment assembly that may be used to modify the spacing between the lock or clamp mechanism and the housing.

Figure 17:
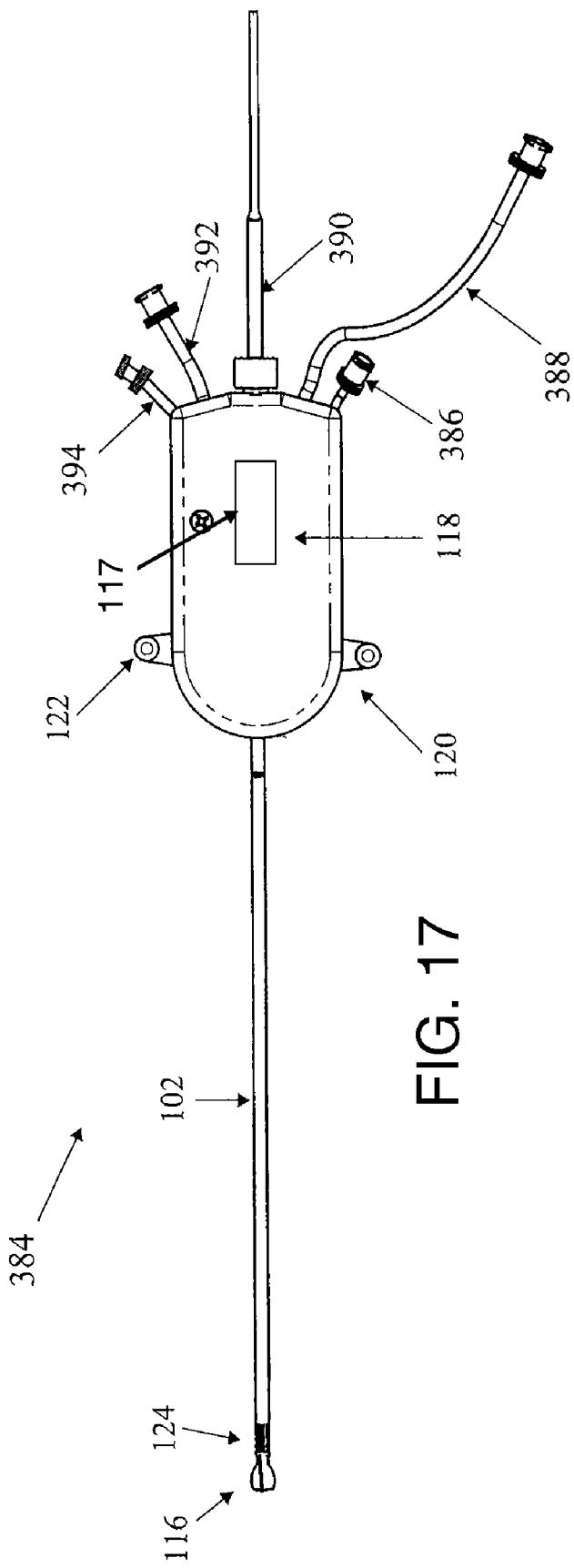
FIG. 17 is a cut-away view of the retractor cannula device of FIG. 8 with tubes connected to the tubular shaft.
Figure 18:
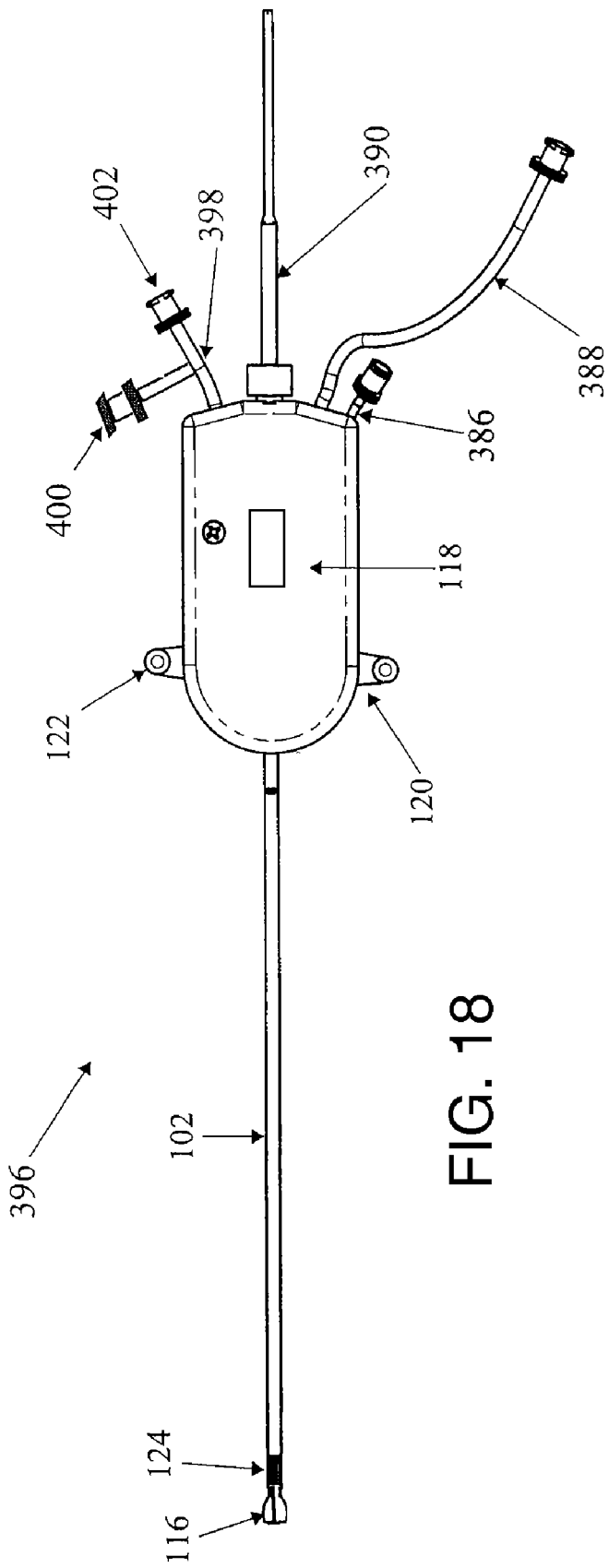
FIG. 18 is a side elevational view of the retractor cannula device of FIG. 17.

Referring now to FIG. 17, the proximal end 360 of the tubular shaft 362 may be coupled to one or more tubing segments 364, 366, 368, 370, 372 that correspond to one or more channels and connectors 374, 376, 378, and 380 of the retractor cannula device 382, respectively. As noted in FIG. 17, a tubing segment 370 may be in communication with another tubing segment, such as the tubing segment 368, which connected to the working channel of the device 382. This particular tubing segment 370 may be used, for example, to flush or aspirate fluid or material inserted into the working channel of the device 382 that is accessed through the middle port 378 and tubing segment 368. The particular design features of a tubing segment may vary, depending upon the particular function. The connector coupled to a particular tubing segment may comprise any of a variety of connectors or instrument interfaces. In some embodiments, for example, one or more connectors may comprise a standardized connector such as Luer lock, while in other embodiments, the connector may be a proprietary connectors. Depending upon the particular channel, in some embodiments, a check valve, septum, or a hemostasis valve may be provided to resist retrograde flow of fluid out of the device. The characteristics of a particular channel, including its dimensions and flexibility or rigidity, may depend upon its particular use. In FIG. 18, for example, a retractor cannula device 384 comprises five ports 386, 388, 390, 392 and 394, wherein the longer, flexible ports 388 and 392 may be used for infusion or aspiration. Such ports may be beneficial to facilitate the attachment of a bulky item such as a syringe. A rigid port, such as port 390, may be provided for instruments that may otherwise be damaged or are difficult to pass through tubing that may exhibit greater frictional resistance.

The retractor cannula devices may be used, for example, in systems for treating disc degeneration or other defects that include nucleus decompression devices. The retractor cannula device may be used for accessing the nucleus and delivering a nucleus decompression device. For example, a decompression device may be advanced from one of the working channels of the retractor cannula device and into the nucleus of a disc. A nucleus decompression device may be used to removed the disc nucleus tissue either by dissection, suction, dissolving, or by shrinking the nucleus. Various types of thermal energy are known to shrink the nucleus such as resistive heat, radiofrequency, coherent and incoherent light, microwave, ultrasound or liquid thermal jet energies. Mechanical tissue removal devices may also be used. Decompression of the disc nucleus may result in the protruded disc material collapsing toward the center of the disc. This may reduce the pressure on the spine nerve roots, thereby minimizing or reducing the associated pain, weakness and/or numbness in the lower extremities, upper extremities, or neck region. One or more devices that may be used to strengthen and/or support the weakened disc wall may also be used with a retractor cannula device.

In additional to spinal applications, the atraumatic cannula system may also be used for a variety of other procedures. The atraumatic cannula system, including the retractor cannula systems, may be used to provide direct visualization to a variety of both bedside and surgical procedures that were previously performed blind and/or with indirect visualization. Such procedures include but are not limited to pleural biopsy, pleuracentesis, paracentesis, renal biopsy, and joint aspiration, for example. In another example, the cannula system may be used in the emergency room or trauma centers to perform peritoneal taps to diagnosis blunt abdominal trauma.

In some embodiments, the retractor cannula device may be used for diagnostic purposes. Because of the complexity of the spine, it may be more difficult to diagnose an injury than for other medical conditions. As such, the direct visualization capabilities of the subject devices may be able to accurately identify any instability or deformity in the spine. For example, the subject device may offer direct visualization of any tumors, fractures, nerve damage, or disc degeneration or other defects. In addition, the subject devices may include sensors for collecting diagnostic data, for example, sensors that measure flow, temperature, pressure, or oxygen concentration. The subject devices may also be used to remove fluid, tissue or bone samples to be used for external diagnostic tests. Additionally, the subject devices may deliver testing reagents or additional instruments for diagnosing disc degeneration or other defects and bony degeneration, for example, the subject devices may deliver electrodes for diagnosis and treatment.

In one embodiment, the retractor cannula device may be used to perform discectomy. In this particular embodiment, the patient is prepped and draped in usual sterile fashion and in a lateral decubitis or prone position. General, regional, or local anesthesia is achieved and a rigid guidewire may be inserted percutaneously to the epidural space. Guidewire placement may be performed under fluoroscopic guidance or other types of indirect visualization including ultrasound. In some instances, a small skin puncture or incision is made about 2 to 5 inches from the midline of the patient's lumbar region to facilitate guidewire insertion. A needle may also be used to facilitate guidewire passage through some tissues. The guidewire may introduced on the ipsilateral side from which the nerve impingement has been identified and at an angle of about 25 degrees to about 45 degrees to the patient's back, but in other procedures, a contralateral approach and/or a different angle may be used. After confirmation of the guidewire location, a dilator may or may not be inserted over the guidewire to enlarge the guidewire path to the epidural space. An introducer with a releasable lock may be inserted over the dilator to maintain access so that the dilator and guidewire may be removed. An endoscope or other type of direct visualization may be inserted into the scope channel of the retractor cannula device. An irrigation fluid source is connected to the irrigation port on the retractor cannula and activated to provide continuous flushing. A passive or active aspiration port or outlet port is checked for patency. The retractor cannula is inserted into the introducer and advanced toward the epidural space. Direct visualization of the epidural space may be performed with the endoscope as the retractor cannula nears the epidural space. As the retractor cannula enters the epidural space, the retractor assembly may be manipulated (e.g. flexed and/or rotated) to orient the user and to identify the spinal nerve and for any disc or foraminal pathology. The retractor cannula device may then be advanced closer to the treatment site. Where the treatment site is abutting or impinging upon a nerve, the retractor assembly in the open configuration may be used to separate the treatment site and the nerve and to create a working space at the treatment site. In some embodiments, a guidewire may be reinserted into a channel of the retractor cannula and advanced past the tip of the retractor assembly toward the treatment site. For example, the guidewire may be inserted into a bulging region of the annular wall at the site of impingement. Insertion may occur before or after the retractor assembly is urged into the open configuration, and before or after a nerve is separated from a bulging disc surface. Under visual guidance, the open jaws of the retractor assembly may be directed towards the tissue to be removed, and then urged to the closed configuration, thus grasping the tissue. Appropriate maneuvering techniques may then be applied to remove the tissue gripped by the jaws of the retractor assembly. Alternatively or additionally, a tissue disrupting instrument may be inserted in the retractor cannula device and activated to mince or disrupt the tissue at the treatment site. For example, the retractor cannula device may be configured to house an automated auger, which can be turned on to spin within the chamber space enclosed by the retractor assembly to quickly remove tissue. Alternatively or additionally, negative pressure may be applied through the auger to draw the tissue targeted for removal into the working channel. The disrupted material may be swept away by the continuous irrigation and flush system, or may be removed from the treatment site by an aspiration assembly on the tissue disrupting instrument, or secured by the jaws of the retractor assembly which is then withdrawn distally. A coagulation probe, if needed, may be inserted into the retractor cannula to achieve hemostasis and/or to shrink tissue. In some embodiments, the treated disc surface may self-seal due to the small size of the tissue disrupting instrument and/or the reduced pressure in that portion of the disc following removal of disc material. In other embodiments, the treated disc may be further treated to reduce any extrusion of disc material from the treatment site. A forceps or additional grasper instruments may also be used with the retractor cannula device to remove any extra-discal fragments. In some instances where fragments may have migrated through a foramen of the vertebrae, the size of the retractor cannula may permit advancement of the retractor cannula into or even through the foramen. Thus, the retractor cannula device may be inserted into the central spinal canal from the foramen to retrieve any migrated fragments.

In another embodiment, a retractor cannula system may be utilized for any of a variety of cardiothoracic procedures, including but not limited to bronchoscopy, pleural biopsy, pleuracentesis pericardiocentesis, and pericardial biopsy. Pericardial biopsy, for example, is indicated for the investigation of a pericardial effusion. The procedure may be performed under fluoroscopic guidance or using endoscopic instruments, but is still associated with substantial morbidity, including but not limited to risks of a pneumothorax and myocardial rupture. A minimally invasive, direct visualization alternative may improve the risk/benefit profile of the procedure. In one particular embodiment, the patient is prepped and draped in usual sterile fashion. Local anesthesia is achieved in the subxiphoid region of the patient. In other embodiments, other entry points into the thoracic cavity may be used instead. In other embodiments, regional or general anesthesia may be used instead. In some embodiments where a pericardial drainage catheter was already in place, the guidewire may be inserted into the catheter and the catheter may be removed, leaving the guidewire in place. The guidewire may be a straight guidewire or a J-tip guidewire, for example. In embodiments where an initial entry into the pericardial space is made by the guidewire, a catheter may be inserted over the guidewire and one or more pericardial fluid samples may be taken for chemistry, histology, and/or culture, for example, before continuing the procedure. One or more dilators may be inserted over the guidewire and removed to widen the tissue pathway from the skin to the pericardial space. After widening the guidewire pathway, the retractor cannula system may be inserted over the guidewire. In some embodiments, as the retractor cannula system is inserted, a sampling of the parietal pericardial tissue (i.e. the outer pericardial surface) may be taken before or after the placement of the retractor cannula system into the pericardial space. In some embodiments, the retractor assembly may be in the open configuration and pressed against the parietal pericardial surface. An additional retractor assembly may be used to take one or more tissue biopsies of the parietal pericardial surface. A coagulation probe may be used to provide hemostasis following the biopsy or biopsies. The retractor cannula may be placed in the closed configuration and advanced distally over the guidewire toward the pericardial space. Once in the pericardial space, the guidewire is optionally removed from the retractor cannula system. The pericardial fluid may be drained and replaced with saline or a gas to facilitate viewing. In patients with a hemorrhagic effusion, additional irrigation and/or drainage may be used to improve the clarity of the viewing field. The retractor assembly may be placed in the open configuration and the pericardial space may be explored by flexing and/or rotating the retractor cannula device. In some embodiments, the retractor cannula may be flexed in a retrograde fashion and the extended retractor assembly tip of the retractor cannula is used to atraumatically tent up the pericardial tissue to reduce the tissue laxity and increase the success of the biopsy. Unlike traditional endoscopic procedures, which are sometimes contraindicated when there is insufficient fluid or loculated fluid in the pericardial sac, use of the duckbill-shaped retractor cannula system may facilitate tissue separation between the pericardium and the epicardium to safely perform the biopsy in those situations. Tissue biopsies of the visceral pericardium and/or the epicardium may be taken using graspers or other endoscopic biopsy tools. Using a tissue debrider and/or a coagulation probe, one or more windows or fenestrations may be formed in the pericardium to provide ongoing drainage of the pericardial effusion. Pericardial windows or fenestrations, if any, may be performed before or after entry into the pericardial space. The retractor cannula may then be removed and an x-ray may be taken to check for a pneumothorax. If needed, chest tube drainage may be provided until the pneumothorax has resolved.

Diagnoses and treatments of spinal diseases often include procedures that require delivering visualization devices and/or other surgical devices to the epidural space. The epidural space is bound anteriorly and posteriorly by the longitudinal ligament and the ligamentum flavum, respectively, of the vertebral canal, and laterally by the pedicles of the vertebral arches and the intervertebral foramina. It may be necessary to dilate these surrounding tissues and structures to access the epidural space. One problem associated with such dilation is that while the tissues (e.g., various ligaments) enclosing the epidural space are relatively stiff, the tissues contained inside the epidural space, such as fat, nerves and blood vessels, are soft. Ideally, the operator may use a dilator to dilate the ligaments or other connective tissues. Once the dilator passes through the ligaments and reaches the cavity inside the epidural space, the operator should stop the dilator to avoid damaging the soft tissues contained therein. However, dilating tough tissues, such as ligaments, often requires significant amount of force be applied to the dilating device to overcome the frictional forces generated by the tissues. Once the frictional forces are overcome, the sudden loss of distal resistance may cause the dilator to advance too far into the epidural space and injure the tissues contained therein. It is difficult to control the motion and the depth of penetration of a traditional dilator. One existing approach to solve this problem is to use a rongeur to cut through tough layers of ligaments. However, this procedure is time-consuming, complicated and may cause greater collateral damage during access.

Described below are dilators that are configured to dilate tissues in a controlled manner such that they may be used to differentiate tough connective tissues layers, such as ligaments and materials, from low shear modulus of elastic stiffness, such as fluids and soft tissues contained within the epidural space. In some embodiments, the dilator comprises a threaded taper at its distal end. The dilator dilates through tissue layers in helix motion driven by rotational forces. Due to slower speed and higher torque, the rotational force offers better control than axial force. Embodiments and variations of current invention will be discussed in greater detail below. It should be noted that while embodiments and methods of using such embodiments are described in detail in the context of diagnosing and treating spinal diseases, such devices and methods may be used, and are contemplated for use, in other medical procedures.

Figures 21A, 21B:
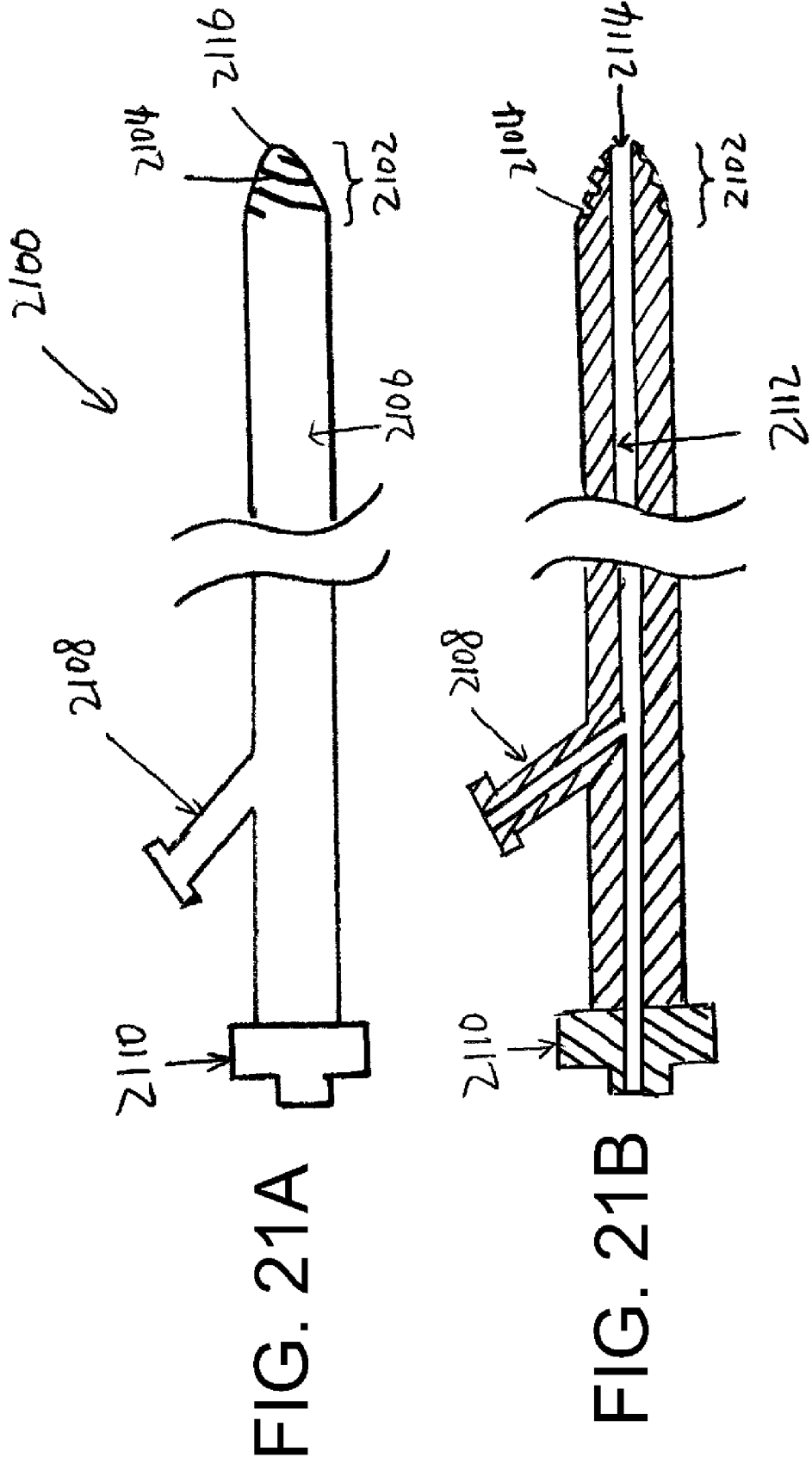
FIG. 21A schematically illustrates one embodiment of a threaded dilator.
FIG. 21B is a cross-sectional view of the embodiment in FIG. 21A.
Figure 22A:
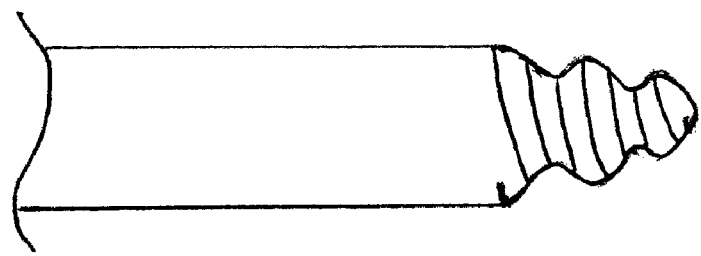
FIGS. 22A to 22C illustrate various configurations of a threaded dilator.
Figure 22B:
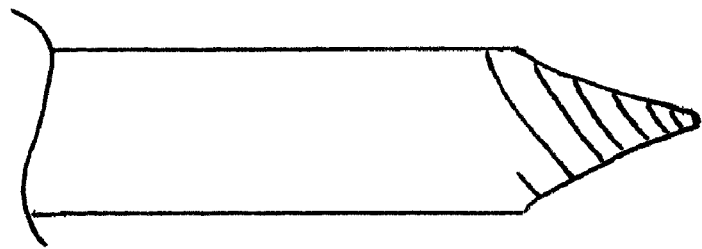
Figure 22C:
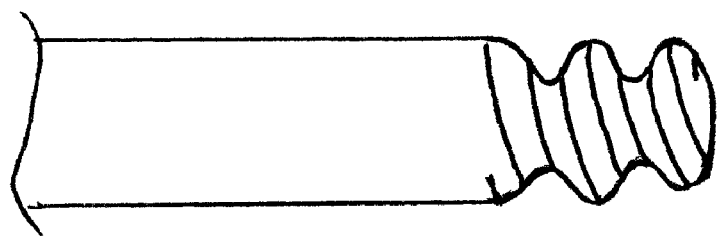

FIGS. 21A and 21B depict one embodiment of a threaded dilator 2100. Dilator 2100 comprises a distal taper 2102 mounted on the distal end of a shaft 2106. Taper 2106 are threaded with one or more spiral grooves 2104. The proximal end of the shaft 2106 is attached to a handle 2110, which may be used to manipulate and control the motion of the dilator 2100. In some embodiments, handle 2110 may comprise gripping materials or textured gripping surfaces to facilitate manual operations. Some examples of gripping materials may include, but are not limited to, silicone, urethane (e.g., viscoelastic urethanes such as SORBOTHANE®), and any of a variety of styrenic block copolymers such as some made by KRATON® Polymers. Seen best in FIG. 21B, the shaft 2106 may comprise an interior pressure lumen 2112, which is in fluid communication with a distal port 2114 located at the distal end 2116 of the dilator taper 2102, and a proximal port 2108 located on the proximal portion of the shaft 2106. In some variations, the interior lumen 2112 and the two ports 2102 and 2108 may be used as a pathway for a guide wire, an endoscope or other instruments that may be used associated with dilator 2100. In some embodiments, the distal end 2116 of the dilator 2100 may be round or otherwise blunt to reduce inadvertent damage to surrounding tissues when the dilator is extended from a cannula or is advanced directly to the dilating site. A threaded dilator may be used when a passageway or a working channel to the dilating site has been previously formed or when blunt dissection is sufficient.

The proximal port 2108 may be further connected to a pressure applicator (not shown) to apply pressure to the dilator taper 2102 via the pressure lumen 2112. The pressure applicator may further comprise pressure gauging mechanism to monitor the pressure within the pressure lumen 2112. In some embodiments, the pressure applicator comprises one or more pumps. The pump may be any of a variety of suitable pumps, including but not limited to variable volume pumps, syringe pumps, peristaltic pumps, piston pumps, or diaphragm pumps. In some embodiments, the pressure applicator is a volumetric pump that is configured to move a pre-specified volume of fluid into the pressure lumen 2112. In other embodiments, the pressure applicator is configured to apply pressure to the pressure lumen 2112 by pumping in fluids at a pre-specified flow rate. In one embodiment, the pressure applicator may be a syringe. The syringe may further comprise a plunger and a reservoir, which may be used to apply pressure to the pressure lumen 2112. In some embodiments, pressure may be applied by the plunger being pushed forward manually. In other embodiments, a spring assembly associated with a pressure gauge may be used to control the motion of the plunger, which in turn, will apply and maintain the pressure level within the pressure lumen 2112. Alternatively, the proximal port 2108 may be connected to a vacuum source and be used as an exit to aspirate or vacuum fluid and suspended materials out of the treatment site.

As noted above, in a discectomy, a dilator may be used to penetrate and dilate ligaments in order to provide an enlarged pathway for other surgical instruments to reach the epidural space. In some embodiments, dilator 2100 may be inserted over an introducing guidewire from a posterior or posterolateral location of the patient's back. Dilator 2100 may first be advanced over the guidewire to pass body tissues such as skin and muscle. While dilator 2100 is being advanced over the guidewire, the operator may apply pressure from the proximal port 2108 by irrigating a fluid, such as saline or medical grade gas (e.g., air or carbon dioxide), into the pressure lumen 2112. Before the distal end 2116 of dilator 2100 reaches the ligament, the irrigated fluid is flushed out through the distal port 2114. As a result, the pressure inside the pressure lumen 2112 will not build up. However, when the distal end 2116 of dilator 2100 reaches the ligaments and the threads 2104 engage the tissue, the fluid pressure within the lumen 2112 will increase due to resistance from the ligaments. At this point, the operator may stop pushing the dilator axially but instead, start rotating the dilator for a more controlled advancement.

In some variations, the operator may use the guidewire, but not irrigated fluid, to monitor and detect the location of the tip of the dilator. Because the guidewire is less stiff and has a smaller footprint than the dilator, it is less likely to overpenetrate a guidewire through the ligaments and damage nerves inside the epidural cavity. The operator may use the guidewire as a probe and advance the guide wire and the dilator in an alternating fashion. For example, the dilator may first be advanced over the guidewire to the location of the distal end of the guidewire. The guidewire may then be pushed further to advance a short distance, followed by the advancement of the dilator by the same distance. These steps may be repeated until the distal threads of the dilator engage the ligaments.

Once the distal threads engage the ligaments, the operator should stop applying axial forces upon the dilator and start applying rotational force to the dilator shaft 2106 in order to threadingly advance the dilator. The operator may rotate the dilator in the same direction as the winding orientation of the spiral grooves 2104. Because the epidural cavity may contain fluid and soft tissues with low modulus, once the tip 2116 of the dilator 2100 crosses the ligaments and reaches the epidural space, the flow resistance at the distal end 2116 of the dilator 2110 drops significantly and so does the pressure level within the pressure lumen 2112. When such pressure drop is observed, the operator may stop rotating the shaft 2106 of the dilator 2100. In some embodiments, the shaft 2106 may be rotated by one or more turns in order to advance the tip 2116 of the dilator 2100 slightly further into the epidural space without damaging nerves or blood vessels contained therein. The number of turns that may be applied to slightly advance the dilator tip depends, in part, on the thread pitch of the dilator 2100.

Once ligaments are dilated, a cannula retractor device, various embodiments of which have been described in great detail above, may be advanced over the dilator to access the epidural space and to perform various procedures. In other examples, the dilator may be removed from the subject and different instruments or devices may be inserted through the tissue pathway formed by the dilator. In some variations, the dilator may comprise a stopper that can stop the motion of the cannula device such that the cannula will not be advanced over the distal tip of the dilator. In this fashion, the cannula device will not be inserted inadvertently into the epidural space or damage the soft tissues located therein. For example, a threaded dilator may comprise an annular bulge located near the proximal end of the dilator taper. The inner diameter of the annular device may be slightly larger than the outer diameter of the annular bulge. When a cannula device with its jaws biased in their open configuration is being advanced over the dilator, the operator will perceive a resistance once the jaws are stopped by the bulge on the dilator and may stop advancing the cannula device at this point. If the longitudinal length of the jaws is substantially the same as the length of the dilator taper, the cannula device will not overpenetrate the ligaments and damage tissues inside the epidural space. In the mean time, once the cannula device is stopped by the stopper, the operator is acknowledged that the distal tip of the cannula device has already reached the epidural space. In some embodiments, the jaws of the retractor cannula may be opened further to allow the dilator to pass through and to be proximally withdrawn. In some variations, the stopper may be a tab other types of protrusion. The stopper may be located at any spot along the longitudinal axis of the dilator. The location of the stopper may depend, in part, on the specific configuration of the stopper and the configuration of the cannula.

In one embodiment, the cannula device may comprise complementing helical threads on the inner surface of its jaws and/or its interior lumen such that the cannula may be threadingly advanced over the threaded dilator by rotation. When in use, the dilator may first be advanced to the target site (e.g., the distal tip of the dilator just passes the ligaments and reaches the epidural space), the cannula device may first be pushed over the dilator until the distal portion of its inner threads engage the proximal portion of the threads on the dilator. The cannula device may then be advanced through rotation in a more controlled fashion. In this particular embodiment, only the inner surface of the cannula jaws are threaded. In other embodiments, the outer surface of the cannula device may be threaded such that the device may be advanced through body tissues in a controlled fashion when being used without a matching dilator.

In some embodiments, the longitudinal length of the taper of a dilator may be in the range of about 0.5 mm to about 5 mm, sometimes about 1 mm to about 4 mm, and other times about 2 mm to about 3 mm. The dilator may have a taper angle in the range of about 5° to about 45°, sometimes in the rang of about 10° to about 40°, and other times in the range of about 20° to about 30°. The "taper" is used here to encompass any distal structure that comprises an outer diameter not greater than that of the dilator shaft. The taper generally comprises a round cross-sectional shape but the cross-sectional area of the taper may change along its longitudinal axis. This change may be linear or non-linear and may be continuous or non-continuous. FIGS. 24A to 24C schematically illustrate some variations of the taper configurations.

"Thread" is used to include helical or spiral cutting edges, protrusions or any other type of helical or spiral surface structures that may facilitate rotational advancement of the dilator. In some embodiments, the entire body of the dilator taper is threaded. In other embodiments, there is a distal potion of the taper that is not threaded. The longitudinal length of this unthreaded distal portion may be in the range of about 0.1 mm to about 2 mm, sometimes about 0.5 mm to about 1.5 mm, and other times about 0.75 mm to about 1.25 mm. In still other embodiments, there is a proximal portion of the taper that is not threaded. In yet other embodiments, the threads may extend from the taper of the dilator over to a portion of the draft. The length of such threaded portion on the shaft may be in the range of about 0.1 mm to about 2 mm, sometimes about 0.5 mm to about 1.5 mm, and other times about 0.75 mm to about 1.25 mm. In some embodiments, the threads on the dilator may be continuous, but in other embodiments, they may be broken at one or more spots. The threads of the dilator may have any suitable cross-sectional shape. Examples of suitable cross-sectional shapes include, but are not limited to, triangles, rectangles, trapezoidal or U-shape. The dilator may be single threaded or multi-threaded (e.g., double-threaded or triple-threaded). The multi-threaded configuration may provide longer advancement distance with fewer rotations of the shaft.

Figures 23A, 23B:
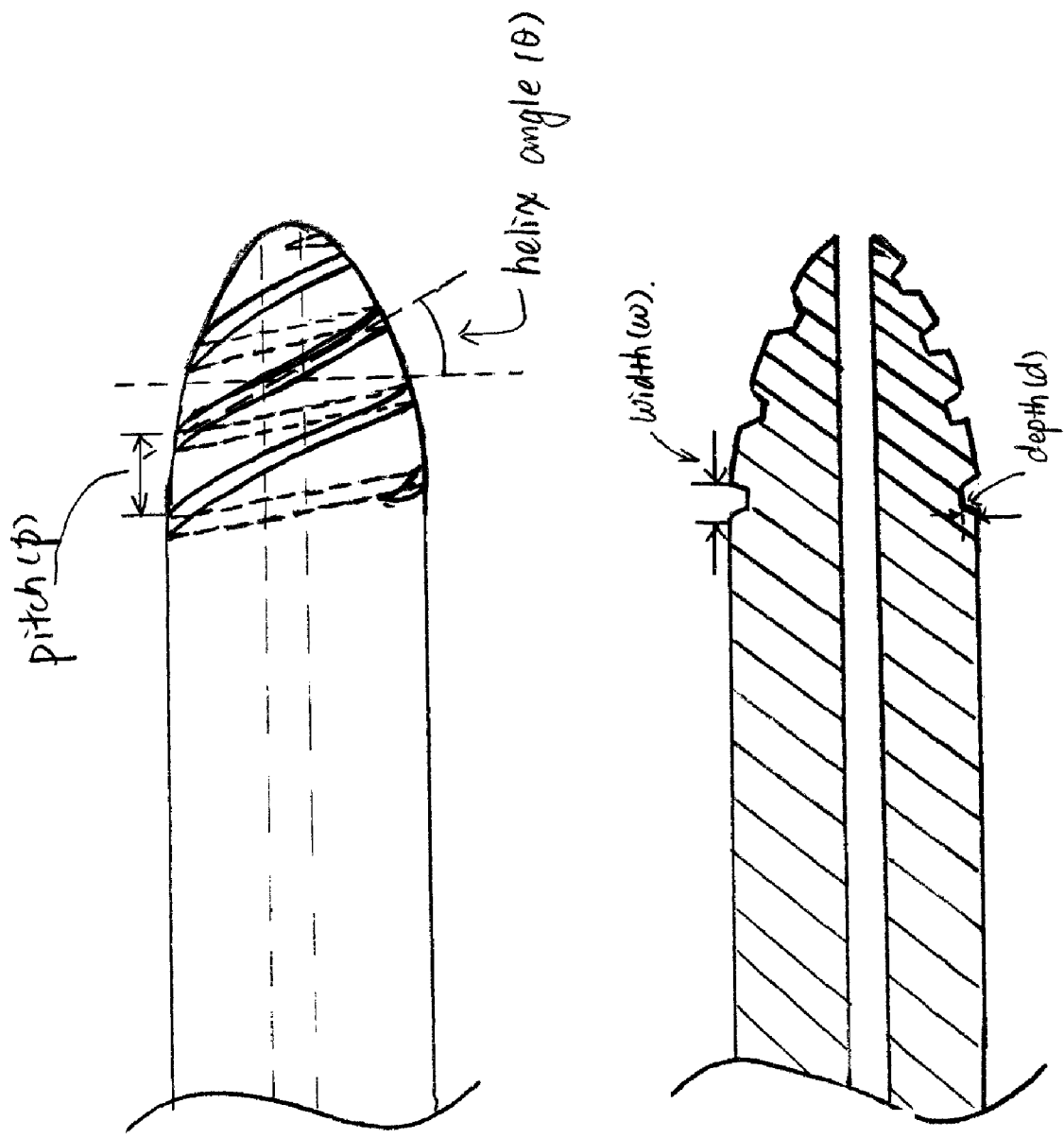
FIGS. 23A and 23B illustrate another embodiment of a threaded dilator.

As illustrated in FIGS. 23A and 23B, each helical thread comprises a helix angle ($\theta$, the angle between the helix and the transverse axis of the dilator), a width (w), a depth (d), and a pitch (p). In some embodiments, the helix angle of each thread may independently be in the range of about 5° to about 85°, sometimes in the rang of about 20° to about 70°, and other times in the range of about 40° to about 50°. The width (w) of each thread may independently be in the range of about 0.05 mm to about 0.5 mm, sometimes in the range of about 0.075 mm to about 0.4 mm, sometimes in the range of about 0.1 mm to about 0.3 mm and other times in the range of about 0.15 mm to about 0.25 mm. The depth (d) of each thread may independently be in the range of about 0.05 mm to about 0.5 mm, sometimes in the range of about 0.1 mm to about 0.4 mm, and other times in the range of about 0.2 mm to about 0.3 mm. The pitch of each thread (p) may be in the range of about 0.25 mm to about 1.5 mm, sometimes in the range of about 0.5 mm to about 1.25 mm, and other times in the range of about 0.75 mm to about 1 mm. These parameters of the thread for a dilator may be independently selected, depending in part on the mechanical characteristics of the tissues to be dilated.

Figure 24:
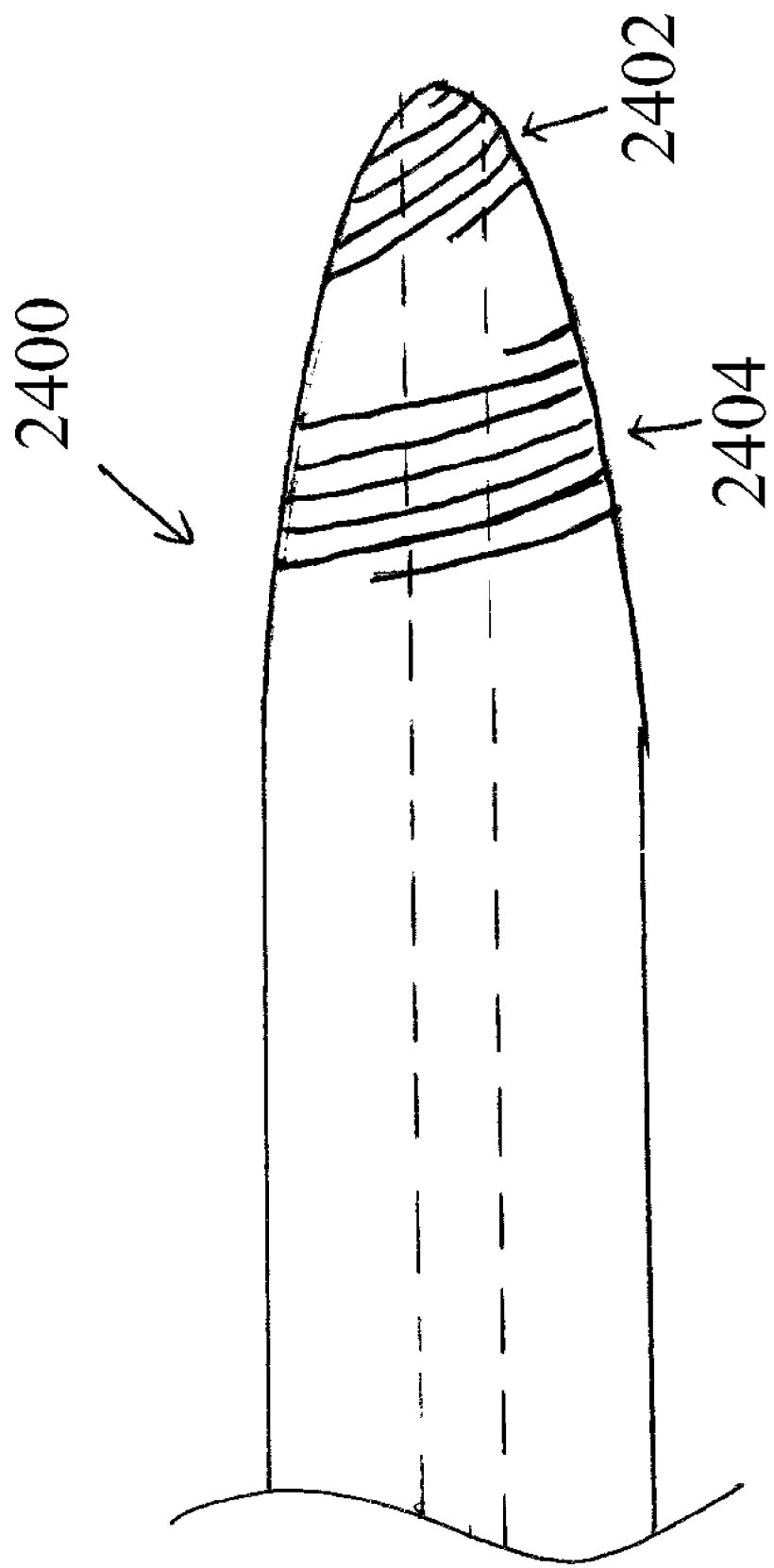
FIG. 24 illustrates another embodiment of a threaded dilator having two threaded regions.

In some embodiments, the dilator may have more than one threaded regions, each of which may comprise threads with different parameters. FIG. 24 illustrates such an example. A dilator 2600 comprises a distal threaded region 2402 and a proximal threaded region 2404. In some variations, the distal region 2402 may comprise helical threads with higher pitch (p) and depth (d), which may provide greater penetrating ability, while the proximal region 2404 may comprise threads with lower pitch (p) and depth (d), which shorten the distance of dilator's advancement with the same number of the rotations and but may provide more control of dilator's motion. In some variations, a dilator may comprise more than two threaded regions. Parameters of the threads at each region may be independently selected depending on the procedures where the dilator may be used.

The shaft of the dilator generally comprises a cylindrical cross-sectional shape. The outer diameter of the shaft may be in the range of about 0.5 mm to about 3 mm, sometimes in the range of about 0.8 mm to about 2 mm, and other times in the range of about 1 mm to about 1.5 mm. In some embodiments, the shaft may comprise a rigid structure in order to have a high torque stiffness. The shaft may be made of, but not limited to, metal, metal alloy (e.g., stainless steel, nickel-cobalt alloys, nickel-titanium alloys, copper-aluminum-nickel alloys, copper-zinc-aluminum-nickel alloys, and combinations thereof), polymer (e.g., polyvinyl chloride, pebax®, polyethylene, silicone rubber, polyurethane, and any copolymers and mixtures thereof) or any combination thereof. Alternatively or additionally, the shaft may be made of strong, but still flexible material. For example, the shaft may be a multi-filar coil, a counter-wound coil, a braid- or coil-reinforced polymeric tube (e.g., composed of polyimide or polyamide), or a hypotube or other flexible metallic tubular structure. In yet other embodiments, the shaft may comprise a light-weight material, such as (but not limited to) aluminum, magnesium, plastics, or carbon fiber. Because a threaded dilator dilates tissues primarily by rotational force, it may be made of thin and relatively light-weight materials that may not tolerate high longitudinally-applied pressure. Lighter and thinner dilators are easier to distribute and handle. In some embodiments, the shaft may be a thin plastic tube with transparent walls. Such dilator will not block the view of visualization equipment that may be used with the dilator. In some variations, the shaft may comprise different sections along its longitudinal axis that are made of different materials. In some embodiments, one or more portions of the shaft may be flexible, and may be capable of bending upon application of one or more forces thereto.

In some embodiments, portions or the entire dilator is coated with one or more lubricious coatings. Non-limiting examples of lubricious coating materials include parylene, polyethylene or Teflon. In other embodiments, the dilator may be coated partially or entirely with one or more coating materials that may improve one or more characteristics of the dilator, including but not limited to biocompatibility and anti-infective properties.

In some embodiments, the taper of the dilator may be integrally formed with the shaft. In other embodiments, the taper may be manufactured separately and attached to the shaft by suitable methods, such as (but not limited to) welding, soldering, adhesive bonding or mechanical bonding. In some embodiments, the taper may be made of the same material as the shaft, but in other embodiments, the taper may be made of a different material from the shaft. For example, the taper may be made of a stiffer material than the shaft for dilating tough tissues or bones. Alternatively, the taper may be made of a more flexible material than the shaft to improve the steerability or maneuverability of the dilator's tip such that the device may be used at anatomical sites with more restricted access.

In addition to the distal port and the proximal port that are communicated with the pressure lumen, a threaded dilator disclosed here may comprise any number of ports at other locations along its body. Each port may have any suitable size, shape, or configurations. The configuration of each port may not be same. In some variations, ports may be used to release one or more gases or fluids from the dilator. In some embodiments, these gases or fluids may comprise one or more therapeutic agents. In other embodiments, gases or fluids may be used to clean or wash away debris that may accumulate between threads. In other variations, ports may allow one or more fluids to drain out of the body through the dilator. In some of these variations, vacuum or suction may be applied to ports. In some variations, these additional ports may be in communication with the pressure lumen. In other variations, they may not be in communication with the pressure lumen but they may be in communication with one or more other interior lumens within the dilator. In some variations, some ports of the dilator may comprise slits of flaps which are configured to remain closed until a certain infusion or aspiration pressure is achieved.

In some variations where a guide wire is used to advance a dilator to reach the target site, the guide wire may also comprise one or more threaded portions, which may facilitate guidewire placement in a controlled manner. In some embodiments, the inner surface of the dilator lumen may comprise threads that mate with the threads on the guide wire such that the dilator may be rotated to advance over the guide wire. Sometimes needles may be used to help guide wire passage through some tissues. One or more portions of the needle may also be threaded to negotiate its paths in complicated anatomical structures.

In some embodiments, advancing the dilator and the dilating procedure may occur under direct visualization. Acquiring access to the epidural space under direct or local visualization permits the operator to visualize the ligamentous tissues as the threaded dilator head engaging and passing through the ligaments. Further, when the operator loses the visualization of the ligament, the operator will be informed that the distal end of the dilator has passed through the ligamentum flavum. By having direct visualization during the placement of the dilator and/or the dilating process, the operator may not need to rely on the pressure change within the dilator's inner lumen to determine whether the distal end of the dilator has engaged or has passed through the ligaments, thereby simplifying the procedure. In some variations, the pressure monitoring may still be employed and used as an independent source for the operator to identify the location of the dilator tip. Further, by directly visualizing the ligamentous tissues, the operator may be able to adjust the dilating angle and/or the rotational force, thereby further lowering risk of over-penetration.

Figure 25:
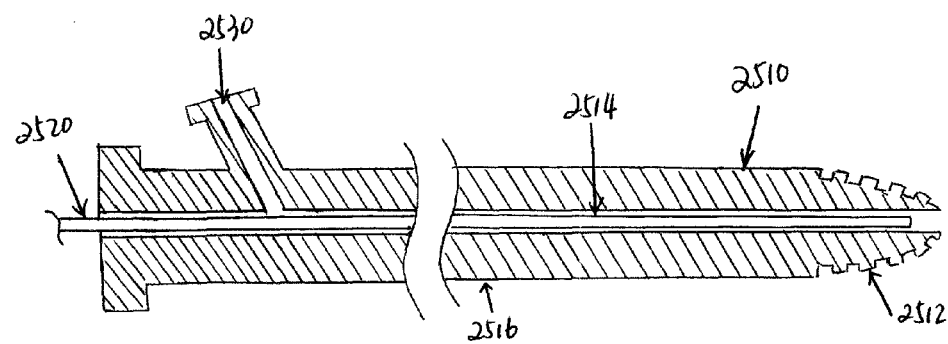
FIG. 25 illustrates one embodiment of a threaded dilator with direct visualization feature having a removably located endoscope in a lumen of the dilator.

The direct visualization may be achieved by a device external to the dilator, such as an endoscope, or may be achieved by one or more visualization devices attached to or otherwise disposed within, on, or around a portion of the dilator. FIG. 25 depicts one embodiment of a dilator 2500 that comprises a threaded distal taper 2512, an elongate shaft 2516 and an inner lumen 2514 spanning the entire longitudinal length of the dilator 2510. The inner lumen 2514 may be configured to receive an endoscope 2520, the outer diameter of which is smaller than the diameter of the lumen 2514. In one embodiment, the endoscope 2520 may be a fiberscope, rod lens scope or "camera on tip" scope, which may receive visual images from its distal end and transmit such images to the proximal end where the operator may read the imaging information. The proximal end of the fiberscope, rod lens scope or "camera on tip" scope may optionally be connected to an external TV or monitor. The fiberscope, rod lens scope or "camera on tip" scope may optionally transmit illumination from a light source to its distal end. In some embodiments, the light source may be an external one attached to the proximal end of the fiberscope, rod lens scope or "camera on tip" scope whereas in other embodiments, the light source may be located at or near the distal end of the fiberscope, rod lens scope or "camera on tip" scope. In some embodiments, the outer diameter of the fiberscope, rod lens scope or "camera on tip" scope may be in the range of about 0.5 mm to about 1.5 mm, sometimes about 0.7 mm to about 1.2 mm, and other times about 0.8 mm to about 1.0 mm. In some embodiments, the endoscope 2520 may be a rigid lens scope, such as a glass-lens scope or a rod-lens scope. In some embodiments, the distal end of the threaded distal taper 2512 may be round or otherwise blunt to reduce inadvertent damage to surrounding tissues.

The endoscope 2520 may comprise a proximal connector that may be used to releasably couple the endoscope with the dilator 2510 through a complementary connector (e.g., a Luer lock). In some embodiments, when the endoscope and the dilator are proximally attached, the distal end of the endoscope may not extend over the distal tip of the dilator, thereby reducing the risk of inadvertent passing the endoscope through the ligament and damaging the nerves and other soft tissues located within the epidural space. In other embodiments, the distal portion of the lumen 2510 may comprise a stopper (e.g., an annular bulge or other types of protruding structure) located on the inner surface of the lumen to limit the distal travel of the endoscope. In still other embodiments, the distal end of the inner lumen 2514 may be close-ended with a transparent cover.

In the embodiment depicted in FIG. 25, dilator 2510 may be made from an optically transparent or translucent material to permit direct or local visualization of relevant structures during dilating processes. In some embodiment, the optically transparent or translucent material may be a polymer. Suitable polymeric materials may include, but not limited to, biomedical grade of clear PVC (XV-3450 from PolyOne Corp. (Avon Lake, Ohio), 2222Rx-70 Clear 000X from Alpha-Gary Corp (Leominster, Mass.), TPE, polyurethane, glass, nylon, Pebax, PET, FEP, PTFE, polyolefin, acrylic, polycarbonate, and polyethylene. In some embodiments, only the threaded taper 2512 of the dilator 2510 is optically transparent or translucent whereas the shaft 2516 of the dilator 2510 may be made from more stiff material, such as metal or metal alloy. In still other embodiments, a distal portion of the dilator shaft 2516, as well as the threaded taper 2514, may be optically transparent or translucent to serve as a viewing area. In some variations, the viewing area may be an optically clear tube. In other variations, the viewing area may comprise one or more circumferential openings through which the endoscope may be exposed. The openings may or may not comprise clear covers. In still other variations, the viewing area may comprise a plurality of refractory surfaces, thereby providing a prismatic effect and enhancing visualization.

The embodiment depicted in FIG. 25 may optionally comprise a proximal port 2530 that is in fluid communication with the inner lumen 2514. In some instances, the port 2530 may be used as an irrigation port to inject pressurized fluids into the inner lumen 2514 in order for the operator to monitor the pressure change within the inner lumen. As noted earlier in this detailed description, the dilator may comprise additional ports to flush out the irrigating fluids from the inner lumen. The flushing streams may be used to push away tissues surrounding the dilator during its advancement or dilating process or to clean or wash away debris that may accumulate between threads.

Figure 26:
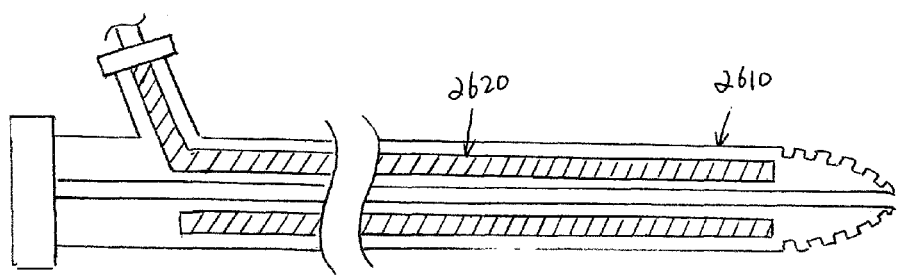
FIG. 26 illustrates another embodiment a threaded dilator with direct visualization feature with optical fibers embedded in the dilator.

FIG. 26 depicts another embodiment of a threaded dilator 2610 with integrated visualization or illumination features. In this particular embodiment, optical fibers 2620 are circumferentially embedded in the dilator 2610. The embedded fibers 2620 comprise at least one fiber to transmit images from distal end to proximal end. The light source may be an external one that is coupled to the proximal end of the embedded fibers 2620 or may also be embedded in the dilator 2610, at its distal end, for example. Dilator 2610 may be optically transparent or translucent to allow direct visualization of anatomic structures outside the dilator. The dilator 2610 may optionally comprise an inner lumen for guidewire placement.

Figure 27:
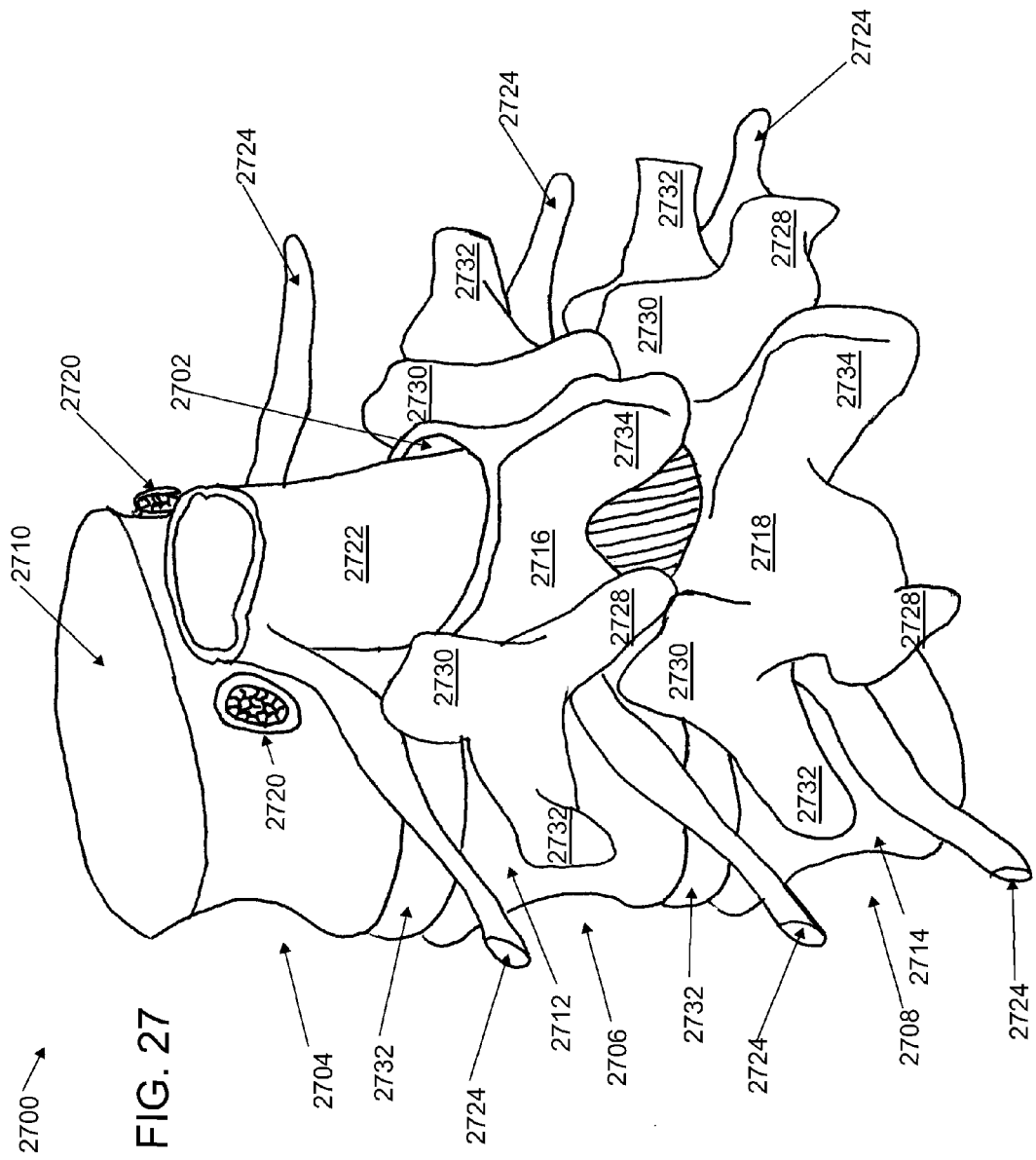
FIG. 27 is a schematic perspective view of a portion of a lumbar spine.
Figure 28:
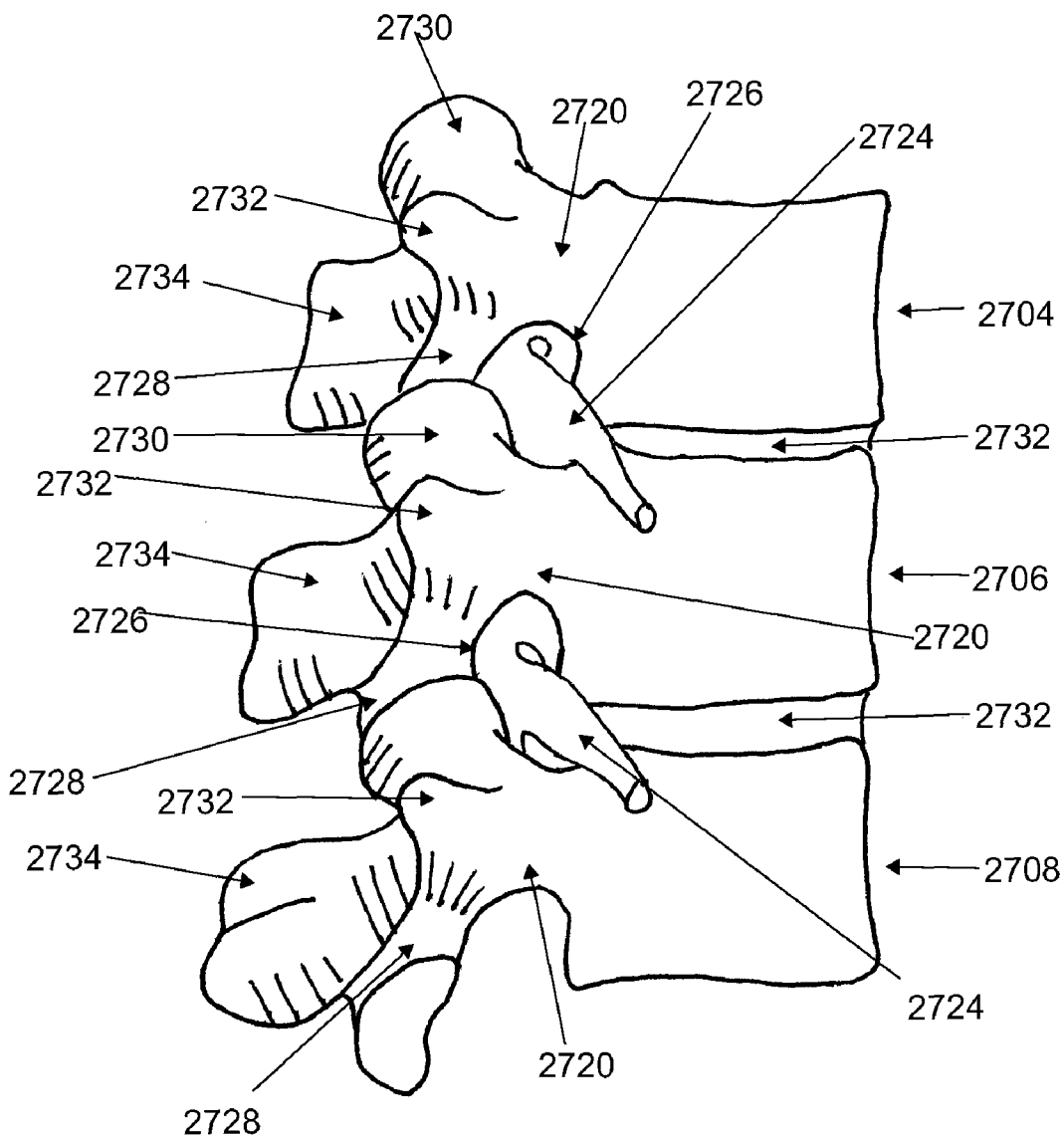
FIG. 28 is a schematic side elevational view of a portion of the lumbar spine.

FIGS. 27 and 28 are schematic views of a lumbar region of a spine 2700. The vertebral canal 2702 is formed by a plurality of vertebrae 2704, 2706, and 2708, which comprise vertebral bodies 2710, 2712 and 2714 anteriorly and vertebral arches 2716 and 2718 posteriorly. The vertebral arch and adjacent connective tissue of the superior vertebra 2704 has been omitted in FIG. 27 to better illustrate the spinal cord 2722 within the vertebral canal 2702. Spinal nerves 2724 branch from the spinal cord 2722 bilaterally and exit the vertebral canal 2702 through intervertebral foramina 2726 (seen best in FIGS. 28 and 29) that are formed by the adjacent vertebra 2704, 2706 and 2708. The intervertebral foramina 2726 are typically bordered by the inferior surface of the pedicles 2720, a portion of the vertebral bodies 2704, 2706 and 2708, the inferior articular processes 2728, and the superior articular processes 2730 of the adjacent vertebrae. Also projecting from the vertebral arches 2716 and 2718 are the transverse processes 2732 and the posterior spinous processes 2734 of the vertebrae 2706 and 2708. Located between the vertebral bodies 2710, 2712 and 2714 are the vertebral discs 2732.

Figure 29:
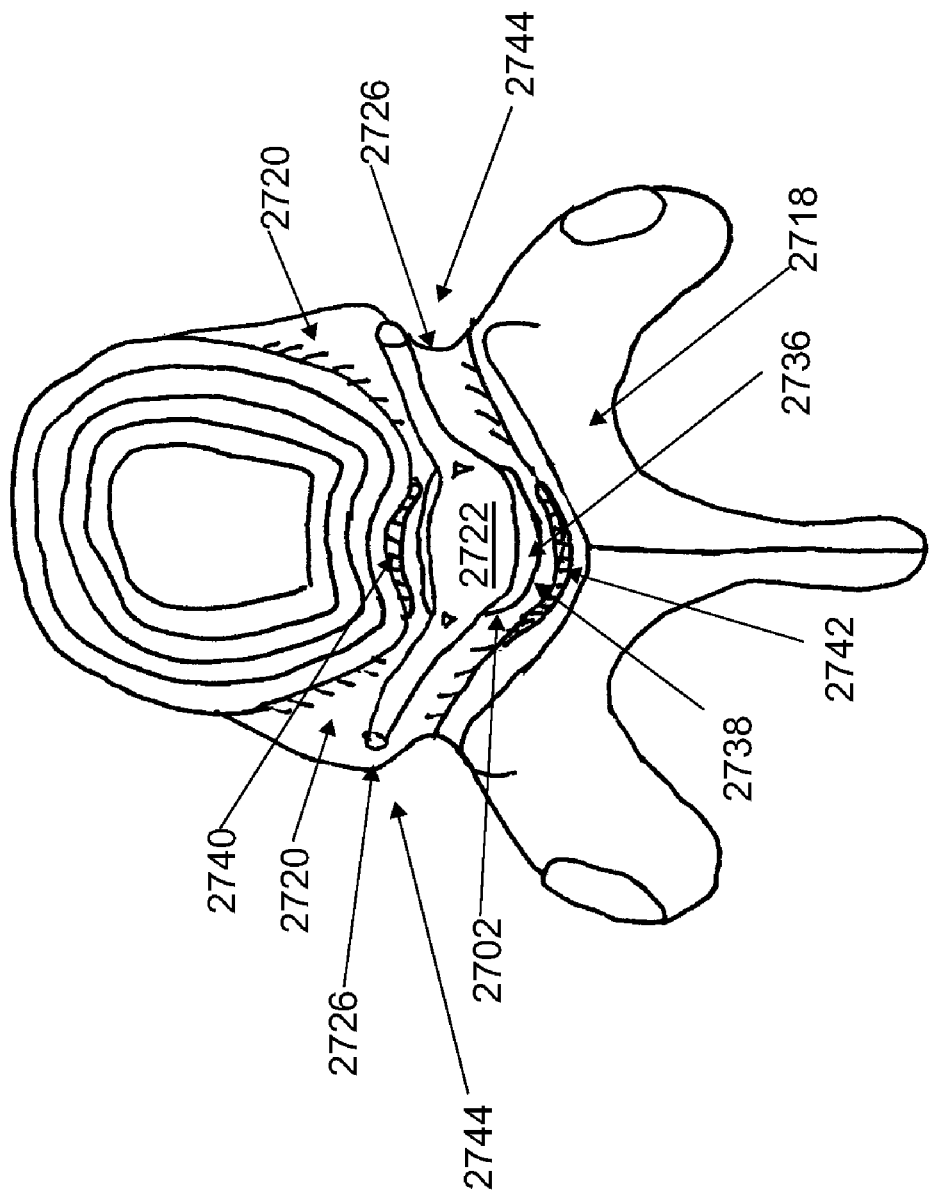
FIG. 29 is a schematic superior view of a portion of a lumbar vertebra and disc.

Referring to FIG. 29, the spinal cord 2722 is covered by a thecal sac 2736. The space between the thecal sac 2736 and the borders of the vertebral canal 2702 is known as the epidural space 2738. The epidural space 2738 is bound anteriorly and posteriorly by the longitudinal ligament 2740 and the ligamentum flavum 2742 of the vertebral canal 2702, respectively, and laterally by the pedicles 2720 of the vertebral arches 2716 and 2718 and the intervertebral foramina 2726. The epidural space 2738 is contiguous with the paravertebral space 2744 via the intervertebral foramina 2726.

Embodiments of threaded dilator with direct visualization and/or illumination described herein may be used to perform discectomy. In particular, such dilator may be used to form a passageway or working channel into the epidural space, through which other surgical instruments may be introduced to the target site and treat the herniated disc.

In one embodiment, a patient may be placed in a sitting or lateral decubitus position with the spine arched anteriorly. The target level along the spine is identified using surface landmarks or other indicia and the skin is prepped and draped. General, regional, or local anesthesia is achieved. A guidewire may be first inserted percutaneously to a location in proximity to or within the epidural space. In some instances, a needle may also be used to facilitate guidewire passage through some tissues. Guidewire placement may be performed under fluoroscopic guidance or other types of indirect visualization including, but not limited to CT or ultrasound. In some instances, a small skin incision is made to facilitate guidewire insertion. Once the placement of the guidewire is confirmed, a dilator with threaded tip may be placed over the guidewire and advanced through the guidewire toward the ligamentum flavum. In some embodiments, a dilator may be percutaneously inserted into the patient's back directly without facilitation of guidewire or needle.

Once the distal tip of the dilator reaches the ligament or an axial resistance is identified by the operator, an endoscope may be inserted into the dilator to allow the dilating process performed under direct visualization. In an alternate embodiment, the endoscope may be first proximally coupled with the dilator through complementary connectors (e.g., Luer lock) prior to the advancement of the two together over the guidewire. In this fashion, direct visualization of the tissues, bones and other anatomic structures along the entire access paths to the epidural space may be visualized to the operator to facilitate the dilator placement. When the distal tip of the dilator engages the ligament, the operator may receive imaging of the ligament as well as feeling of an axial resistance from the ligamentous tissues with high modulus. When such visual and/or tactile feedback is received, the operator may stop applying axial forces upon the dilator and start applying rotational force to the dilator in order to threadingly advance the dilator. Because of slower speed and higher torque of the rotational motion, the threaded dilator dilates through the ligamentous tissues in a more controlled fashion. During dilation, gas or liquids may be irrigated through the inner lumen or additional irrigation channels to clean or wash away debris that accumulated between threads. In some embodiments, a liquid may still be irrigated into the lumen during the advancement of the dilator in order to monitor the inner lumen pressure. The operator may use the rise of the lumen pressure as a secondary confirmation for the placement of the dilator in the ligament. Further, pressurized gas or liquid may push away adjacent anatomical structures or tissues around the dilator, thereby facilitating the advancement of the dilator. When the distal tip of the dilator passes out the anterior surface of the ligamentum flavum and the ligamentous tissues are not visualized through the endoscope, the operator my stop applying rotational force to the dilator. In the mean time, the operator may feel the loss the distal resistance when ligament is penetrated and dilated. Where irrigation of pressurized fluids is used to monitor the inner lumen pressure, the operator may also use the pressure drop as a secondary confirmation for the ligament penetration.

After the ligament is dilated, the endoscope may be withdrawn and an introducer may be inserted over the dilator to maintain access prior to the removal of the dilator. A cannula may then be inserted into the introducer and advanced into the epidural space. Once the cannula enters into the epidural space, the introducer may be withdrawn and the cannula may then be advanced closer to the target site. The placement of the cannula may be guided by fluoroscopy or other type of indirect visualization. In some embodiments, a guidewire or a stylet may be inserted into a lumen in the cannula to facilitate the cannula advancement to the target site through the epidural space. For example, a stylet may be inserted into the cannula to penetrate annular wall at an impingement cite, thereby forming a passageway of a working channel into the intra-discal area. In some instances, a curved cannula and a curved stylet may be used together to access herniated area that is difficult to reach by a straight access. Such curved access has been described in great detail in U.S. Pat. Appl. No. 61/165,968 filed on Apr. 2, 2009 and titled "SYSTEMS AND METHODS FOR NON-LINEAR SPINAL ACCESS", which is hereby incorporated by reference in its entirety. The cannula and/or the stylet may be radiopaque to permit external imaging guidance by fluoroscopy or CT.

Once access to the target site by the cannula has been confirmed, a tissue removal device may be delivered through the cannula, subsequent to the removal of the stylet or guidewire if one is used. In some embodiments, an independent radiographic maker may be inserted into the cannula to evaluate the cannula placement prior to the introduction of the tissue removal device. The tissue removal device may be a mechanical device that may be motorized or manually activated, including but not limited to a burr, a trephine, or a cable-based tissue removal device. Various embodiments of tissue removal devices are described in greater detail in U.S. Pat. Appl. No. 61/083,857, filed on Jul. 25, 2008 and titled "CABLE-BASED TISSUE REMOVAL" which is hereby incorporated by reference in its entirety. The tissue removal device may also be an energy-based device (e.g., laser, RF, high-intensity focused ultrasound) or a chemical based (e.g., injection or infusion of a sclerosant or chemical ablation agent). The tissue removal device may be used to remove at least a portion of disc material (e.g., nucleus fibrosus) by dissecting, pulverizing, aspirating, dissolving or shrinking. The distal portion of the tissue removal device may be radiopaque to allow external imaging monitoring. When the tissue removal is completed, fluoroscopy and/or CT may be used to examine the disc and/or to verify the integrity of the disc. In some embodiments, a small amount of contrast agent may be injected to the treatment site to enhance the visualization. In some embodiments, if another target site needs treatment, the cannula may be repositioned subsequent to the removal of the tissue removal device. The above-described procedures may be repeated for the cannula to acquire access to the second target site. The tissue removal device then may be reintroduced through the cannula to treat the disc. Upon completion of the discectomy, the tissue removal device may be withdrawn, followed by withdrawal of the cannula.

In another example, interlaminar disc access, with out without discectomy, may be performed using the helical dilator with direct visualization. After preparing the patient, an incision may be made through skin and fascia at appropriate site at L5-S1 down to ligamentum flavum. The clear threaded dilator/cannula/endoscope assembly is advanced through incision so that its tipoff the assembly is against the ligamentum flavum. The dilator may then be rotated clockwise with sufficient axial force to screw the dilator into the ligamentum flavum. Once the threads engage the ligament, the application of axial force may be removed or stopped when continuing to rotate the dilator and further penetrate through the ligament. The endoscope or other visualization mechanism permits the physician to visualize the penetration of the tissue and identify when the tip of the dilator has entered into the epidural space. A cannula may then be passed over the dilator to reach the epidural space. The cannula may be positioned or rotated before, during and/or after insertion to maintain the beveled opening of the cannula, if any, in a medial orientation. The dilator is removed and then any endoscopic tools or instruments may be inserted through the cannula and into the epidural space.

Figure 30A:
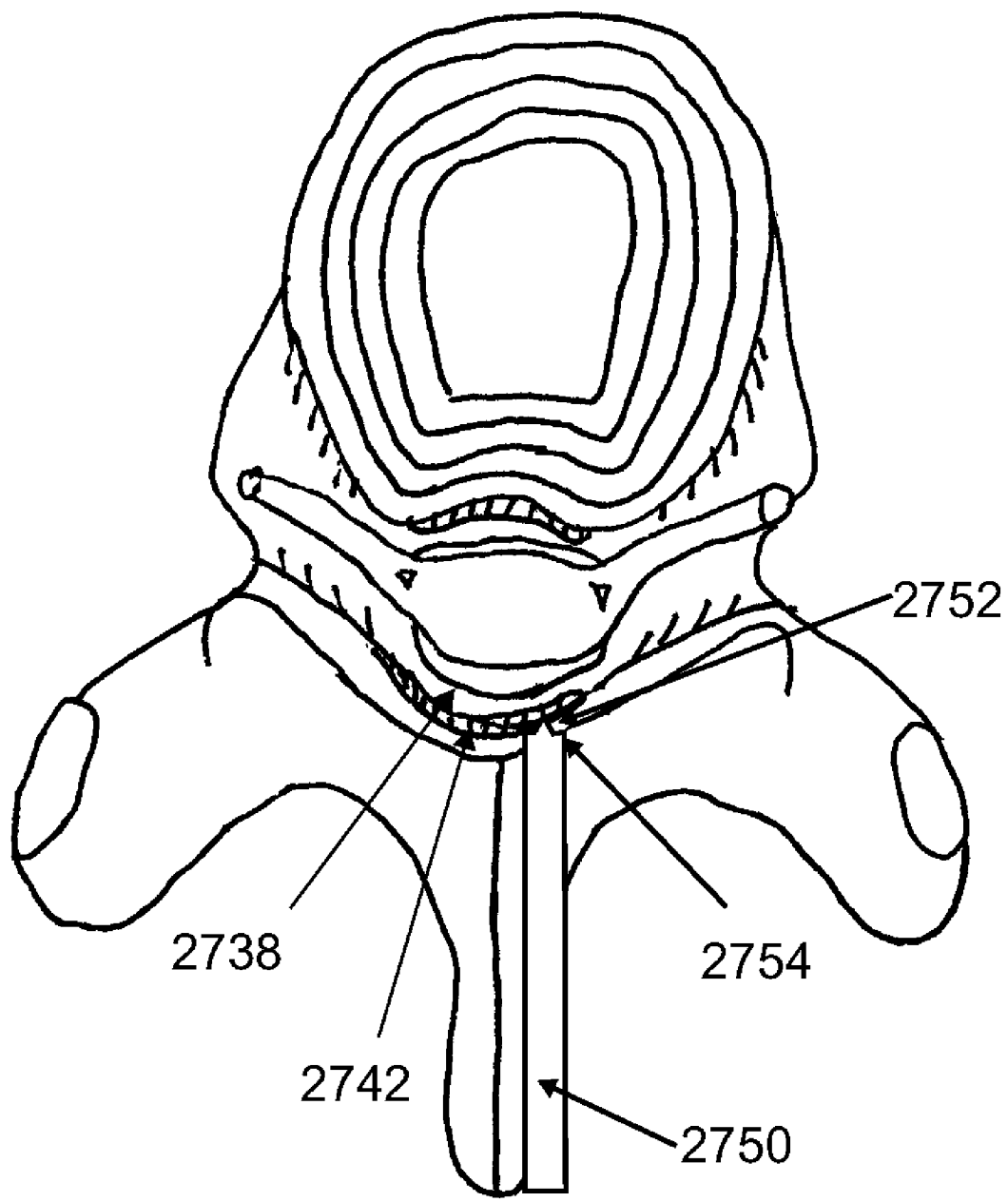
FIGS. 30A and 30B schematically depict the use of a threaded dilator in an interlaminar access procedure to the epidural space.
Figure 30B:
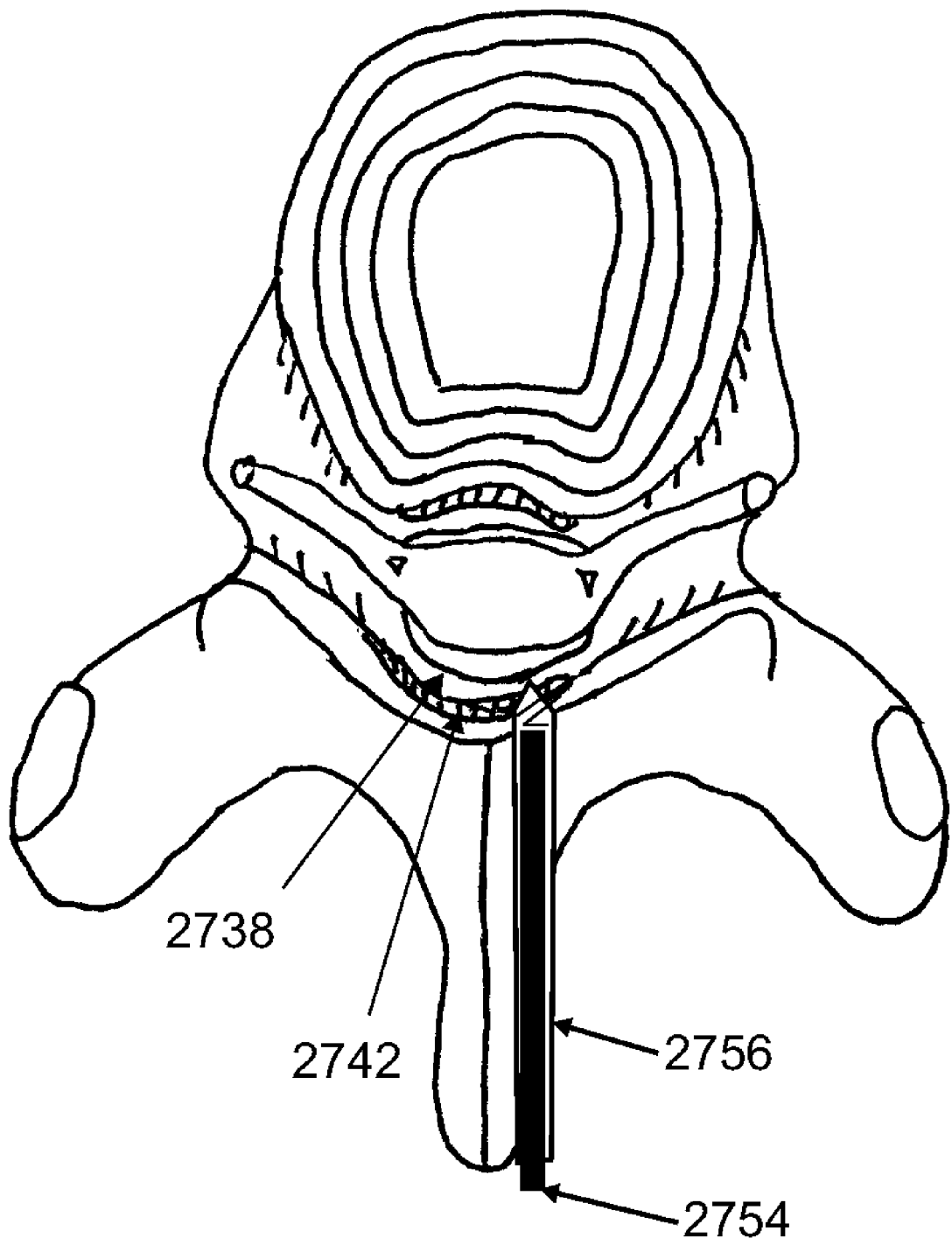

Alternatively, as shown in FIGS. 30A and 30B, a penetrating guidewire 2750 may be inserted partially into the ligamentum flavum 2742. The guidewire 2750 may comprise a penetrating tip 2752 having a tapered length that is less then the thickness of the ligamentum flavum 2742. Proximal to the tip 2752 is a shoulder 2754 or other type of stop structure to resist further penetration of the guidewire tip 2752 into the ligamentum flavum 2742. The penetrating guidewire 2750 is then withdrawn from the cannula and a threaded dilator 2756 with a blunt tip and containing a visualization mechanism (e.g. fiberscope or rod lens endoscope 2758) is then inserted into the partial pathway formed by the penetrating guidewire 2750. The blunt tip threaded dilator 2756 is then rotated to bluntly dissect through the fibers of the ligamentum flavum 2742 without cutting the fibers until the epidural space is reached.

Once in the epidural space, any of a variety of diagnostic and/or therapeutic procedures may be performed as known in the art, including but not limited to use of anesthetic agents, lysis of adhesions, and the like. In one particular example, an embodiment of the grasping endoscope described herein (or any other type of endoscopic system) may be positioned in the epidural space. The grasping endoscope may be inserted with its jaws in a closed configuration. In some instances where a grasping endoscope with a duckbill configuration may be rotationally oriented so that the broader surface of the grasping endoscope is positioned along or against the lateral aspect of the nerve. The jaws or other retracting device of the endoscope, if any, may be actuated to displace or retract the nerve (or other tissue) and to expose the vertebral disc or the posterior longitudinal ligament. An incision may be made into the disc using a microscalpel or other penetrating instrument inserted into the endoscope. A tissue debrider is then inserted into the disc using the pathway formed by the microscalpel. The debrider is actuated then actuated to a pre-specified endpoint or as assessed during the procedure. For example, the debrider may be used for a predetermined amount of time (e.g. about 1 minute to about 10 minutes or more, sometimes about 2 minutes to about 6 minutes, and other times about 2 minutes to about 4 minutes). During or after the procedure, an infusion cannula may be inserted into the disc, with or without requiring removal of the endoscope from the cannula. A radioopaque contract agent may be infused to assess the extent of tissue removal. In some further examples, the same or different tissue removal or tissue treatment tool (e.g. a ronguer) may be inserted into the disc for further tissue removal or other procedure. Preparation of other regions of the spine may also be performed in conjunction with the discectomy procedure. For example, a burr or other type of instrument may be used to shave or prepare the facet joints. Portions of the ligamentum flavum may also be removed by cutting or a punch mechanism. The above steps may be repeated at other levels of the spine until the desired discectomy is achieved and the interbody fusion procedure may then be performed.

In some variations, following advancement of the dilator into the epidural space, a beveled cannula may be inserted into the epidural space using the dilator (e.g. passing the cannula over the dilator). In some examples, the beveled cannula comprises a blunt tip, but with sharpened bevel edges proximal to the blunt tip. In other examples, the beveled cannula comprises a sharpened or piercing tip. In still other examples, the cannula need not be beveled, but comprises a tab or other protrusion proximal to its tip and comprising a cutting or grinding edge. The cannula may be oriented with the its beveled tip generally located laterally and with the face of the bevel oriented medially. The cannula is then rotated to remove bone proximal to the blunt tip, thereby enlarging the pathway to the epidural space. The rotation may be performed under direct or indirect visualization.

In some patients, a transforaminal discectomy or foraminotomy may also be performed using the above interlaminar access procedure. Under fluoroscopic guidance, a spinal needle/stylet may be inserted into the disc through the Kambin Triangle using posterolateral approach at the same level as the disc. Once positioned, the stylet may be replaced with a long guidewire. A cannula-dilator assembly may then be passed over the guidewire and the tip of the assembly may be positioned near the disc in the epidural space. Once positioned, the dilator of the assembly may be replaced with a grasping endoscope. The grasping endoscope is inserted so that the closed jaws are adjacent or against the disc. The endoscope is then tracked posteriorly and medially into the intervertebral foramen and into the central canal. The cannula from the interlaminar access procedure is identified, as well as the traversing nerve/dura mater. Excess soft tissue about the foramen may be removed with a rongeur or other tissue removal instrument. in other examples, the rotatable cutting cannula described previously may also be inserted into the intervertebral foramen to remove bone and enlarge the foraminal opening. With the jaws of the endoscope in a closed configuration, the cannula is retracted to permit the opening of the jaws about the foramen to visualize the nerve exiting the nerve. The endoscope is repositioned as needed in the epidural space lateral to the foramen and a hooded burr or other bone removal instrument configured to protect or resist nerve injury may be used to shave or otherwise remove bone to enlarge the foramen. Upon completion of bone removal, the epidural space may be explored using the endoscope to confirm the location and integrity of the exiting nerve and the endoscope and cannula may be withdrawn.

In the specific embodiment described above, fluoroscopy and/or CT scan may be performed before, during and/or after the cannula placement and/or the subsequent tissue removal to assess the patient's anatomy, the position of the instruments, the structure after tissue removal, and/or to verify the integrity of the disc. It should be understood here that direct visualization may be used in lieu of or in addition to the indirect visualization to provide imaging guidance. For example, the cannula introduced after the ligament dilation may comprise a scope lumen and an endoscope may be inserted and used to provide direct visualization. In one instance, the cannula may be the retractor cannula that has been described in greater detail above.

The use of threaded dilator with direct visualization and/or illumination features in discectomy has been described herein in greater detail. However, it should be understood that such dilator may be used to acquire access to other spinal regions. For example, a threaded dilator equipped with a fiberscope, rod lens scope or "camera on tip" scope may be used to penetrate and dilate an intervertebral foramen. The threading dilation feature combined with direct visualization may reduce the risk of overpenetrating the foramen and thereby, injuring the nerves located in the foramen. Further, a threaded dilator with a variety types of endoscope may be used in various types of access procure. For example, a bronchoscope may be used with a threaded dilator to acquire access to pleural cavity. Other examples of endoscopes that may be used with a threaded dilator include, but not limited to colonoscopes, cystoscopes, bronchoscopes, and gastroscopes.

In another embodiment, the retractor cannula system may be used to perform any of a variety of genitourinary and OB/GYN procedures, including but not limited to cystoscopy (with or without bladder biopsy), renal biopsy, prostate biopsy and surgery, fetoscopy (including optional fetal blood draws), and bladder neck suspension procedures. In one particular example, cystoscopy may be performed using a flexible retractor cannula system with a forward-positioned extendable retractor assembly, but in other embodiments, a rigid retractor cannula system may also be used. In one embodiment, a cystoscopy procedure may be performed by draping a patient in the usual fashion and prepping the urethral orifice with a sterilizing agent and a topical anesthetic. In patients where ureteroscopy may be performed in addition to cystoscopy, regional or general anesthesia may be used instead. A topical anesthetic is optionally applied to the exterior of the retractor cannula system as the retractor cannula system is inserted into the urethral orifice and advanced to the bladder cavity. In some embodiments, the bladder may be filled with a gas or a liquid to expand the bladder wall for viewing. Once in the bladder, the retractor cannula system may be flexed and rotated to view the bladder cavity. Biopsies may be taken as indicated by inserting a biopsy instrument (e.g. a grasper) into a channel of the retractor cannula device, actuating the biopsy instrument and withdrawing the biopsy instrument. The ureteral orifice may be identified and the retractor cannula may be inserted into the ureter. A guidewire may be optionally inserted through the retractor cannula system and into the ureteral orifice to facilitate passage of the retractor cannula system into the ureter. In some embodiments, the retractor assembly of the retractor cannula system may be at least partially expanded during entry and/or advancement of the device, to reduce the risk of ureteral perforation. Depending upon the length of the retractor cannula system, the retractor cannula system may also be advanced into the intrarenal collecting system. If a stone is encountered during the procedure, the jaws of the retractor assembly may be actuated to remove the stone. Alternatively or additionally, a basket or other type of capturing instrument may also be inserted into the retractor cannula system to remove the stone. For stones that are too large to be withdrawn through a channel of the retractor cannula system, a burr or other type of disrupting structure may be used to break up the stone. Once the biopsies and/or stone break-up or removal is completed, the retractor cannula system may be withdrawn.

It is to be understood that this invention is not limited to particular exemplary embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and the include plural referents unless the context clearly dictates otherwise. Thus, for example, reference to "a blade" includes a plurality of such blades and reference to "the energy source" includes reference to one or more sources of energy and equivalents thereof known to those skilled in the art, and so forth.

The publications discussed herein are provided solely for their disclosure. Nothing herein is to be construed as an admission that the present invention is not entitled to antedate such publication by virtue of prior invention. Further, the dates of publication provided, if any, may be different from the actual publication dates which may need to be independently confirmed.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. For all the embodiments described herein, the steps of the method need not be performed sequentially.

What is claimed is:

1. A method for dilating a target tissue, comprising:
    introducing a dilating device having a distal threaded portion and an endoscope removably located in a longitudinal lumen of said dilating device;
    advancing the dilating device axially until the thread portion engages the target tissue;
    rotating the dilating device while visualizing the target tissue using said endoscope until the distal end of the dilating device passes through the target tissue.

2. The method of claim 1, wherein said endoscope is a fiberscope, rod lens scope or "camera on tip" scope.

3. The method of claim 1, wherein said distal threaded portion of said dilating device is optically transparent.

4. The method of claim 1, wherein said distal threaded portion of said dilating device is optically translucent.

5. The method of claim 1, wherein said dilating device is optically transparent.

6. The method of claim 1, wherein said dilating device is optically translucent.

7. A method for treating intervertebral disc defects in a spine, comprising:
    introducing a dilating device having a distal threaded portion and an endoscope removably located in a longitudinal lumen of said dilating device;
    advancing the dilating device axially until the thread portion engages the ligamentum flavum;

rotating said dilating device to dilate ligament enclosing the epidural space while visualizing the ligament using said endoscope until said dilating device passes through the ligament flavum;

advancing a cannula device over the dilating device into the epidural space to a target site;

proximally withdrawing the endoscope from the dilating device, proximally withdrawing the dilating device; and introducing a therapy device into said cannula device to treat a disc defect.

8. The method of claim 7, wherein said endoscope is a fiberscope, rod lens scope or "camera on tip" scope.

9. The method of claim 7, wherein said threaded distal portion of said dilating device is optically transparent.

10. The method of claim 7, further comprising inserting a stylet into said cannula device before introducing said therapy device.

11. The method of claim 10, further comprising penetrating an annular wall of the intervertebral disc with said stylet in order to acquire access to the target site.

12. The method of claim 11, further comprising withdrawing said stylet before introducing said therapy device.

13. The method of claim 7, wherein said cannula comprises a curved distal portion.

14. The method of claim 7, wherein said therapy device is a tissue removal device.

15. The method of claim 7, wherein said therapy device is a cable-based tissue removal device.

16. A method for treating intervertebral disc defects in a spine of a body, comprising:

making in incision into a skin of the body;

introducing a dilating device having a distal threaded portion and an endoscope removably located in a longitudinal lumen of said dilating device to the ligamentum flavum;

dilating the ligament by rotating the dilating device while visualizing the ligament until the distal end of the dilating device passes through the ligamentum flavum;

introducing a cannula device over the dilating device to a portion of the spine;

proximally withdrawing the endoscope;

proximally withdrawing the dilating device;

introducing a therapy device into the cannula device to treat a disc defect; and treating the disc defect.

* * * * *